(12) United States Patent
Cerri et al.

(10) Patent No.: US 8,536,160 B2
(45) Date of Patent: *Sep. 17, 2013

(54) AZAHETEROCYCLYL DERIVATIVES OF ANDROSTANES AND ANDROSTENES AS MEDICAMENTS FOR CARDIOVASCULAR DISORDERS

(75) Inventors: Alberto Cerri, Milan (IT); Giorgio Fedrizzi, Treviglio (IT); Alessandra Benicchio, Lainate (IT); Giuseppe Bianchi, Milan (IT); Patrizia Ferrari, Varese (IT); Mauro Gobbini, Mercallo (IT); Rosamaria Micheletti, Milan (IT); Marco Pozzi, Omega (IT); Piero Enrico Scotti, Cesano Maderno (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 850 days.

This patent is subject to a terminal disclaimer.

(21) Appl. No.: 12/296,532

(22) PCT Filed: Apr. 11, 2007

(86) PCT No.: PCT/EP2007/053521
§ 371 (c)(1),
(2), (4) Date: Mar. 2, 2009

(87) PCT Pub. No.: WO2007/118830
PCT Pub. Date: Oct. 25, 2007

(65) Prior Publication Data
US 2009/0275542 A1 Nov. 5, 2009

(30) Foreign Application Priority Data
Apr. 13, 2006 (EP) ...................................... 06112605

(51) Int. Cl.
*A61K 31/58* (2006.01)
*A61P 9/12* (2006.01)
*C07J 43/00* (2006.01)

(52) U.S. Cl.
USPC ........... 514/176; 552/510; 552/515; 552/516; 552/519; 552/651

(58) Field of Classification Search
USPC .................. 514/176; 552/65, 510, 515, 516, 552/519, 651
See application file for complete search history.

(56) References Cited

U.S. PATENT DOCUMENTS
3,013,009 A 12/1961 Marshall
5,144,017 A 9/1992 LaBella et al.

FOREIGN PATENT DOCUMENTS
EP 0825197 A2 2/1998
GB 868303 A 5/1961
GB 966060 A 8/1964

OTHER PUBLICATIONS

Schutz, S., et al., Guanylhydrazones with a positive inotropic cardiac effect, Arzneimittel-Forschung, Jan. 1969, vol. 19(1), pp. 69-75.
Temma, K., et al., Effects of progesterone derivatives on sodium pump activity and force of myocardial contraction in isolated guinea pig heart, Research Communications in Chemical Pathology and Pharmacology, 1983, vol. 41(1), pp. 51-63.

*Primary Examiner* — Sreeni Padmanabhan
*Assistant Examiner* — Sahar Javanmard
(74) *Attorney, Agent, or Firm* — Lucas & Mercanti, LLP

(57) ABSTRACT

Compounds of formula (I) wherein: the groups are as defined in the description, are useful for the preparation of medicaments for the treatment of cardiovascular disorders, in particular heart failure and hypertension. The compounds are inhibitors of the enzymatic activity of the Na+, K+-ATPase. They are useful for the preparation of a medicament for the treatment of a disease caused by the hypertensive effects of endogenous ouabain, such as renal failure progression in autosomal dominant polycystic renal disease (ADPKD), preeclamptic hypertension and proteinuria and renal failure progression in patients with adducin polymorphisms.

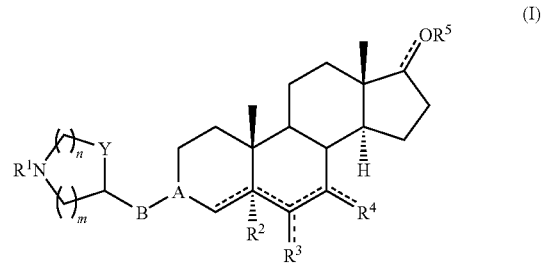

13 Claims, No Drawings

AZAHETEROCYCLYL DERIVATIVES OF ANDROSTANES AND ANDROSTENES AS MEDICAMENTS FOR CARDIOVASCULAR DISORDERS

The present invention relates to new azaheterocyclyl derivatives at position 3 of 5- and/or 6- and/or 7-substituted androstanes and androstenes, processes for their preparation, and pharmaceutical compositions containing them for the treatment of cardiovascular disorders, such as heart failure and hypertension.

BACKGROUND OF THE INVENTION

Cardiovascular diseases are still the first cause of morbidity and mortality in the western world; among these, hypertension and heart failure are two frequent diseases. Hypertension is one of the most important cardiovascular risk factor and more than one third of population over 60 suffers from this disease. Congestive heart failure affects 1-2% of the population and even 10% of the very elderly; the percentage is expected to rise (Sharpe, N. et al., *The Lancet*, 1998, 352 (suppl. 1), 3-17). Beside, hypertension may be one of more important causes of heart failure in the elderly (*Eur. Heart J.*, 2001, 22, 1527-1560).

Although a number of effective drugs are available for the treatment of both hypertension and heart failure, further research is in progress to find more effective and safe compounds.

Several drugs are used in combination for the treatment of heart failure, and among positive inotropic agents, digoxin is the most prescribed digitalis cardiac glycoside that can improve the myocardial performance. A very well-known drawback of digitalis drugs is their arrhythmogenic side-effect. Evidence of digitalis toxicity emerges at two- to three-fold higher serum concentration than the therapeutic dose, such as disturbances of conduction and cardiac arrhythmias which are characteristics of digitalis toxicity (Hoffman, B. F; Bigger, J. T. *Digitalis and Allied Cardiac Glycosides. In The Pharmacological Basis of Therapeutics*, 8th ed.; Goodman Gilman, A.; Nies, A. S.; Rall, T. W.; Taylor, P., Eds.; Pergamon Press, New York, 1990, pp 814-839).

The capability of the natural digitalis compounds to increase the myocardial force of contraction is strictly related to their cardenolide structure having a 17β-lactone on a 14-hydroxy-5β,14β-androstane skeleton.

DESCRIPTION OF THE PRIOR ART

In the field of steroidal derivatives some groups of compounds are reported to possess positive inotropic properties or other activities related to the cardiovascular system.

Particularly, within pregnane derivatives the following papers are interesting.

GB 868,303 discloses pregnane-20-one derivatives possessing progestational and antifibrillatory action.

Other aminoalkylesters of 3β-hydroxypregn-5-en-20-one derivatives are disclosed by GB 966,060, with anorectic, antiarrhythmic and antiatherogenic activities, and U.S. Pat. No. 3,013,009, with eurithmic, anticonvulsant, and antihypertensive activities.

U.S. Pat. No. 5,144,017 discloses "compounds that bind to the digitalis receptor" including androstane and pregnane derivatives. According to the inventors, the binding to the digitalis receptor parallels the ability to elicit characteristic cellular response. The inventors focus on the capability of the different classes of steroids of yielding glycosides derivatives with typical digoxin-like actions on the heart as well as on other tissues, which seems to be important improve the toxicity of these compounds. Even though some androstane derivatives are reported, the more interesting compounds are 3-glycosides of pregnane derivatives.

Pregnane guanyhydrazones with positive inotropic cardiac effect are reported by S. Schütz, et al., *Arzneimittel-Forschung*, 1969, 19, 69-75. Particularly relevant to the activity of these compounds is the guanyl-hydrazone substituent, since "replacement of the guanyl hydrazone groups by other related residues results in a loss of activity".

Other pregnene-20-one derivatives, such as clormadinone acetate and megestrol acetate are reported to inhibit the activity of $Na^+$, $K^+$-ATPase but they were not "capable of eliciting an inotropic action by themselves" (K Temma, et al., *Research. Comm. Chem. in Pathology and Pharmacology*, 1983, 41, 51-63).

In the field of 5α,14α-androstane derivatives some groups of compounds are reported to possess positive inotropic properties.

GB 1,175,219 and U.S. Pat. No. 3,580,905 disclose 3-(aminoalkoxycarbonylalkylene)steroid derivatives which possess digitalis like activities with a ratio between the dose which produces toxic symptoms (onset of cardiac arrhythmias) and the effective dose comparable with such a ratio as measured for standard cardiac glycosides. Besides no clear advantage over digitalis glycosides, the compounds with the highest ratio produce the lowest increase in contractile force.

6-Hydroxy and 6-oxoandrostane derivatives are disclosed in EP 0 825 197 as ligands and inhibitors of $Na^+$, $K^+$-ATPase, and positive inotropic agents, possessing a lower toxicity when compared with digoxin, as evaluated on the basis of the acute toxicity in mice. The same compounds are also reported by S. De Munari, et al., *J. Med. Chem.* 2003, 64, 3644-3654.

The evidence that high levels of endogenous ouabain (EO), a closely related isomer of ouabain, are implicated in human hypertension and cardiac hypertrophy and failure stimulated the pharmacological research for developing novel anti-hypertensive agents active as ouabain antagonists. The pathogenetic mechanisms through which increased EO levels affect cardiovascular system involve the modulation of Na—K ATPase, the key enzyme responsible for renal tubular sodium reabsorption and the activation of signalling transduction pathways implicated in growth-related gene transcription. By studying both genetic and experimental rat models of hypertension and comparing them with humans, it has been demonstrated that elevated levels of circulating EO and the genetic polymorphism of the cytoskeletal protein adducin associate with hypertension and high renal Na—K pump activity. Ouabain itself induces hypertension and up-regulates renal Na—K pump when chronically infused at low doses into rats (OS). In renal cultured cells, either incubated for several days with nanomolar concentrations of ouabain or transfected with the hypertensive adducin genetic variant, the Na—K pump results enhanced. Moreover, both EO and adducin polymorphism affect cardiac complications associated to hypertension, the former through the activation of a signalling transduction pathway. As a consequence, a compound able to interact with the cellular and molecular alterations, sustained by EO or mutated adducin, may represent the suitable treatment for those patients in whom these mechanisms are at work (Ferrandi M., et al., Curr Pharm Des. 2005; 11(25): 3301-5).

As reported above, the crucial point of positive inotropic agents is the ability to discriminate between the potency in inducing an increase of myocardial force of contraction and the onset of cardiac arrhythmias.

There is still a constant need to make available drugs showing a better therapeutic ratio and/or a longer duration of action, both of them important factors for the compliance of patients. Preferably, the drugs can be administered by the oral route.

Dehydroepiandrosterone 3β-aminoethers or aminoesters substituted in position 7 with a keto or optionally substituted alkoxy groups are disclosed in US 2003/0054021 and WO 03/035023 A1 for the cosmetical or therapeutical treatments of cutaneous disorders related to keratinous afflictions.

3-Dialkylaminoethers and 3-dialkylaminothioethers of 3β-hydroxy-6α-methylandrostanes or of 3β-hydroxy-6-methyl-5-androstenes are disclosed in U.S. Pat. No. 3,210,386 as hypocholesterolemic and antiparasitic agents.

SUMMARY OF THE INVENTION

It has now been found that 3-azaheterocyclyl derivatives of 5- and/or 6- and/or 7-substituted androstanes and androstenes meet the needs of to provide drugs with a better therapeutic ratio and/or longer duration of action.

The compounds of the present invention show a higher efficacy and/or better therapeutic ratio and/or a longer duration of action; all these factors are important for the compliance of patients.

The compounds of the present invention have the general formula (I):

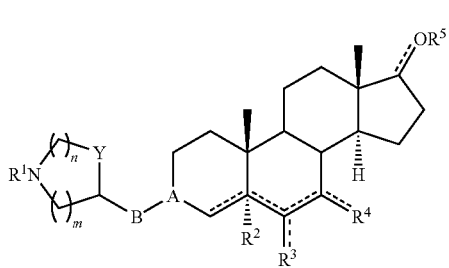

I wherein:
A is $CH\sim X$, $C=N\sim O$, $CR^6\sim CH=CH\sim$, $CR^6\sim CH_2$, $CR^7\sim XC=O$, $CR^7\sim XC(=O)X'$, wherein the left end carbon atom in any of these groups is at position 3 of the androstane ring;
where:
X and X', which can be the same or different, are O, $S(O)_x$ or $NR^8$;
$R^6$ is hydrogen or hydroxy;
$R^7$ is H, $C_1$-$C_6$ straight or branched alkyl;
$R^8$ is H, $C_1$-$C_6$ straight or branched alkyl,
x is the number 0 or 1 or 2;
B is a $C_1$-$C_4$ straight or branched alkylene or can be a single bond so that the A is directly linked to the nitrogen-containing heterocycle;
Y is $CH_2$, oxygen, sulphur or $NR^1$, and when two $R^1$ are present at the same time they can be the same or different;
$R^1$ is H, $C_1$-$C_6$ straight or branched alkyl, optionally substituted by one or more hydroxy, methoxy, ethoxy, or $R^1$ is phenyl($C_1$-$C_4$) straight or branched alkyl or $C(=NR^9)NHR^{10}$;
$R^9$ and $R^{10}$, which can be the same or different, are H, $C_1$-$C_6$ straight or branched alkyl group, or $R^9$ and $R^{10}$ can be taken together with the nitrogen atoms and the guanidinic carbon atom to form an unsubstituted or substituted saturated or unsaturated mono heterocyclic 5- or 6-membered ring optionally containing another heteroatom selected from the group consisting of oxygen, sulphur or nitrogen;
$R^2$ is H, $C_1$-$C_6$ straight or branched alkyl, $ONO_2$, $OR^{11}$;
$R^{11}$ is H, $C_1$-$C_6$ straight or branched alkyl, optionally substituted by one or more hydroxy, methoxy, ethoxy or $R^{11}$ is allyl or propargyl;
when the bonds ----- linking the carbon atom in position 6 of the androstane skeleton with $R^3$ and the carbon atom in position 7 with $R^4$ are independently a double bond, $R^3$ and $R^4$, being $R^3$ and $R^4$ the same or different, are, O, with the meaning of a keto group, $N\sim OR^{12}$, or $CR^{13}R^{14}$;
$R^{12}$ is H, $C_1$-$C_6$ straight or branched alkyl group, optionally substituted by one or more hydroxy, methoxy, ethoxy groups, or $R^{12}$ is allyl or propargyl;
$R^{13}$ and $R^{14}$, which can be the same or different, are H, $C_1$-$C_6$ straight or branched alkyl group, optionally substituted by one or more hydroxy, methoxy, ethoxy, or $R^{13}$ and $R^{14}$, which can be the same or different, are allyl, propargyl, F, $COOR^{15}$, CN, $CONR^{16}R^{17}$, or $R^{13}$ and $R^{14}$ taken together form a cycloalkylene substituent;
$R^{15}$ is H, $C_1$-$C_6$ straight or branched alkyl, optionally substituted by one or more hydroxy, methoxy, ethoxy;
$R^{16}$ and $R^{17}$, which can be the same or different, are H, $C_1$-$C_6$ straight or branched alkyl group, or $R^{16}$ and $R^{17}$ can optionally be taken together with the nitrogen atom to form a heterocyclic group;
when the bonds ----- linking the carbon atom in position 6 of the androstane skeleton with $R^3$ and the carbon atom in position 7 with $R^4$ are independently single bonds, $R^3$ and $R^4$, which can be the same or different, are H, $C_1$-$C_6$ straight or branched alkyl group, vinyl, ethynyl, $COOR^{15}$, CN, $CONR^{16}R^{17}$, $OR^{18}$, $ONO_2$, NHCHO, $NHCOCH_3$, $CH=N\sim OH$, spirocyclopropane, spirooxirane, where the alkyl group can be optionally substituted by one or more hydroxy, methoxy, ethoxy;
$R^{15}$, $R^{16}$, and $R^{17}$ are as above defined,
$R^{18}$ is H, $C_1$-$C_6$ straight or branched alkyl optionally substituted by one or more hydroxy, methoxy, ethoxy;
$R^5$ is H, $C_1$-$C_6$ straight or branched alkyl group or $C_2$-$C_6$ acyl group when the bond ----- in position 17 of the androstane skeleton is a single bond and, as a consequence, the remaining substituent in position 17 is H, and $R^5$ is not present when the bond ----- in position 17 is a double bond with the meaning of a keto group;
n is the number 0 or 1 or 2 or 3;
m is the number 0 or 1 or 2 or 3;
$R^{15}$, $R^{16}$, and $R^{17}$, when present in the same compound in different positions, can be the same or different,
the symbol $\sim$ is an α or β single bond or an E or Z diastereoisomer when it is linked to a double bond,
the symbol ----- in positions 4, 5, 6, 7, and 17 is, independently, a single or double bond, and when it is a single exocyclic bond in positions 6, 7, or 17, it can be an α or β single bond;
with the following provisos:
when A is $CR^7\sim XC=O$, or $CR^8\sim XC=OX'$, wherein $R^7$ and $R^8$ are hydrogen, X is oxygen and X' is O or NH, and when A is $CH\sim X$, wherein X is oxygen, the symbol ----- in position 6 linking $R^3$ is a single bond or when the symbol ----- in position 6 linking $R^3$ is a double bond $R^4$ is not oxygen, with the symbol ----- in position 7 linking $R^4$ meaning a double bond, or $R^4$ is not $OR^{18}$, with the symbol ----- in position 7 linking $R^4$ meaning a single bond, that at least one of $R^2$, $R^3$ and $R^4$ in the same structure is not hydrogen.

Where the compounds of formula (I) can exhibit tautomerism, the formula is intended to cover all tautomers; the invention includes within its scope all the possible stereoisomers, Z and E isomers, optical isomers and their mixtures, the metabolites and the metabolic precursors of compound of formula (I).

In the context of the present invention metabolite and metabolic precursor means active metabolite and metabolic precursor, namely a compound of formula (I) which has been transformed by a metabolic reaction, but substantially maintains or increases the pharmacological activity.

Examples of metabolites or metabolic precursors are hydroxylated, carboxylated, sulphonated, glycosylated, glycuronated, methylated or demethylated oxidated or reduced derivatives of the compounds of formula (I).

Some compounds of formula (I) can also be prodrugs of the active forms.

Also the pharmaceutical acceptable salts are included in the scope of the invention.

Pharmaceutical acceptable salts are salts which retain the biological activity of the base and are derived from such known pharmacologically acceptable acids such as, e.g., hydrochloric, hydrobromic, sulfuric, phosphoric, nitric, fumaric, succinic, oxalic, malic, tartaric, maleic, citric, methanesulfonic or benzoic acid and others commonly used in the art.

The $C_1$-$C_6$ alkyl groups may be branched, straight chain or cyclic groups, e.g. methyl, ethyl, n-propyl, i-propyl, n-butyl, t-butyl, cyclopentyl or cyclohexyl.

The $C_1$-$C_4$ alkylene is preferably methylene, ethylene, trimethylene, propylene, tetramethylene or dimethylethylene.

The $C_2$-$C_6$ acyl groups may branched or straight or cyclic chain groups and preferably are acetyl, propionyl, butyryl, pivaloyl, cyclopentanecarbonyl.

Further object of the present invention is the use of said compounds of general formula (I) as medicament, in particular in the preparation of a medicament useful in the treatment of cardiovascular diseases such as heart failure and hypertension.

DETAILED DESCRIPTION OF THE INVENTION

According to one preferred embodiment of the present invention, the compounds of formula (I) are those in which the symbols $R^2$ and $R^4$ represent H, the symbol $R^3$ represents oxygen, with the meaning of keto, methylene, difluoromethylene, hydroxyimino, methoxyimino, when the symbols ----- in position 6 linking $R^3$ and in position 17 represent a double bond, while the other symbols ----- represent single bonds, and the symbol

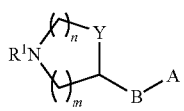

represents (R-3-pyrrolidinyloxy)imino, (S-3-pyrrolidinyloxy)imino, (RS-3-pyrrolidinyloxy)imino, 3-azetidinyloxyimino, 3α-[3-(S)-pyrrolidinylthio], 3α-[3-(R)pyrrolidinylthio], 3α-[3-(RS)-pyrrolidinylthio], 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

In a second preferred embodiment of the present invention, the compounds of formula (I) are those in which the symbols $R^2$ and $R^4$ represent H, the symbol $R^3$ represents α-hydroxy, α-methyl, α-carbamoyl, α-methoxycarbonyl, α-hydroxymethyl, α-(2-hydroxyethyl), α-methoxy-methyl, α-nitroxy, α-formylamino, α-ethynyl, β-hydroxy, the symbol ----- in position 17 represents a double bond while the other symbols ----- represent single bonds, and the symbol

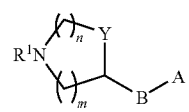

represents (R-3-pyrrolidinyloxy)imino, (S-3-pyrrolidinyloxy)imino, (RS-3-pyrrolidinyl-oxy)imino, 3-azetidinyloxyimino, 3α-[3-(S)pyrrolidinylthio], 3α-[3-(R)-pyrrolidinylthio], 3α-[3-(RS)-pyrrolidinylthio], 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

In a third preferred embodiment of the present invention, the compounds of formula (I) are those in which the symbol $R^2$ represents hydroxy, the symbol $R^4$ represents H, the symbol $R^3$ represents oxygen, with the meaning of keto, methylene, difluoromethylene, hydroxyimino, methoxyimino, when the symbols ----- in position 6 linking $R^3$ and in position 17 represent double bonds while the other symbols ----- represent single bonds, and the symbol

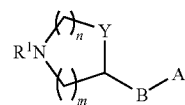

represents (R-3-pyrrolidinyl-oxy)imino, (S-3-pyrrolidinyloxy)imino, (RS-3-pyrrolidinyloxy)imino, 3-azetidinyloxyimino, 3α-[3-(S)-pyrrolidinylthio], 3α-[3-(R)pyrrolidinylthio], 3α-[3-(RS)-pyrrolidinylthio], 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

In a fourth preferred embodiment of the present invention, the compounds of formula (I) are those in which the symbol $R^2$ represents hydroxy, the symbols $R^4$ represent H, the symbol $R^3$ represents α-hydroxy, α-methyl, α-carbamoyl, α-methoxycarbonyl, α-hydroxymethyl, α-methoxymethyl, α-nitroxy, α-formylamino, α-ethynyl, the symbol ----- in position 17 represents a double bond while the other symbols ----- represent single bonds, and the symbol

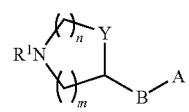

represents (R-3-pyrrolidinyloxy)imino, (S-3-pyrrolidinyloxy)imino, (RS-3-pyrrolidinyl-oxy)imino, 3-azetidinyloxyimino, 3α-[3-(S)-pyrrolidinylthio], 3α-[3-(R)-pyrrolidinylthio], 3α-[3-(RS)-pyrrolidinylthio], 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

In a fifth preferred embodiment of the present invention, the compounds of formula (I) are those in which the symbols $R^2$ and $R^3$ represent H, the symbol $R^4$ represents oxygen, with the meaning of keto, methylene, difluoromethylene, hydroxyimino, methoxyimino, when the symbols ----- in position 7 linking $R^4$ and in position 17 represent a double bond, while the other symbols ----- represent single bonds, and the symbol

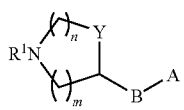

represents (R-3-pyrrolidinyloxy)imino, (S-3-pyrrolidinyloxy)imino, (RS-3-pyrrolidinyloxy)imino, 3-azetidinyloxyimino, 3α-[3-(S)-pyrrolidinylthio], 3α-[3-(R)-pyrrolidinylthio], 3α-[3-(RS)-pyrrolidinylthio], 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

In a sixth preferred embodiment of the present invention, the compounds of formula (I) are those in which the symbols $R^2$ and $R^3$ represent H, the symbol $R^4$ represents α-hydroxy, α-methyl, α-carbamoyl, α-methoxycarbonyl, α-hydroxymethyl, α-methoxymethyl, α-nitroxy, α-formylamino, α-ethynyl, β-hydroxy, β-methyl, β-carbamoyl, β-methoxycarbonyl, β-hydroxymethyl, β-methoxymethyl, β-nitroxy, β-formylamino, β-ethynyl, the symbol ----- in position 17 represents a double bond while the other symbols ----- represent single bonds, and the symbol

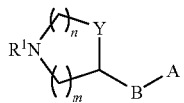

represents (R-3-pyrrolidinyloxy)imino, (S-3-pyrrolidinyloxy)imino, (RS-3-pyrrolidinyloxy)imino, 3-azetidinyloxyimino, 3α-[3-(S)-pyrrolidinylthio], 3α-[3-(R)pyrrolidinylthio], 3α-[3-(RS)-pyrrolidinylthio], 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

In a seventh preferred embodiment of the present invention, the compounds of formula (I) are those in which the symbol $R^2$ represents hydroxy, the symbols $R^3$ represent H, the symbol $R^4$ represents oxygen, with the meaning of keto, methylene, hydroxyimino, methoxyimino, when the symbol ----- in position 7 linking $R^4$ and in position 17 represents a double bond while the other symbols ----- represent single bonds, and the symbol

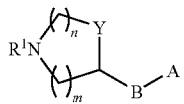

represents (R-3-pyrrolidinyloxy)imino, (S-3-pyrrolidinyloxy)imino, (RS-3-pyrrolidinyloxy)imino, 3-azetidinyloxyimino, 3α-[3-(S)-pyrrolidinylthio], 3α-[3-(R)pyrrolidinylthio], 3α-[3-(RS)-pyrrolidinylthio], 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

In an eighth preferred embodiment of the present invention, the compounds of formula (I) are those in which the symbol $R^2$ represents hydroxy, the symbols $R^3$ represent H, the symbol $R^4$ represents α-hydroxy, α-methyl, α-carbamoyl, α-methoxycarbonyl, α-hydroxymethyl, α-methoxymethyl, α-nitroxy, α-formylamino, α-ethynyl, β-methyl, β-carbamoyl, β-methoxycarbonyl, β-hydroxymethyl, β-methoxymethyl, β-nitroxy, β-formylamino, β-ethynyl, the symbol ----- in position 17 represents a double bond while the other symbols ----- represent single bonds, and the symbol

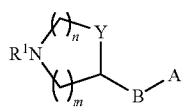

represents (R-3-pyrrolidinyloxy)imino, (S-3-pyrrolidinyloxy)imino, (RS-3-pyrrolidinyl-oxy)imino, 3-azetidinyloxyimino, 3α-[3-(S)-pyrrolidinylthio], 3α-[3-(R)pyrrolidinylthio], 3α-[3-(RS)-pyrrolidinylthio], 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

In an ninth preferred embodiment of the present invention, the compounds of formula (I) are those in which the symbol $R^2$ represents hydroxy, the symbols $R^3$ and $R^4$ represent H, the symbol ----- in position 17 represents a double bond while the other symbols ----- represent single bonds, and the symbol

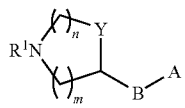

represents (R-3-pyrrolidinyloxy)imino, (S-3-pyrrolidinyloxy)imino, (RS-3-pyrrolidinyloxy)imino, 3-azetidinyloxyimino, 3α-[3-(S)-pyrrolidinylthio], 3α-[3-(R)pyrrolidinylthio], 3α-[3-(RS)-pyrrolidinylthio], 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

In a tenth preferred embodiment of the present invention, the compounds of formula (I) are those in which the symbol $R^2$ represents H, the symbols $R^3$ represents α-hydroxymethyl, and $R^4$ represents α-hydroxy or keto, when the symbol ----- in position 17 represents a double bond while the other symbols ----- represent single bonds, and the symbol

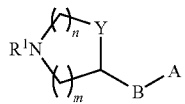

represents (R-3-pyrrolidinyloxy)imino, (S-3-pyrrolidinyloxy)imino, (RS-3-pyrrolidinyl-oxy)imino, 3-azetidinyloxyimino, 3α-[3-(S)-pyrrolidinylthio], 3α-[3-(R)-pyrrolidinylthio], 3α-[3-(RS)-pyrrolidinylthio], 3α-[2-(pyrrolidin-3-

(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl].

Preferred examples of specific compounds (I) of the present invention are:
EZ 3-(R-3-pyrrolidinyloxy)imino-6-methyleneandrostane-17-one,
EZ 3-(S-3-pyrrolidinyloxy)imino-6-methyleneandrostane-17-one,
EZ 3-(RS-3-pyrrolidinyloxy)imino-6-methyleneandrostane-17-one,
EZ 3-(3-azetidinyloxyimino)-6-methyleneandrostane-17-one,
3α-[3-(S)-pyrrolidinylthio]-6-methyleneandrostane-17-one,
3α-[3-(R)-pyrrolidinylthio]-6-methyleneandrostane-17-one,
3α-[2-(RS)-pyrrolidinylthio]-6-methyleneandrostane-17-one,
3α-[2-(pyrrolidin-3-(R)-yl)-(Z)-vinyl]-6-methyleneandrostane-17-one,
3α-[2-(pyrrolidin-3-(S)-yl)-(Z)-vinyl]-6-methyleneandrostane-17-one,
3α-[2-(azetidin-3-yl)-(Z)-vinyl]-6-methyleneandrostane-17-one,
3α-[2-(piperidin-4-yl)-(Z)-vinyl]-6-methyleneandrostane-17-one,
and the corresponding 6-oxo, 6-difluoromethylene, 6-hydroxyimino and 6-methoxyimino derivatives;
EZ 3-(R-3-pyrrolidinyloxy)imino-6α-methylandrostane-17-one,
EZ 3-(S-3-pyrrolidinyloxy)imino-6α-methylandrostane-17-one,
EZ 3-(RS-3-pyrrolidinyloxy)imino-6α-methylandrostane-17-one,
EZ 3-(3-azetidinyloxyimino)-6α-methylandrostane-17-one,
3α-[3-(S)-pyrrolidinylthio]-6α-methylandrostane-17-one,
3α-[3-(R)-pyrrolidinylthio]-6α-methylandrostane-17-one,
3α-[3-(RS)-pyrrolidinylthio]-6α-methylandrostane-17-one,
3α-[2-(pyrrolidin-3-(R)-yl)-(Z)-vinyl]-6α-methylandrostane-17-one,
3α-[2-(pyrrolidin-3-(S)-yl)-(Z)-vinyl]-6α-methylandrostane-17-one,
3α-[2-(azetidin-3-yl)-(Z)-vinyl]-6α-methylandrostane-17-one,
3α-[2-(piperidin-4-yl)-(Z)-vinyl]-6α-methylandrostane-17-one,
and the corresponding 6α-hydroxy, 6α-carbamoyl, 6α-methoxycarbonyl, 6α-hydroxymethyl, 6α-(2-hydroxyethyl), 6α-methoxymethyl, 6α-nitroxy, 6α-formylamino, 6α-ethynyl, 6β-hydroxy derivatives;
EZ 3-(R-3-pyrrolidinyloxy)imino-5α-hydroxy-6-methyleneandrostan-17-one,
EZ 3-(S-3-pyrrolidinyloxy)imino-5α-hydroxy-6-methyleneandrostan-17-one,
EZ 3-(RS-3-pyrrolidinyloxy)imino-5α-hydroxy-6-methyleneandrostan-17-one,
EZ 3-(3-azetidinyloxyimino)-5α-hydroxy-6-methyleneandrostan-17-one,
3α-[3-(S)-pyrrolidinylthio]-5α-hydroxy-6-methyleneandrostane-17-one,
3α-[3-(R)-pyrrolidinylthio]-5α-hydroxy-6-methyleneandrostane-17-one,
3α-[3-(RS)-pyrrolidinylthio]-5α-hydroxy-6-methyleneandrostane-17-one,
3α-[2-(pyrrolidin-3-(R)-yl)-(Z)-vinyl]-5α-hydroxy-6-methyleneandrostane-17-one,
3α-[2-(pyrrolidin-3-(S)-yl)-(Z)-vinyl]-5α-hydroxy-6-methyleneandrostane-17-one,
3α-[2-(azetidin-3-yl)-(Z)-vinyl]-5α-hydroxy-6-methyleneandrostane-17-one,
3α-[2-(piperidin-4-yl)-(Z)-vinyl]-5α-hydroxy-6-methyleneandrostane-17-one,
and the corresponding 6-oxo, 6-difluoromethylene, 6-hydroxyimino and 6-methoxyimino derivatives;
EZ 3-(R-3-pyrrolidinyloxy)imino-5α-hydroxy-6α-methylandrostan-17-one,
EZ 3-(S-3-pyrrolidinyloxy)imino-5α-hydroxy-6α-methylandrostan-17-one,
EZ 3-(RS-3-pyrrolidinyloxy)imino-5α-hydroxy-6α-methylandrostan-17-one,
EZ 3-(3-azetidinyloxyimino)-5α-hydroxy-6α-methylandrostan-17-one,
3α-[3-(S)-pyrrolidinylthio]-5α-hydroxy-6α-methylandrostane-17-one,
3α-[3-(R)-pyrrolidinylthio]-5α-hydroxy-6α-methylandrostane-17-one,
3α-[3-(RS)-pyrrolidinylthio]-5α-hydroxy-6α-methylandrostane-17-one,
3α-[2-(pyrrolidin-3-(R)-yl)-(Z)-vinyl]-5α-hydroxy-6α-methylandrostane-17-one,
3α-[2-(pyrrolidin-3-(S)-yl)-(Z)-vinyl]-5α-hydroxy-6α-methylandrostane-17-one,
3α-[2-(azetidin-3-yl)-(Z)-vinyl]-5α-hydroxy-6α-methylandrostane-17-one,
3α-[2-(piperidin-4-yl)-(Z)-vinyl]-5α-hydroxy-6α-methylandrostane-17-one,
and the corresponding 6α-carbamoyl, 6α-methoxycarbonyl, 6α-hydroxymethyl, 6α-methoxymethyl, 6α-nitroxy, 6α-formylamino, 6α-ethynyl derivatives;
EZ 3-(R-3-pyrrolidinyloxy)imino-7-methyleneandrostan-17-one,
EZ 3-(S-3-pyrrolidinyloxy)imino-7-methyleneandrostan-17-one,
EZ 3-(RS-3-pyrrolidinyloxy)imino-7-methyleneandrostan-17-one,
EZ 3-(3-azetidinyloxyimino)-7-methyleneandrostan-17-one,
3α-[3-(S)-pyrrolidinylthio]-7-methyleneandrostane-17-one,
3α-[3-(R)-pyrrolidinylthio]-7-methyleneandrostane-17-one,
3α-[3-(RS)-pyrrolidinylthio]-7-methyleneandrostane-17-one,
3α-[2-(pyrrolidin-3-(R)-yl)-(Z)-vinyl]-7-methyleneandrostane-17-one,
3α-[2-(pyrrolidin-3-(S)-yl)-(Z)-vinyl]-7-methyleneandrostane-17-one,
3α-[2-(azetidin-3-yl)-(Z)-vinyl]-7-methyleneandrostane-17-one,
3α-[2-(piperidin-4-yl)-(Z)-vinyl]-7-methyleneandrostane-17-one,
and the corresponding 7-oxo, 7-difluoromethylene, 7-hydroxyimino and 7-methoxyimino derivatives;
EZ 3-(R-3-pyrrolidinyloxy)imino-7α-methylandrostan-17-one,
EZ 3-(S-3-pyrrolidinyloxy)imino-7α-methylandrostan-17-one,
EZ 3-(RS-3-pyrrolidinyloxy)imino-7α-methylandrostan-17-one,
EZ 3-(3-azetidinyloxyimino)-7α-methylandrostan-17-one,
3α-[3-(S)-pyrrolidinylthio]-7α-methylandrostane-17-one,
3α-[3-(R)-pyrrolidinylthio]-7α-methylandrostane-17-one,
3α-[3-(RS)-pyrrolidinylthio]-7α-methylandrostane-17-one,
3α-[2-(pyrrolidin-3-(R)-yl)-(Z)-vinyl]-7α-methylandrostane-17-one,
3α-[2-(pyrrolidin-3-(S)-yl)-(Z)-vinyl]-7α-methylandrostane-17-one, 3α-[2-(azetidin-3-yl)-(Z)-vinyl]-7α-methylandrostane-17-one,
3α-[2-(piperidin-4-yl)-(Z)-vinyl]-7α-methylandrostane-17-one,
and the corresponding 7α-hydroxy, 7α-carbamoyl, 7α-methoxycarbonyl, 7α-hydroxymethyl, 7α-methoxymethyl, 7α-nitroxy, 7α-formylamino, 7α-ethynyl and 7β-hydroxy, 7β-methyl, 7β-carbamoyl, 7β-methoxycarbonyl, 7β-hydroxymethyl, 7β-methoxymethyl, 7β-nitroxy, 7β-formylamino, 7β-ethynyl derivatives;
EZ 3-(R-3-pyrrolidinyloxy)imino-5α-hydroxy-7-methyleneandrostan-17-one,
EZ 3-(S-3-pyrrolidinyloxy)imino-5α-hydroxy-7-methyleneandrostan-17-one,
EZ 3-(RS-3-pyrrolidinyloxy)imino-5α-hydroxy-7-methyleneandrostan-17-one,
EZ 3-(3-azetidinyloxyimino)-5α-hydroxy-7-methyleneandrostan-17-one,
3α-[3-(S)-pyrrolidinylthio]-5α-hydroxy-7-methyleneandrostane-17-one,
3α-[3-(R)-pyrrolidinylthio]-5α-hydroxy-7-methyleneandrostane-17-one,
3α-[3-(RS)-pyrrolidinylthio]-5α-hydroxy-7-methyleneandrostane-17-one,
3α-[2-(pyrrolidin-3-(R)-yl)-(Z)-vinyl]-5α-hydroxy-7-methyleneandrostane-17-one,
3α-[2-(pyrrolidin-3-(S)-yl)-(Z)-vinyl]-5α-hydroxy-7-methyleneandrostane-17-one,
3α-[2-(azetidin-3-yl)-(Z)-vinyl]-5α-hydroxy-7-methyleneandrostane-17-one,
3α-[2-(piperidin-4-yl)-(Z)-vinyl]-5α-hydroxy-7-methyleneandrostane-17-one,
and the corresponding 7-hydroxyimino and 7-methoxyimino derivatives;
EZ 3-(R-3-pyrrolidinyloxy)imino-5α-hydroxy-7α-methylandrostan-17-one,
EZ 3-(S-3-pyrrolidinyloxy)imino-5α-hydroxy-7α-methylandrostan-17-one,
EZ 3-(RS-3-pyrrolidinyloxy)imino-5α-hydroxy-7α-methylandrostan-17-one,
EZ 3-(3-azetidinyloxyimino)-5α-hydroxy-7α-methylandrostan-17-one,
3α-[3-(S)-pyrrolidinylthio]-5α-hydroxy-7α-methylandrostane-17-one,
3α-[3-(R)-pyrrolidinylthio]-5α-hydroxy-7α-methylandrostane-17-one,
3α-[3-(RS)-pyrrolidinylthio]-5α-hydroxy-7α-methylandrostane-17-one,
3α-[2-(pyrrolidin-3-(R)-yl)-(Z)-vinyl]-5α-hydroxy-7α-methylandrostane-17-one,
3α-[2-(pyrrolidin-3-(S)-yl)-(Z)-vinyl]-5α-hydroxy-7α-methylandrostane-17-one,
3α-[2-(azetidin-3-yl)-(Z)-vinyl]-5α-hydroxy-7α-methylandrostane-17-one,
3α-[2-(piperidin-4-yl)-(Z)-vinyl]-5α-hydroxy-7α-methylandrostane-17-one,
and the corresponding 7α-carbamoyl, 7α-methoxycarbonyl, 7α-hydroxymethyl, 7α-methoxymethyl, 7α-nitroxy, 7α-formylamino, 7α-ethynyl and 7β-carbamoyl, 7β-methoxycarbonyl, 7β-hydroxymethyl, 7β-methoxymethyl, 7β-nitroxy, 7β-formylamino, 7β-ethynyl derivatives;
EZ 3-(R-3-pyrrolidinyloxy)imino-5α-hydroxyandrostan-17-one,
EZ 3-(S-3-pyrrolidinyloxy)imino-5α-hydroxyandrostan-17-one,
EZ 3-(RS-3-pyrrolidinyloxy)imino-5α-hydroxyandrostan-17-one,
EZ 3-(3-azetidinyloxyimino)-5α-hydroxyandrostan-17-one,
3α-[3-(S)-pyrrolidinylthio]-5α-hydroxyandrostane-17-one,
3α-[3-(R)-pyrrolidinylthio]-5α-hydroxyandrostane-17-one,
3α-[3-(RS)-pyrrolidinylthio]-5α-hydroxyandrostane-17-one,
3α-[2-(pyrrolidin-3-(R)-yl)-(Z)-vinyl]-5α-hydroxyandrostane-17-one,
3α-[2-(pyrrolidin-3-(S)-yl)-(Z)-vinyl]-5α-hydroxyandrostane-17-one,
3α-[2-(azetidin-3-yl)-(Z)-vinyl]-5α-hydroxyandrostane-17-one,
3α-[2-(piperidin-4-yl)-(Z)-vinyl]-5α-hydroxyandrostane-17-one,
EZ 3-(R-3-pyrrolidinyloxy)imino-6α-hydroxymethylandrostane-7,17-dione,
EZ 3-(S-3-pyrrolidinyloxy)imino-6α-hydroxymethylandrostane-7,17-dione,
EZ 3-(RS-3-pyrrolidinyloxy)imino-6α-hydroxymethylandrostane-7,17-dione,
EZ 3-(3-azetidinyloxyimino)-6α-hydroxymethylandrostane-7,17-dione,
3α-[3-(S)-pyrrolidinylthio]-6α-hydroxymethylandrostane-7,17-dione,
3α-[3-(R)-pyrrolidinylthio]-6α-hydroxymethylandrostane-7,17-dione,
3α-[3-(RS)-pyrrolidinylthio]-6α-hydroxymethylandrostane-7,17-dione,
3α-[2-(pyrrolidin-3-(R)-yl)-(Z)-vinyl]-6α-hydroxymethylandrostane-7,17-dione,
3α-[2-(pyrrolidin-3-(S)-yl)-(Z)-vinyl]-6α-hydroxymethylandrostane-7,17-dione,
3α-[2-(azetidin-3-yl)-(Z)-vinyl]-6α-hydroxymethylandrostane-7,17-dione,
3α-[2-(piperidin-4-yl)-(Z)-vinyl]-6α-hydroxymethylandrostane-7,17-dione,
EZ 3-(R-3-pyrrolidinyloxy)imino-6α-hydroxymethyl-7α-hydroxyandrostane-17-one,
EZ 3-(S-3-pyrrolidinyloxy)imino-6α-hydroxymethyl-7α-hydroxyandrostane-17-one,
EZ 3-(RS-3-pyrrolidinyloxy)imino-6α-hydroxymethyl-7α-hydroxyandrostane-17-one,
EZ 3-(3-azetidinyloxyimino)-6α-hydroxymethyl-7α-hydroxyandrostane-17-one,
3α-[3-(S)-pyrrolidinylthio]-6α-hydroxymethyl-7α-hydroxyandrostane-17-one,
3α-[3-(R)-pyrrolidinylthio]-6α-hydroxymethyl-7α-hydroxyandrostane-17-one,
3α-[3-(RS)-pyrrolidinylthio]-6α-hydroxymethyl-7α-hydroxyandrostane-17-one,
3α-[2-(pyrrolidin-3-(R)-yl)-(Z)-vinyl]-6α-hydroxymethyl-7α-hydroxyandrostane-17-one,
3α-[2-(pyrrolidin-3-(S)-yl)-(Z)-vinyl]-6α-hydroxymethyl-7α-hydroxyandrostane-17-one,
3α-[2-(azetidin-3-yl)-(Z)-vinyl]-6α-hydroxymethyl-7α-hydroxyandrostane-17-one,
3α-[2-(piperidin-4-yl)-(Z)-vinyl]-6α-hydroxymethyl-7α-hydroxyandrostane-17-one,
and the corresponding pure E and Z isomers of the EZ mixtures reported above.

The invention furthermore provides a process for the preparation of compounds of general formula (I) starting from compounds of general formula (II)

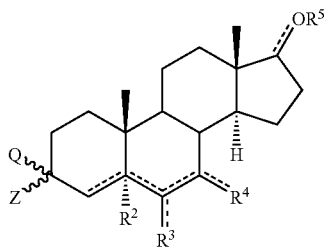
(II)

where the symbols $R^2$, $R^3$, $R^4$, $R^5$, and ----- have the meanings defined above and Q and Z represent together a keto group (=O) when the symbols ~~~ are taken together with the meaning of double bond or, when the symbols ~~~ are single bonds, Q is hydroxy, mercapto, $NHR^8$, CHO or a leaving group when Z is hydrogen, or Q is hydroxy, mercapto, $NHR^8$ when Z is $C_1$-$C_6$ straight or branched alkyl group.

Compounds of general formula (I) where the symbols $R^1$, $R^2$, $R^3$, $R^4$, $R^5$, B, Y and ----- have the meanings defined above and A is C=N~~~O can be obtained from compounds of formula (II) where Q and Z represent together a keto group (=O), when the symbols ~~~ are taken together with the meaning of double bond, by reaction with compounds of general formula (III),

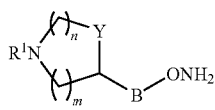
(III)

where $R^1$, B, Y, m and n have the meanings defined above, in the form of the free base or of a salt, such as, for example, dihydrochloride, in a solvent such as dioxane, tetrahydrofuran, 1,2-dimethoxyethane, methanol, ethanol, N,N-dimethylformamide, water or their mixtures, at a temperature ranging from 0° C. and the reflux temperature. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (I) where the symbols $R^1$, $R^2$, $R^3$, $R^4$, $R^5$, B, Y and ----- have the meanings defined above and A is $CR^6$~~~CH=CH~~~, $CR^6$~~~$CH_2$, where $R^6$ is hydroxy, can be obtained from compounds of formula (II) where Q and Z represent together a keto group (=O), when the symbols ~~~ are taken together with the meaning of double bond, by reaction with compounds of general formula (IV) and (V)

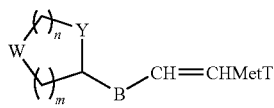
(IV)

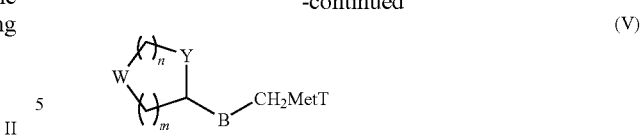
(V)

where B, Y, m, and n have the meanings defined above, Met is a metal atom and T is nothing, halogen or a different metal atom depending on the oxidation state of the Met metal atom, such as, for example, Li, MgCl, MgBr, MgI, and CuLi and W is RIN or PGN, where $R^1$ is straight or branched alkyl or phenylalkyl, and PG is a protective group, such as, for example, benzyl, Boc, Cbz, acetyl, to give compounds of general formula (I) directly or after transformation of the protecting group. The organometallic reaction can be carried out in a solvent such as dioxane, tetrahydrofuran, 1,2-dimethoxyethane, diethyl ether, hexane, toluene or their mixtures, at a temperature ranging from −70° C. and the reflux temperature. The reaction can be carried out in the presence of transition metal salts, such as, for example, $Li_2CuCl_4$, $CeCl_3$.

When W contains a protective group, the protective group can be removed after the organometallic reaction according to well established procedures described in organic chemistry, to give compounds of general formula (I).

Compounds of general formula (I) where the symbols $R^1$, $R^2$, $R^3$, $R^4$, $R^5$, B, Y and ----- have the meanings defined above and A is CH~~~X, where X is $NR^8$, can be obtained from compounds of formula (II) where Q and Z represent together a keto group (=O) when the symbols ~~~ are taken together with the meaning of double bond by reaction with compounds of general formula (VI),

(VI)

where W is $R^1N$ or PGN, and $R^1$, PG, Y, m, n, $R^8$, and B have the meanings defined above, in the form of the free base or of a salt, in a solvent such as dioxane, tetrahydrofuran, 1,2-dimethoxyethane, methanol, ethanol, N,N-dimethylformamide, water or their mixtures, at a temperature ranging from 0° C. and the reflux temperature, in the presence of a reducing agent, such as, for example, sodium borohydride or sodium cyanoborohydride. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate, until the desired pH is reached.

Compounds of general formula (I) where the symbols $R^1$, $R^2$, $R^3$, $R^4$, $R^5$, B, Y and ----- have the meanings defined above and A is CH~~~X, where X is O, S or $NR^8$, can be obtained from compounds of formula (II) where Q is hydroxy, mercapto, $NHR^8$, when Z is hydrogen by reaction with compounds of general formula (VII),

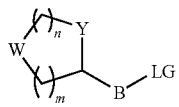

(VII)

where W is $R^1N$ or PGN, and $R^1$, Y, m, n, and B are as defined above, PG is a protective group, such as, for example, benzyl, Boc, Cbz, acetyl, to give compounds of general formula (I) directly or after transformation of the group PGN, and LG is a leaving group, such as, for example, chloro, bromo, iodo, mesyloxy, p-toluensulfonyloxy, trifluoromethanesulfonyloxy. The reaction can be carried out in a solvent such as diethyl ether, dioxane, tetrahydrofuran, 1,2-dimethoxyethane, N,N-dimethylformamide, dimethylsulfoxide, toluene, or their mixtures, at a temperature ranging from 0° C. and the reflux temperature. The reaction can be carried out in the presence of a base, such as, for example, sodium or potassium hydroxide, sodium or potassium carbonate, sodium or potassium hydrogencarbonate, sodium or potassium hydride, sodium or potassium methoxide, sodium or potassium tert-butoxide, and, optionally, of a salt, such as, for example, sodium or potassium iodide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

Compounds of general formula (I) where the symbols $R^1$, $R^2$, $R^3$, $R^4$, $R^5$, B, Y and ----- have the meanings defined above and A is CH〰〰 X, where X is O, S or $NR^8$, can be obtained from compounds of formula (II) where Q is a leaving group such as, for example, chloro, bromo, iodo, mesyloxy, p-toluensulfonyloxy, trifluoromethanesulfonyloxy, and Z is hydrogen, by reaction with compounds of general formula (VIII),

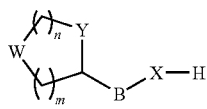

(VIII)

where W is $R^1N$, PGN, and $R^1$, Y, m, n, and B are as defined above, PG is a protective group, such as, for example, benzyl, Boc, Cbz, acetyl, and X is O, S or $NR^8$, where $R^8$ is as defined above, to give compounds of general formula (I) directly or after transformation of the group PGN. The reaction can be carried out in the same conditions reported above for the reaction of compounds of general formula (II) with compounds of general formula (VII).

Compounds of general formula (I) where the symbols $R^1$, $R^2$, $R^3$, $R^4$, $R^5$, B, Y and ----- have the meanings defined above and A is $CR^6$〰〰 CH=CH〰〰, where $R^6$ is hydrogen, can be obtained from compounds of general formula (II) where Q is CHO and Z is hydrogen, by reaction with compounds of general formula (IX),

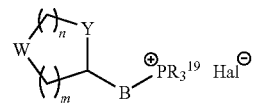

(IX)

where W is $R^1N$, PGN, and $R^1$, Y, m, n, and B are as defined above, PG is a protective group, such as, for example, benzyl, Boc, Cbz, acetyl, $R^{19}$ is a $C_1$-$C_6$ straight or branched alkyl or aryl, such as, for example, methyl, n-butyl, phenyl, o-tolyl, and Hal is a halogen, such as, for example, chloro, bromo, iodo. The reaction can be carried out in a solvent such as diethyl ether, dioxane, tetrahydrofuran, 1,2-dimethoxyethane, toluene, or their mixtures, at a temperature ranging from −78° C. and the reflux temperature. The reaction is carried out in the presence of a base, such as, for example, sodium or potassium hydride, sodium or potassium methoxide, sodium or potassium tert-butoxide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

Compounds of general formula (I) where the symbols $R^1$, $R^2$, $R^3$, $R^4$, $R^5$, B, Y and ----- have the meanings defined above and A is $CR^7$〰〰 XC=O, where $R^7$ is hydrogen or $C_1$-$C_6$ straight or branched alkyl group, X is O, S, or $NR^8$ can be obtained from compounds of formula (II) where Q is hydroxy, mercapto, $NHR^8$ and Z is hydrogen or $C_1$-$C_6$ straight or branched alkyl group by reaction with compounds of general formula (X),

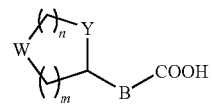

(X)

where W is $R^1N$, PGN, and $R^1$, Y, m, n, and B are as defined above, PG is a protective group, such as, for example, benzyl, Boc, Cbz, acetyl, to give compounds of general formula (I) directly or after transformation of the group PGN. The reaction can be carried out in a solvent such as diethyl ether, dioxane, tetrahydrofuran, 1,2-dimethoxyethane, toluene, acetone, ethyl acetate, dichloromethane, chloroform, N,N-dimethylformamide, dimethylsulfoxide, water or their mixtures, at a temperature ranging from −30° C. and the reflux temperature, in the presence of a condensing reagent such as, N,N'-dicyclohexylcarbodiimide, N-ethyl-N'-(3-dimethylaminopropyl)carbodiimide hydrochloride, $SOCl_2$ $POCl_3$, or $PCl_5$, or compounds of formula (X) can be treated previously with $SOCl_2$, $POCl_3$, $PCl_5$, optionally in the presence of a base, such as, for example, sodium or potassium hydroxide, sodium or potassium carbonate, sodium or potassium hydrogencarbonate, triethylamine, pyridine, or 4-dimethylaminopyridine.

Compounds of general formula (I) where the symbols $R^1$, $R^2$, $R^3$, $R^4$, $R^5$, B, Y and ----- have the meanings defined above and A is $CR^7$〰〰 X(C=O)X', where $R^7$ is hydrogen or $C_1$-$C_6$ straight or branched alkyl group, X is O, S, or $NR^8$, and X' is NH can be obtained from compounds of formula (II) where Q is hydroxy, mercapto, $NHR^8$ and Z is hydrogen or $C_1$-$C_6$ straight or branched alkyl group by reaction with compounds of general formula (XI),

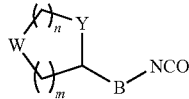
(XI)

where W is $R^1N$, PGN, and $R^1$, Y, m, n, and B are as defined above, PG is a protective group, such as, for example, benzyl, Boc, Cbz, acetyl, to give compounds of general formula (I) directly or after transformation of the group PGN. The reaction can be carried out in a solvent such as diethyl ether, dioxane, tetrahydrofuran, 1,2-dimethoxyethane, toluene, acetone, ethyl acetate, dichloromethane, chloroform, N,N-dimethylformamide, dimethylsulfoxide, ethanol, methanol, water or their mixtures, at a temperature ranging from −30° C. and the reflux temperature.

Compounds of general formula (I) where the symbols $R^1$, $R^2$, $R^3$, $R^4$, $R^5$, B, Y and ----- have the meanings defined above and A is $CR^7$∿∿∿ X(C=O)X', where $R^7$ is hydrogen or $C_1$-$C_6$ straight or branched alkyl group, X is O, S, or $NR^8$, and X' is O, S, $NR^8$ can be obtained from compounds of formula (II) where Q is hydroxy, mercapto, $NHR^8$ and Z is hydrogen or $C_1$-$C_6$ straight or branched alkyl group by reaction with compounds of general formula (XII),

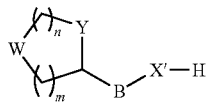
(XII)

where W is $R^1N$, PGN, and $R^1$, Y, m, n, B and X' are as defined above, PG is a protective group, such as, for example, benzyl, Boc, Cbz, acetyl, to give compounds of general formula (I) directly or after transformation of the group PGN. The reaction can be carried out in a solvent such as diethyl ether, dioxane, tetrahydrofuran, 1,2-dimethoxyethane, toluene, acetone, ethyl acetate, dichloromethane, chloroform, N,N-dimethylformamide, dimethylsulfoxide, or their mixtures, at a temperature ranging from −60° C. and the reflux temperature using a carbonyl donating group, such as, for example, carbonyldiimidazole, phosgene, triphosgene, in the presence of a base, such as, for example, sodium or potassium hydroxide, sodium or potassium carbonate, sodium or potassium hydrogencarbonate, triethylamine, pyridine, or 4-dimethylaminopyridine.

Compounds of general formula (I) where the symbols $R^1$, $R^2$, $R^3$, $R^4$, $R^5$, B, Y and ----- have the meanings defined above and A is CH∿∿∿ X, $CR^7$∿∿∿ XC=O, $CR^7$ ∿∿∿ XC(=O)X', where X and X' are $NR^8$, and $R^8$ is $C_1$-$C_6$ straight or branched alkyl group, can be obtained from compounds of formula (I) where A is CH∿∿∿ X, $CR^7$ ∿∿∿ XC=O, $CR^7$∿∿∿ XC(=O)X', where X and X' are NH, by alkylation with a $C_1$-$C_6$ alkyl-LG, where LG is a leaving group, such as, for example, chloro, bromo, iodo, mesyloxy, p-toluensulfonyloxy, trifluoromethanesulfonyloxy. The reaction can be carried out in a solvent such as diethyl ether, dioxane, tetrahydrofuran, 1,2-dimethoxyethane, N,N-dimethylformamide, dimethylsulfoxide, toluene, or their mixtures, at a temperature ranging from 0° C. and the reflux temperature, optionally in the presence of a base, such as, for example, sodium or potassium hydroxide, sodium or potassium carbonate, sodium or potassium hydrogencarbonate, sodium or potassium hydride, sodium or potassium methoxide, sodium or potassium tert-butoxide, and, optionally, of a salt, such as, for example, sodium or potassium iodide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

Compounds of general formula (I) where the symbols $R^1$, $R^2$, $R^3$, $R^4$, $R^5$, B, Y and ----- have the meanings defined above and A is CH∿∿∿ X, where X is $NR^8$, and $R^8$ is $C_1$-$C_6$ straight or branched alkyl group, can be obtained from compounds of formula (I) where A is CH∿∿∿ X, and X is NH, by reaction with $CH_2O$, or $C_1$-$C_5$ straight or branched alkyl-CHO in a solvent such as dioxane, tetrahydrofuran, 1,2-dimethoxyethane, methanol, ethanol, N,N-dimethylformamide, water or their mixtures, at a temperature ranging from 0° C. and the reflux temperature, in the presence of a reducing agent, such as, for example, sodium borohydride or sodium cyanoborohydride. The reaction can be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate, until the desired pH is reached.

Compounds of general formula (I) where the symbols $R^1$, $R^2$, $R^3$, $R^4$, $R^5$, B and ----- have the meanings defined above and A is CH∿∿∿ X, where X is $S(O)_x$ and x is 1 or 2, can be obtained from compounds of formula (I) where A is CH ∿∿∿ X, where X is $S(O)_x$ and x is 0, by one of the reagents reported in the literature for such a kind of oxidation, such as, for example, hydrogen peroxide, sodium metaperiodate, tert-butyl hypochlorite, sodium chlorite, sodium hypochlorite, sodium perborate, N-methylmorpholine-N-oxide and tetrapropylammonium periodate, potassium hydrogen persulfate, and peracids; according to the reaction conditions, that is temperature and equivalents of oxidant, the oxidation can give the compounds of general formula (I) above described where X is 1 or 2.

Compounds of general formula (I) where the symbols A, B, $R^1$, $R^2$, $R^3$, $R^4$, $R^5$, and Y, have the meanings defined above, and ----- is a single bond can be obtained by reduction of the corresponding compounds of general formula (I) where the symbol ----- is double bond, by catalytic hydrogenation, either with hydrogen gas or in hydrogen transfer conditions, in the presence of a metal catalyst, such as, Pd/C, $PtO_2$, Pt, Pt/C, Raney Nickel. As a hydrogen transfer reagent, ammonium formate, sodium hypophosphite or cyclohexadiene can be used. The reaction can be carried out in a solvent, such as, for example, ethanol, methanol, ethyl acetate, dioxane, tetrahydrofuran, acetic acid, N,N-dimethylformamide, water or their mixtures, at a temperature ranging from 0° C. and the reflux temperature, at a pressure ranging from atmospheric pressure to 10 atm. According to the substrate and the conditions used, the hydrogenation can selectively affect one or more double bonds.

Compounds of general formula (I) where the symbols B, $R^1$, $R^2$, $R^3$, $R^4$, $R^5$, Y, and ----- have the meanings defined above, and A is $CR^6$∿∿∿ CH=CH∿∿∿, $CR^6$∿∿∿ $CH_2$, where $R^6$ is hydrogen, can be obtained from the corresponding compounds of general formula (I) where $R^6$ is hydroxy by deoxygenation with one of the methods reported in literature for such a kind of reaction, such as, for example, reaction with thiocarbonyldiimidazole and tri-n-butylstannane, carbon disulfide in the presence of a base followed by methyl iodide and treatment with tri-n-butylstannane, $NaBH_3CN$ and $ZnI_2$, $NaBH_4$ in acetic acid.

Compounds of general formula (I) where the symbols A, B, $R^1$, $R^2$, $R^3$, $R^4$, $R^5$, Y, and ----- have the meanings defined above, $R^1$ is $C(=NR^9)NHR^{10}$, where $R^9$ and $R^{10}$ have the meanings reported above, can be obtained from the corresponding compounds of general formula (I) where $R^1$ is hydrogen, by reaction with compounds of general formula (XIII)

$$TC(=NR^9)NHR^{10} \quad (XIII)$$

where $R^9$ and $R^{10}$ have the meanings reported above and T is a leaving group, such as, for example, methylthio, 1-pyrazolyl. The reaction can be carried out in a solvent such as dioxane, tetrahydrofuran, 1,2-dimethoxyethane, methanol, ethanol, N,N-dimethylformamide, water or their mixtures, at a temperature ranging from 0° C. and the reflux temperature, optionally in the presence of a base, such as sodium or potassium hydroxide, triethylamine, diethylisopropylamine.

Compounds of general formula (I) where the symbols A, B, $R^1$, $R^2$, $R^5$, Y, and ----- have the meanings defined above, and $R^3$ and $R^4$, independently, are  $OR^{12}$ when the bonds ----- linking the carbon atom in position 6 of the androstane skeleton with $R^3$ and the carbon atom in position 7 with $R^4$, independently, are double bonds, can be obtained from the corresponding compounds of general formula (I) where $R^3$ and $R^4$, being $R^3$ and $R^4$ the same or different, are O, with the meaning of a keto group, with one of the methods reported in literature for such reactions, such as, for example, by reaction with compounds of general formula $H_2NOR^{12}$ where $R^{12}$ has the meanings defined above, in the form of the free base or of a salt, such as, for example, hydrochloride, in a solvent such as dioxane, tetrahydrofuran, 1,2-dimethoxyethane, methanol, ethanol, N,N-dimethylformamide, pyridine, water or their mixtures, at a temperature ranging from 0° C. and the reflux temperature. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (I) where the symbols A, B, $R^1$, $R^2$, $R^5$, Y, and ----- have the meanings defined above, and $R^3$ and $R^4$, independently, are $CR^{13}R^{14}$ when the bonds ----- linking the carbon atom in position 6 of the androstane skeleton with $R^3$ and the carbon atom in position 7 with $R^4$ are double bonds, can be obtained from the corresponding compounds of general formula (I) where $R^3$ and $R^4$, being $R^3$ and $R^4$ the same or different, are O, with the meaning of a keto group, with one of the methods reported in literature for such reactions, such as, for example, by reaction with compounds of general formula (XIV) or (XV),

where $R^{13}$, $R^{14}$, and $R^{19}$ are as defined above and Hal is a halogen, such as, for example, chloro, bromo, iodo. The reaction with compounds of general formula (XIV) or (XV) can be carried out in a solvent such as diethyl ether, dioxane, tetrahydrofuran, 1,2-dimethoxyethane, toluene, N,N-dimethylformamide, dimethylsulfoxide, n-pentane or their mixtures, at a temperature ranging from −78° C. and the reflux temperature. The reaction is carried out in the presence of a base, such as, for example, sodium or potassium hydride, sodium or potassium methoxide, sodium or potassium tert-butoxide. The reaction can be carried out also in a mixture of organic solvent, such as, for example, dichloromethane, chlorobenzene, toluene, hexane, pentane and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture. The reaction with compounds of general formula (XV) can be carried out also in water or in a mixture of the above mentioned solvents with water, at a temperature ranging from 0° C. and the reflux temperature. These reactions can be carried out in the presence of a base, such as, for example, sodium or potassium hydroxide, sodium or potassium hydrogencarbonate, sodium or potassium carbonate, triethylamine, diisopropylethylamine, optionally in the presence of a salt, such as lithium chloride.

Compounds of general formula (I) where the symbols A, B, $R^1$, $R^2$, $R^5$, Y, and ----- have the meanings defined above, and $R^3$ and $R^4$, independently, are $C_1$-$C_6$ straight or branched alkyl groups substituted with a hydroxy group, in particular are hydroxymethyl, when the bonds ----- linking the carbon atom in position 6 of the androstane skeleton with $R^3$ and the carbon atom in position 7 with $R^4$ are single bonds, can be obtained from the corresponding compounds of general formula (I) where $R^3$ and $R^4$, being $R^3$ and $R^4$ the same or different, are $CR^{13}R^{14}$, where $R^{13}$ and $R^{14}$ are hydrogens, when the bonds ----- linking the carbon atom in position 6 of the androstane skeleton with $R^3$ and the carbon atom in position 7 with $R^4$ are double bonds, with one of the methods reported in literature for such reactions, such as, for example, by reaction with a borane, such as, for example, borane, or its complexes with dimethylamine or dimethylsulfide, 9-borabicyclononane, diisopinocanphenylborane, diisoamylborane, in an ethereal solvent, such as, for example, diethyl ether, tetrahydrofuran, dioxane, 1,2-dimethoxyethane, followed by treatment with an alkaline aqueous hydrogen peroxide solution or sodium perborate.

With the same methods, also compounds of general formula (I) where the symbols A, B, $R^1$, $R^2$, $R^5$, Y, and ----- have the meanings defined above, and $R^3$ and $R^4$, independently, are $C_1$-$C_6$ straight or branched alkyl groups substituted with a hydroxy group, in particular are hydroxyethyl, when the bonds ----- linking the carbon atom in position 6 of the androstane skeleton with $R^3$ and the carbon atom in position 7 with $R^4$ are single bonds, can be obtained from the corresponding compounds of general formula (I) where $R^3$ and $R^4$, being $R^3$ and $R^4$ the same or different, are vinyl, when the bonds ----- linking the carbon atom in position 6 of the androstane skeleton with $R^3$ and the carbon atom in position 7 with $R^4$ are single bonds. Compounds of general formula (I) where the substituents $R^3$ and $R^4$, independently, are vinyl, when the bonds ----- linking the carbon atom in position 6 of the androstane skeleton with $R^3$ and the carbon atom in position 7 with $R^4$ are single bonds, can be obtained by reaction of compounds of general formula (I) where $R^3$ and $R^4$, independently, are CHO, with methyltriphenylphosphonium chloride or bromide or iodide by using the same reaction conditions above described involving compounds of general formula (XIV) or (XV).

Compounds of general formula (I) where the symbols A, B, $R^1$, $R^2$, $R^5$, Y, and ----- have the meanings defined above, and $R^3$ and $R^4$, independently, being $R^3$ and $R^4$ the same or different, are O, with the meaning of a keto group, when the bonds ----- linking the carbon atom in position 6 of the androstane skeleton with R³ and the carbon atom in position 7 with R⁴ are double bonds, can be obtained from the corresponding compounds of general formula (I) where R³ and R⁴, being R³ and R⁴ the same or different, are hydroxy, when the bonds ----- linking the carbon atom in position 6 of the androstane skeleton with R³ and the carbon atom in position 7 with R⁴ are single bonds, with one of the reagents reported in literature for such oxidations, such as, for example, iodoxybenzoic acid, Dess-Martin periodinane, oxalyl chloride and triethylamine, $CrO_3$ in pyridine or in sulfuric acid and acetone, pyridinium chlorochromate, pyridinium dichromate.

Compounds of general formula (II), as defined above, can be prepared starting from known compounds with proper functionality in the different positions, already reported in the literature or from commercially available compounds, such as, for example, 3β-hydroxyandrost-5-en-17-one, 3β-hydroxyandrost-5-ene-7,17-dione, following the general procedures listed below. The following list of compounds is an example, not limiting the scope of the invention, of reported methods of preparation of compounds (II): androstane-3,6,17-trione, 6α-hydroxyandrostane-3,17-dione, 6β-hydroxyandrostane-3,17-dione, 3,3:17,17-bis(ethylenedioxy) androstan-6α-ol, and 3,3:17,17-bis(ethylenedioxy) androstan-6-one reported in S. De Munari et al, *J. Med. Chem.*, 2003, 3644; 3β-acetoxyandrost-5-ene-7,17-dione in E. S. Arsenou et al., *Steroids* 68 (2003) 407-4143; 3, 3:17,17-bis(ethylendioxy)-5-androsten-7-one in Pui-Kai Li and R. W. Brueggemeier, *J. Med. Chem.* 1990, 33, 101-105.

Compounds of general formula (II), where R² and R⁴ are, independently, $C_1$-$C_6$ straight or branched alkyl, can be prepared from compounds of general formula (II), where R² and R⁴ are hydrogen and R³ is oxygen, when the symbol ----- linking R³ to the androstane skeleton is double bond, the symbol ----- linking R⁴ to the androstane skeleton is single bond and the symbols ----- in positions 4-5, 5-6, and 6-7 are single bonds, by treatment with a base, such as, for example, sodium or potassium hydride, sodium or potassium methoxide, sodium or potassium tert-butoxide, lithium diisopropylamide in a solvent such as diethyl ether, dioxane, tetrahydrofuran, 1,2-dimethoxyethane, toluene, N,N-dimethylformamide, dimethylsulfoxide or their mixtures, at a temperature ranging from –78° C. and the reflux temperature, followed by quenching with a $C_1$-$C_6$ straight or branched alkyl-LG, where LG is a leaving group, such as, for example, chloro, bromo, iodo, mesyloxy, p-toluensulfonyloxy, trifluoromethanesulfonyloxy, at a temperature ranging from –78° C. and the reflux temperature. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

By using the same reactions reported above, compounds of general formula (II), where R³ is $C_1$-$C_6$ straight or branched alkyl, can be prepared by treatment of the corresponding compounds of general formula (II), where R³ is hydrogen and R⁴ is oxygen, when the symbol ----- linking R³ to the androstane skeleton is single bond, the symbol ----- linking R⁴ to the androstane skeleton is double bond and the symbols ----- in positions 4-5, 5-6, and 6-7 are single bonds.

Compounds of general formula (II) where R² is $OR^{11}$, can be obtained by treatment of compound of general formula (II), where R² is hydroxy, when the symbols ----- in positions 4-5 and 5-6, are single bonds, with compounds of general formula $R^{11}$-LG, where LG is a leaving group, such as, for example, chloro, bromo, iodo, mesyloxy, p-toluensulfonyloxy, trifluoromethanesulfonyloxy. The reaction can be carried out in a solvent such as diethyl ether, dioxane, tetrahydrofuran, 1,2-dimethoxyethane, N,N-dimethylformamide, dimethylsulfoxide, toluene, or their mixtures, at a temperature ranging from 0° C. and the reflux temperature, optionally in the presence of a base, such as, for example, sodium or potassium hydroxide, sodium or potassium carbonate, sodium or potassium hydrogencarbonate, sodium or potassium hydride, sodium or potassium methoxide, sodium or potassium tert-butoxide, and, optionally, of a salt, such as, for example, sodium or potassium iodide. The reaction can be carried out also in a mixture of organic solvent, such as, for example, dichloromethane, chlorobenzene, toluene, hexane, and water, in the presence of sodium or potassium hydroxide and a quaternary ammonium salt, such as, for example, tetrabutylammonium chloride or bromide or iodide or hydrogensulfate, at a temperature ranging from 0° C. and the reflux temperature of the mixture.

By using the same reactions reported above, compounds of general formula (II) where R³ and R⁴ are, independently, $OR^{18}$, can be obtained by treatment of compounds of general formula (II), where R³ and R⁴ are hydroxy, when the symbols ----- in positions 4-5, 5-6, and 6-7, are single bonds, with compounds of general formula $R^{18}$-LG.

By using the same reactions reported above, compounds of general formula (II) where R⁵ is $C_1$-$C_6$ straight or branched alkyl group, can be obtained by treatment of compounds of general formula (II) where R⁵ is H, when the symbol ----- in positions 17 is single bond, with compounds of general formula $C_1$-$C_6$ straight or branched alkyl-LG.

Compounds of general formula (II) where R², R³, and R⁴ are, independently, $ONO_2$ can be obtained by treatment of compounds of general formula (II), where R², R³, and R⁴ are, independently, hydroxy, when the symbols ----- in positions 4-5, 5-6, and 6-7 are single bonds, with nitric acid in acetic anhydride or acetic acid, nitric acid and sulfuric acid in dichloromethane, nitrosyl fluoride or tetrafluoroborate in acetonitrile.

Compounds of general formula (II), where the substituents R³ and R⁴, independently, are N~~~ $OR^{12}$, where the bonds ----- linking the carbon atom in position 6 of the androstane skeleton with R³ and the carbon atom in position 7 with R⁴ are double bonds, and the symbols ----- in positions 4-5, 5-6, and 6-7 are single bonds, can be obtained by treatment of compounds of general formula (II), where R³ and R⁴ are, independently, oxygen, with the meaning of keto groups, being R³ and R⁴ the same or different, by reaction with compounds of general formula $H_2NOR^{12}$, where $R^{12}$ has the meanings defined above, in the form of the free base or of a salt, such as, for example, hydrochloride, in a solvent such as dioxane, tetrahydrofuran, 1,2-dimethoxyethane, methanol, ethanol, N,N-dimethylformamide, water or their mixtures, at a temperature ranging from 0° C. and the reflux temperature. The reaction may be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (II), where the substituents R³ and R⁴, independently, are $CR^{13}R^{14}$, and the bonds ----- linking the carbon atom in position 6 of the androstane skeleton with R³ and the carbon atom in position 7 with R⁴ are double bonds, and the symbols ----- in positions 4-5, 5-6, and 6-7 are single bonds, can be obtained by reaction of compounds of general formula (II) where $R^3$ and $R^4$ are, independently, oxygen, with the meaning of keto groups, being $R^3$ and $R^4$ the same or different, with compounds of general formula (XIV) or (XV),

$$R^{13}R^{14}CH\text{---}P^+R_3{}^{19}Hal^- \quad (XIV)$$

$$R^{13}R^{14}CH\text{---}P(\text{=}O)(OR^{19})_2 \quad (XV)$$

where $R^{13}$, $R^{14}$, and $R^{19}$ are as defined above and Hal is a halogen, such as, for example, chloro, bromo, iodo, in the same reaction conditions above described for the compounds of general formula (XIV) or (XV).

Compounds of general formula (II) where the substituents $R^3$ and $R^4$, independently, are $C_1$-$C_6$ straight or branched alkyl groups substituted with a hydroxy group, in particular are hydroxymethyl, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$, being $R^3$ and $R^4$ the same or different, are $CR^{13}R^{14}$, where $R^{13}$ and $R^{14}$ are hydrogens, when the bonds ----- linking the carbon atom in position 6 of the androstane skeleton with $R^3$ and the carbon atom in position 7 with $R^4$ are double bonds, with one of the methods reported in literature for such reactions, such as, for example, with a borane, such as, for example, borane, or its complexes with dimethylamine or dimethylsulfide, 9-borabicyclononane, diisopinocanphenylborane, diisoamylborane, in an ethereal solvent, such as, for example, diethyl ether, tetrahydrofuran, dioxane, 1,2-dimethoxyethane, followed by treatment with an alkaline aqueous hydrogen peroxide solution or sodium perborate.

With the same methods, also compounds of general formula (II) in which the substituents $R^3$ and $R^4$, independently, are $C_1$-$C_6$ straight or branched alkyl groups substituted with a hydroxy group, in particular are hydroxyethyl, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$, being $R^3$ and $R^4$ the same or different, are vinyl, when the bonds ----- linking the carbon atom in position 6 of the androstane skeleton with $R^3$ and the carbon atom in position 7 with $R^4$ are single bonds.

Compounds of general formula (II) where the substituents $R^3$ and $R^4$, independently, are vinyl, when the bonds ----- linking the carbon atom in position 6 of the androstane skeleton with $R^3$ and the carbon atom in position 7 with $R^4$ are single bonds, can be obtained by reaction of compounds of general formula (II) where $R^3$ and $R^5$, independently, are CHO, with methyltriphenylphosphonium chloride or bromide or iodide by using the same reaction conditions above described involving compounds of general formula (XIV) or (XV).

Compounds of general formula (II) where the substituents $R^3$ and $R^4$, independently, are ethynyl, when the bonds ----- linking the carbon atom in position 6 of the androstane skeleton with $R^3$ and the carbon atom in position 7 with $R^4$ are single bonds, can be obtained by reaction of compounds of general formula (II) where $R^3$ and $R^4$, independently, are CHO, with chloromethyltriphenylphosphonium chloride or bromide or iodide and n-butyllithium from −78° C. to room temperature followed by further treatment with n-butyllithium.

Compounds of general formula (II) where the substituents $R^3$ and $R^4$, independently, are $C_1$-$C_6$ straight or branched alkyl groups, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$, being $R^3$ and $R^4$ the same or different, are $CR^{13}R^{14}$, where $R^{13}$ and $R^{14}$ are hydrogen or $C_1$-$C_5$ straight or branched alkyl groups, when the bonds ----- linking the carbon atom in position 6 of the androstane skeleton with $R^3$ and the carbon atom in position 7 with $R^4$ are double bonds, with one of the methods reported in literature for such reactions, such as by catalytic hydrogenation, in the reaction conditions described above for a similar transformation of compounds of general formula (I).

Compounds of general formula (II), where $R^3$ and $R^4$, independently, are $C_1$-$C_6$ straight or branched alkyl groups, in particular methyl and ethyl, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$, being $R^3$ and $R^4$ the same or different, are hydroxymethyl and 2-hydroxyethyl with one of the methods reported in literature for such reactions, such as treatment with mesyl or tosylchloride, in the presence of a base, followed by reduction with a hydride, such as, for example, sodium borohydride or lithium aluminumhydride, or hydroxy by deoxygenation with one of the methods reported in literature for such a kind of reaction, such as, for example, reaction with thiocarbonyldiimidazole and tri-n-butylstannane, carbon disulfide in the presence of a base followed by methyl iodide and treatment with tri-n-butylstannane, $NaBH_3CN$ and $ZnI_2$, $NaBH_4$ in acetic acid.

Compounds of general formula (II), where $R^3$ and $R^4$, independently, are $COOR^{15}$, where $R^{15}$ is hydrogen, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$, being $R^3$ and $R^4$ the same or different, are hydroxymethyl, by oxidation with one of the reagents reported in literature for such oxidations, such as, for example, iodoxybenzoic acid, Dess-Martin periodinane, oxalyl chloride and triethylamine and dimethylsulfoxide in methylene chloride, $CrO_3$ in pyridine or in sulfuric acid and acetone, pyridinium chlorochromate, pyridinium dichromate, to give the intermediate aldehyde, where $R^3$ and $R^4$, independently, are CHO, followed by further oxidation to the carboxylic acid with one of the reagents reported in literature for such oxidations, such as, for example, potassium permanganate, chromic anhydride in sulfuric acid/acetone, pyridinium dichromate in N,N-dimethylformamide.

Compounds of general formula (II), where $R^3$ and $R^4$, independently, are $COOR^{15}$ or $CONR^{16}R^{17}$, where $R^{15}$ is a $C_1$-$C_6$ straight or branched alkyl group and $R^{16}$ and $R^{17}$ are as above defined, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$, being $R^3$ and $R^4$ the same or different, are COOH, by treatment with a compound of general formula $R^{15}OH$ or $HNR^{16}R^{17}$ with one of the methods reported in literature for such transformations, such as, for example, condensation in the presence of a condensing reagent such as, N,N'-dicyclohexylcarbodiimide, N-ethyl-N'-(3-dimethylaminopropyl)carbodiimide hydrochloride, $SOCl_2$ $POCl_3$, or $PCl_5$, or compounds of formula (II) can be treated previously with $SOCl_2$, $POCl_3$, $PCl_5$, optionally in the presence of a base, such as, for example, sodium or potassium hydroxide, sodium or potassium carbonate, sodium or potassium hydrogencarbonate, triethylamine, pyridine, or 4-dimethylaminopyridine.

Compounds of general formula (II), where $R^3$ and $R^4$, independently, are $CONR^{16}R^{17}$, where and $R^{16}$ and $R^{17}$ are as above defined, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$, being $R^3$ and $R^4$ the same or different, are $COOR^{15}$, where $R^{15}$ is a $C_1$-$C_6$ straight or branched alkyl group, by treatment with a compound of general formula $HNR^{16}R^{17}$ with one of the methods reported in literature for such transformations, such as, for example, in water, methanol or ethanol, eventually in the presence of a catalytic amount of sodium methoxide.

Compounds of general formula (II), where $R^3$ and $R^4$, independently, are CH=N~~~ OH, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$, being $R^3$ and $R^4$ the same or different, are CHO, by treatment with hydroxylamine as the free base or in the form of a salt, such as hydrochloride, sulfate, phosphate, in a solvent such as dioxane, tetrahydrofuran, 1,2-dimethoxyethane, methanol, ethanol, N,N-dimethylformamide, water or their mixtures, at a temperature ranging from 0° C. and the reflux temperature. The reaction can be carried out in the presence of a base, such as sodium or potassium hydroxide, sodium or potassium carbonate, sodium or potassium hydrogencarbonate, or of an acid, such as hydrochloric acid, hydrobromic acid, acetic acid, or of a salt, such as sodium or potassium acetate, sodium or potassium phosphate, disodium or dipotassium hydrogenphosphate, sodium or potassium dihydrogenphosphate.

Compounds of general formula (II), where $R^3$ and $R^4$, independently, are CN, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$ are oxygen, with the meaning of keto groups, being $R^3$ and $R^4$ the same or different, where the bonds ----- linking the carbon atom in position 6 of the androstane skeleton with $R^3$ and the carbon atom in position 7 with $R^4$ are double bonds, and the symbols ----- in positions 4-5, 5-6, and 6-7 are single bonds, with one of the methods reported in literature for such transformations, such as, for example, treatment with tosylmethyl isocyanide in the presence of a base.

Compounds of general formula (II), where $R^3$ and $R^4$, independently, are NHCHO and $NHCOCH_3$, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$ are N~~~ $OR^{12}$, where $R^{12}$ is hydrogen, being $R^3$ and $R^4$ the same or different, where the bonds ----- linking the carbon atom in position 6 of the androstane skeleton with $R^3$ and the carbon atom in position 7 with $R^4$ are double bonds, and the symbols ----- in positions 4-5, 5-6, and 6-7 are single bonds, with one of the methods reported in literature for such reductions, such as, for example, treatment with lithium aluminumhydride, catalytic hydrogenation, or sodium or lithium or magnesium in an alcohol, followed by formylation with formic acid or acetylation with acetic anhydride, optionally in the presence of a base, such as, for example, triethylamine, pyridine, or 4-dimethylaminopyridine or acetic acid in the presence of a condensing agent, such as, for example, N,N'-dicyclohexylcarbodiimide, N-ethyl-N'-(3-dimethylaminopropyl) carbodiimide hydrochloride.

Compounds of general formula (II), where $R^3$ and $R^4$, independently, are spiroxirane, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$ are $CR^{13}R^{14}$, where $R^{13}$ and $R^{14}$ are hydrogen, being $R^3$ and $R^4$ the same or different, where the bonds ----- linking the carbon atom in position 6 of the androstane skeleton with $R^3$ and the carbon atom in position 7 with $R^4$ are double bonds, and the symbols ----- in positions 4-5, 5-6, and 6-7 are single bonds, with one of the reagents reported in literature for such reactions, such as, for example perbenzoic acid, m-chloroperbenzoic acid, magnesium perphthalate, perphthalic acid, peracetic acid or hydrogen peroxide and sodium hydroxide in acetonitrile.

Compounds of general formula (II), where $R^3$ and $R^4$, independently, are spirooxirane, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$, independently, are O, with the meaning of keto groups, where the bonds ----- linking the carbon atom in position 6 the androstane skeleton with $R^3$ and the carbon atom in position 7 with $R^4$ are double bonds, being $R^3$ and $R^4$ the same or different, and the symbols ----- in positions 4-5, 5-6, and 6-7 are single bonds, with one of the reagents reported in literature for such reactions, such as, for example trimethylsulfonium iodide or trimethylsulfoxonium iodide in the presence of a base, such as sodium hydride, sodium methoxide, potassium tert-butoxide.

Compounds of general formula (II), where $R^3$ and $R^4$, independently, are spirocyclopropane, when the bonds ----- linking the carbon atom in position 6 of the androstane skeleton with $R^3$ and the carbon atom in position 7 with $R^4$ are single bonds, can be obtained from compounds of general formula (II) where $R^3$ and $R^4$ are $CR^{13}R^{14}$, where $R^{13}$ and $R^{14}$ are hydrogen, being $R^3$ and $R^4$ the same or different, where the bonds ----- linking the carbon atom in position 6 of the androstane skeleton with $R^3$ and the carbon atom in position 7 with $R^4$ are double bonds, and the symbols ----- in positions 4-5, 5-6, and 6-7 are single bonds, with one of the reagents reported in literature for such reactions, such as, for example, diiodomethane and diethyltin or tin-copper alloy.

Compounds of general formula (II) where $R^5$ is $C_2$-$C_6$ acyl group, when the bond ----- in position 17 of the androstane skeleton is a single bond, can be obtained from compounds of general formula (II) where $R^5$ is hydrogen, with one of the methods reported in literature for such reactions, such as, for example, by reaction with compounds of general formula $C_1$-$C_5$ straight or branched alkyl-COOH in the presence of a condensing reagent such as, N,N'-dicyclohexylcarbodiimide, N-ethyl-N'-(3-dimethylaminopropyl)carbodiimide hydrochloride, $SOCl_2$ $POCl_3$, or $PCl_5$, or compounds of formula $C_1$-$C_5$ straight or branched alkyl-COOH can be treated previously with $SOCl_2$, $POCl_3$, $PCl_5$, optionally in the presence of a base, such as, for example, sodium or potassium hydroxide, sodium or potassium carbonate, sodium or potassium hydrogencarbonate, triethylamine, pyridine, or 4-dimethylamino-pyridine.

Compounds of general formula (II) where Q is mercapto, where the symbols $R^2$, $R^3$, $R^4$, $R^5$, and ----- have the meanings defined above and Z is hydrogen or $C_1$-$C_6$ straight or branched alkyl group, can be obtained from compounds of general formula (II) where Q is hydroxy, with one of the methods reported in literature for such reactions, such as, for example, by reaction with thiocarboxylic acids, such as thioacetic acid, in the presence of diethyl or diisopropyl azodicarboxylate and tributylphosphine or triphenylphosphine, followed by cleavage of the thioester group with ammonia, sodium methanethiolate or propanethiolate.

Compounds of general formula (II) where Q is $NHR^8$, where the symbols $R^2$, $R^3$, $R^4$, $R^5$, $R^8$, and ----- have the meanings defined above and Z is hydrogen, can be obtained from compounds of general formula (II) where Q and Z represent together a keto group (=O), when the symbols ∿∿ are taken together with the meaning of double bond, with one of the methods reported in literature for such reactions, such as, for example, by reaction with compounds of general formula $NH_2R^8$ in the presence of a reducing agent, such as, for example, sodium borohydride or sodium cyanoborohydride at the appropriate pH.

Compounds of general formula (II) where Q is $NHR^8$, where the symbols $R^2$, $R^3$, $R^4$, $R^5$, and ----- have the meanings defined above, $R^8$ is hydrogen and Z is hydrogen, can be obtained from compounds of general formula (II) where Q and Z represent together a keto group (=O), when the symbols ∿∿ are taken together with the meaning of double bond, with one of the methods reported in literature for such reactions, such as, for example, by reaction with compounds of general formula $HONH_2$ to give the oxime followed by reduction with a reducing agent, such as, for example, sodium in an alcohol, lithium aluminumhydride, or by hydrogenation over a metal catalyst, such as, for example, Pt, Pd or Raney Nickel.

Compounds of general formula (II) where Q is CHO, where the symbols $R^2$, $R^3$, $R^4$, $R^5$, and ----- have the meanings defined above and Z is hydrogen, can be obtained from compounds of general formula (II) where Q and Z represent together a keto group (=O), when the symbols ∿∿ are taken together with the meaning of double bond, with one of the methods reported in literature for such reactions, such as, for example, by reaction with methoxymethyl triphenylphosphonium chloride in the presence of a strong base, such as, for example, sodium hydride or potassium tert-butoxide, followed by acidic hydrolysis of the intermediate methyl enolether; by reaction with trimethylsulfonium iodide or trimethylsulfoxonium iodide in the presence of a base, such as sodium hydride, sodium methoxide, potassium tert-butoxide followed by treatment with boron trifluoride etherate; by reaction with methyltriphenylphosphonium iodide in the presence of a base, such as sodium hydride, sodium methoxide, potassium tert-butoxide, to give the methylene derivative, which on treatment with borane and sodium perborate or alkaline hydrogen peroxide gives the hydroxymethyl derivative, which can be oxidized to the desired carboxaldehyde with one of the reagents reported in literature for such oxidations, such as, for example, iodoxybenzoic acid, Dess-Martin periodinane, oxalyl chloride and triethylamine, $CrO_3$ in pyridine or in sulfuric acid and acetone, pyridinium chlorochromate, pyridinium dichromate.

Compounds of general formula (II) where Q is hydroxy, where the symbols $R^2$, $R^3$, $R^4$, $R^5$, and ----- have the meanings defined above and Z is $C_1$-$C_6$ straight or branched alkyl group can be obtained from compounds of general formula (II) where Q and Z represent together a keto group (=O), when the symbols ∿∿ are taken together with the meaning of double bond, with one of the methods reported in literature for such reactions, such as, for example, by reaction with a compound of general formula $C_1$-$C_6$ alkylMetT, where Met is a metal atom and T is nothing, halogen or a different metal atom depending on the oxidation state of the Met metal atom, such as, for example, Li, MgCl, MgBr, MgI, and CuLi.

Compounds of general formula (II) where Q is $NHR^8$, where the symbols $R^2$, $R^3$, $R^4$, $R^5$, and ----- have the meanings defined above, $R^8$ is hydrogen and Z is $C_1$-$C_6$ straight or branched alkyl group can be obtained from compounds of general formula (II) where Q is hydroxy with one of the methods reported in literature for such reactions, such as, for example, by reaction with hydrocyanic acid in the presence of a strong acid such as, for example, sulfuric acid, followed by hydrolysis of the intermediate formamide.

Compounds of general formula (III)-(XV) are commercially available or can be prepared from commercially available compounds by standard procedures.

In all said transformations, any interfering reactive group can be protected and then deprotected according to well established procedures described in organic chemistry (see for example: T. W. Greene and P. G. M. Wuts "Protective Groups in Organic Synthesis", J. Wiley & Sons, Inc., $3^{rd}$ Ed., 1999) and well known to those skilled in the art.

All said transformations are only examples of well established procedures described in organic chemistry (see for example: J. March "Advanced Organic Chemistry", J. Wiley & Sons, Inc., $4^{th}$ Ed., 1992) and well known to those skilled in the art.

The compounds of formula (I) as defined above are useful agents for the treatment of cardiovascular disorders, such as heart failure and hypertension. Moreover said compounds show affinity and inhibit the enzymatic activity of the $Na^+$, $K^+$-ATPase.

Since the compounds of the present invention are shown to be able to antagonize the molecular effects induced by nanomolar ouabain concentrations on the Na-KATPase, they will be effective the treatment of the diseases caused by the hypertensive effects of endogenous ouabain.

According to a preferred embodiment of the invention the diseases caused by the hypertensive effects of endogenous ouabain include: renal failure progression in autosomal dominant polycystic renal disease (ADPKD), preeclamptic hypertension and proteinuria and renal failure progression in patients with adducin polymorphisms.

In autosomal dominant polycystic renal disease (ADPKD), cyst formation and enlargement are due to cell proliferation and transepithelial secretion of fluids, causing progressive impairment renal function and kidney failure. 1 over 1000 subjects are affected by ADPKD which represents the first genetic cause of renal failure. Renal Na—K ATPase is essential for ion and fluid transport in ADPKD cells and its mislocation and function alteration have been described in this pathology (Wilson P D et al. Am J Pathol 2000; 156:253-268). Ouabain, the inhibitor of the Na-KATPase, inhibits fluid secretion in ADPKD cysts (Grantham J J et al. I Clin. Invest. 1995; 95:195-202) at micromolar concentrations, conversely, at nanomolar concentrations, which are similar to the circulating endogenous ouabain ones, ouabain stimulates ADPKD cell proliferation but does not affect normal human kidney cell growth (Nguyen A N et al. 2007; 18:46-57). It has been demonstrated that ouabain stimulates ADPKD proliferation by binding to the Na-KATPase with high affinity and triggering the activation of the MEK-ERK pathway (Nguyen A N et al. 2007; 18:46-57).

Preeclampsia is a potential devastating disorder of hypertension in pregnancy for which an effective treatment is still lacking. Elevated circulating levels of cardenolides and bufodienolides have been reported in preeclamptic patients and in rat models of the disease (Lopatin D A et al J. Hypertens. 1999; 17:1179-1187; Graves S V et al. Am Hypertens. 1995; 8:5-11; Adair C D et al. Am J Nephrol. 1996; 16:529-531). The data available suggest that in preeclampsia elevated plasma concentrations of Na—K ATPase inhibitors lead to vasoconstriction and malignant hypertension (Vu H V et al.

Am J Nephrol. 2005; 25:520-528). Recently, Digoxin-specific Fab (Digibind) have been proved to reduce blood pressure and increase natriuresis in preeclamptic patients (Pullen M A al. JPET 2004; 310:319-325).

Glomerulosclerosis-associated proteinuria is due to an impairment of the slit-pore structure formed by the podocyte foot-processes in the glomerulus. In particular, slit diaphragm proteins such as nephrin, ZO1, podocyn, synaptopodin and others, in addition to their structural functions participate in common signaling pathways regulated by Fyn a tyrosin kinase of the Src family kinases (Benzing T. J Am Soc Nephrol 2004; 15:1382-1391). Recently, a key role in the structure of the slit pore has been ascribed to beta adducin, a cytoskeletal protein under the control of Fyn (Gotoh H BBRC 2006; 346:600-605; Shima T et al. JBC 2001; 276: 42233-42240). Adducin polymorphisms joint to that of ACE have been found associated to impaired renal function in European and Chinese populations (Wang J G et al. J Mol Med 2004; 82:715-722; Wang J G et al. Am J Kidney Dis. 2001; 38: 1158-1168). Rostafuroxin and analogues, as endogenous ouabain antagonists, have been described to be able to antagonize the molecular effect of adducin polymorphism on tyrosin kinase signaling (Ferrandi M. et al. JBC, 2004; 279:33306-14; Ferrari et al. Am J Physiol Regul 2006; 290:R529-535; Ferrari P. et al. Med. Hypothes. 2007; 68:1307-1314).

Moreover the compounds of the invention possess positive inotropic features, as shown by slow intravenous infusion in anesthetized guinea pig according to Cerri (Cerri A. et al., J. Med. Chem. 2000, 43, 2332) and have a low toxicity when compared with standard cardiotonic steroids, e.g. digoxin.

The pharmaceutical compositions will contain at least one compound of Formula (I) as an active ingredient, in an amount such as to produce a significant therapeutic effect. The compositions covered by the present invention are entirely conventional and are obtained with methods which are common practice in the pharmaceutical industry, such as, for example, those illustrated in *Remington's Pharmaceutical Science Handbook*, Mack Pub. N.Y.—latest edition. According to the administration route chosen, the compositions will be in solid or liquid form, suitable for oral, parenteral or intravenous administration. The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

In keeping with another object of the present invention, the pharmaceutical compositions contain at least one formula (I) compound as the active ingredient, in an amount such as to produce a significant therapeutic effect without causing cardiovascular side effects. The compositions covered by the present invention are entirely conventional and are obtained using methods which are common practice in the pharmaceutical industry, such as are illustrated, for example, in *Remington's Pharmaceutical Science Handbook*, Mack Pub. N.Y.—latest edition. According to the administration route opted for, the compositions will be in solid or liquid form, suitable for oral, parenteral or intravenous administration. The compositions according to the present invention contain at least one pharmaceutically acceptable vehicle or excipient along with the active ingredient. They may be particularly useful coadjuvant agents in formulation, e.g. solubilising agents, dispersing agents, suspension agents and emulsifying agents.

The following examples further illustrate the invention.

EXAMPLE 1

(E) 3-(4-Piperidyl)oxyiminoandrostane-6,17-dione hydrochloride (I-aa)

To a solution of 4-piperidyloxyamine dihydrochloride (III-a, Prepn. 1, 100 mg) and $Na_2HPO_4.12H_2O$ (380 mg) in water (1.6 mL), a solution of androstane-3,6,17-trione (160 mg) in THF (3.2 mL) was added. After 2 hours at room temperature, NaCl (150 mg) was added and stirred for 15 min. The mixture was extracted with THF (2×2 mL) and the combined organic phases were washed with brine (3×3 mL), dried over $Na_2SO_4$ and evaporated to dryness. The residue was purified by flash chromatography ($SiO_2$, $CH_2Cl_2$:MeOH:$NH_3$ 9:1:0.1). To the concentrated fractions 5M HCl in EtOAc was added. After dilution with $Et_2O$, the solid was collected by filtration to give the title compound I-aa (140 mg, 60%). $^1$H-NMR (300 MHz, DMSO-$d_6$, ppm from TMS): δ 8.68 (2H, bb), 4.17 (1H, m), 3.15-2.90 (5H, m), 2.60-1.10 (23H, m), 0.79 (3H, s), 0.78 (3H, s).

EXAMPLE 2

(E,Z) 3-(3-Azetidinyl)oxyiminoandrostane-6,7-dione fumarate (I-ab)

Following the procedure described in Example 1 and starting from androstane-3,6,17-trione (950 mg) and 3-azetidinyloxyamine dihydrochloride (1'-b, Prepn. 2, 500 mg), the title compound I-ab was obtained (1.21 g, 80%) as a white solid. $^1$H-NMR (300 MHz, DMSO-$d_6$, ppm from TMS): δ 6.50 (2H, s), 4.87 (1H, m), 4.10-2.90 (5H, m), 2.50-1.20 (19H, m), 0.79 (6H, s).

EXAMPLE 3

(E) 3-[3-(RS)-Pyrrolidinyl]oxyiminoandrostane-6, 17-dione hydrochloride (I-ac)

A solution of 3-(RS)-pyrrolidinyloxyamine dihydrochloride (III-c, Prepn. 3, 227 mg) and androstane-3,6,17-trione (495 mg) in THF: water (2/1, 27 mL) was stirred for 30 min. NaCl was added and stirred till the two phases separated. After extraction of the aqueous layer with THF, the combined organic phases were washed with brine, dried and evaporated. The crude was purified by flash chromatography ($SiO_2$, $CH_2Cl_2$:MeOH:$NH_3$ 9:1:0.1). To the concentrated fractions 5M HCl in EtOAc was added. After dilution with $Et_2O$, the solid was collected by filtration to give the title compound I-ac (464 mg, 60%). $^1$H-NMR (300 MHz, DMSO-$d_6$, ppm from TMS): δ 9.59 (1H, bb), 9.41 (1H, bb), 4.74 (1H, m), 3.80-2.90 (5H, m), 2.60-1.20 (21H, m), 0.78 (6H, s).

EXAMPLE 4

(E,Z) 3-[3-(S)-Pyrrolidinyl]oxyiminoandrostane-6,7-dione hydrochloride (I-ad)

Following the procedure described in Example 1 and starting from androstane-3,6,17-trione (605 mg) and 3-(S)-pyrrolidinyloxyamine dihydrochloride (III-d, Prepn. 4, 350 mg), the title compound I-ad was obtained as a white solid from the crude after evaporation of THF, washing of the residue with EtOAc, and filtration (653 mg, 78%). $^1$H-NMR (300 MHz, DMSO-$d_6$, ppm from TMS): δ 9.23 (2H, bb), 4.74 (1H, m), 3.30-2.90 (5H, m), 2.60-1.20 (21H, m), 0.79 (3H, s), 0.78 (3H, s).

EXAMPLE 5

(E,Z) 3-[3-(R)-Pyrrolidinyl]oxyiminoandrostane-6, 17-dione hydrochloride (I-ae)

Following the procedure described in Example 1 and starting from androstane-3,6,17-trione (1.00 g) and 3-(R)-pyrrolidinyloxyamine dihydrochloride (III-e, Prepn. 5, 0.58 g), the title compound I-ae was obtained as a white solid from the crude after evaporation of THF, washing of the residue with EtOAc, and filtration (1.00 g, 72%). $^1$H-NMR (300 MHz, DMSO-$d_6$, ppm from TMS): δ 9.20 (2H, bb), 4.74 (1H, m), 3.35-2.90 (5H, m), 2.60-1.20 (21H, m), 0.79 (6H, s).

EXAMPLE 6

(E) 3-[3-(R)-Pyrrolidinyl]oxyiminoandrostane-6,7-dione hydrochloride (I-af)

(E,Z) 3-[3-(R)-Pyrrolidinyl]oxyiminoandrostane-6,17-dione hydrochloride (I-ae, Example 5, 650 mg) was suspended in EtOAc (150 mL) and stirred for 3 hrs. After filtration, the procedure was repeated on the solid to give the title compound I-af (300 mg, 46%) as a white solid. $^1$H-NMR (300 MHz, DMSO-$d_6$, ppm from TMS): δ 9.20 (2H, bb), 4.74 (1H, m), 3.30-2.90 (5H, m), 2.60-1.20 (21H, m), 0.79 (3H, s), 0.78 (3H, s).

EXAMPLE 7

(Z)-3-[3'-(R)-Pyrrolidinyl]oxyiminoandrostane-6,17-dione hydrochloride (I-ag)

The mother liquor of the first filtration reported in Example 6, was evaporated to dryness. The residue was dissolved in EtOH, filtrated on charcoal and the filtrate evaporated to dryness to give the title compound I-ag (250 mg, 38%) as a white powder. $^1$H-NMR (300 MHz, DMSO-$d_6$, ppm from TMS): δ 9.22 (2H, bb), 4.75 (1H, m), 3.30-3.15 (6H, m), 3.10 (1H, m), 2.95 (1H, m), 2.50-1.00 (18H, m), 0.76 (3H, s), 0.75 (3H, s).

EXAMPLE 8

(E,Z) 3-[2-(R)-Pyrrolidinyl]methoxyimino-androstane-6,7-dione hydrochloride (I-ah)

Following the procedure described in Example 1 and starting from androstane-3,6,17-trione (100 mg) and 2-[(R)-pyrrolidinyl]methoxyamine dihydrochloride (III-f, Prepn. 6, 150 mg), the title compound I-ah was obtained (130 mg, 57%) as a white solid. $^1$H-NMR (300 MHz, DMSO-$d_6$, ppm from TMS): δ 9.39 (1H, bb), 8.80 (1H, bb), 4.10 (2H, m), 3.70 (1H, m), 3.30-2.90 (3H, m), 2.60-1.20 (23H, m), 0.79 (6H, s).

EXAMPLE 9

(E,Z) 3-[2-(S)-Pyrrolidinyl]methoxyimino-androstane-6,7-dione hydrochloride (I-ai)

Following the procedure described in Example 1 and starting from androstane-3,6,17-trione (208 mg) and 2-[(S)-pyrrolidinyl]methoxyamine dihydrochloride (III-g, Prepn. 7, 130 mg), the title compound I-ai was obtained (172 mg, 55%), as a white solid. $^1$H-NMR (300 MHz, DMSO-$d_6$, ppm from TMS): δ 9.56 (1H, bb), 8.75 (1H, bb), 4.11 (2H, m), 3.68 (1H, m), 3.30-2.90 (3H, m), 2.60-1.20 (23H, m), 0.79 (6H, s).

EXAMPLE 10

(E) 3-[3'-(R,S)-Piperidinyl]oxyiminoandrostane-6,7-dione hydrochloride (I-aj)

Following the procedure described in Example 1 and starting from androstane-3,6,17-trione (100 mg) and 3-(RS)-piperidinyloxyamine dihydrochloride (III-h, Prepn. 8, 50 mg), the title compound I-aj was obtained (110 mg, 76%) as a white solid. $^1$H-NMR (300 MHz, DMSO-$d_6$, ppm from TMS): δ 8.68 (2H, bb), 4.21 (1H, m), 3.30-2.90 (5H, m), 2.60-1.20 (23H, m), 0.79 (6H, s).

EXAMPLE 11

(E,Z) 3-[3'-(S)-(1-Methyl)pyrrolidinyl]oxyiminoandrostane-6,17-dione hydrochloride (I-ak)

Following the procedure described in Example 1 and starting from androstane-3,6,17-trione (100 mg) and 3-(S)-(1-methyl)pyrrolidinyloxyamine dihydrochloride (III-i, Prepn. 9, 62 mg), the title compound I-ak was obtained (65 mg, 45%) as a white powder. $^1$H-NMR (300 MHz, DMSO-$d_6$, ppm from TMS): δ 4.70-4.60 (bb, 1H), 3.30-2.90 (m, 1H), 2.74 (s, 3H), 2.50-1.20 (m, 25H), 0.79 (s, 3H), 0.77 (s, 3H).

EXAMPLE 12

(E) 3-[3'-(R)-(1-Methyl)pyrrolidinyl]oxyiminoandrostane-6,17-dione (I-al)

Following the procedure described in Example 1 and starting from androstane-3,6,17-trione (300 mg) and 3-(R)-(1-methyl)pyrrolidinyloxyamine dihydrochloride (III-j, Prepn. 10, 190 mg), the title compound I-al was obtained (384 mg, 85%) as a light yellow powder. $^1$H-NMR (300 MHz, DMSO-$d_6$, ppm from TMS): δ 4.57 (1H, m), 2.90 (1H, dd), 2.60-1.00 (25H, m), 2.19 (3H, s), 0.78 (3H, s), 0.76 (3H, s).

EXAMPLE 13

(E,Z) 3-(3-(R)-Pyrrolidinyl)oxyimino-5α-hydroxyandrostane-17-one hemifumarate (I-am)

Prepared in 65% yield as described in Example 1 and starting from 5α-hydroxyandrostane-3,17-trione (II-aa, Prepn. 11) and 3-(R)pyrrolidinyloxyamine dihydrochloride (III-e, Prepn. 5). The crude product was purified by flash chromatography (SiO$_2$, CHCl$_3$/MeOH/26% NH$_4$OH 90/10/0.1). To the concentrated fractions a stoichiometric amount of fumaric acid in MeOH was added. After addition of a 1/1 mixture of EtOAc/Et$_2$O, the precipitate was filtered to give the title compound I-am. $^1$H-NMR (300 MHz, DMSO-$d_6$, ppm from TMS): δ 9.00 (3H, bb), 6.38 (2H, s), 5.01 (1H, s), 4.75 (0.5H, s), 4.68 (0.5H, s), 3.45-1.00 (27H, m), 0.97 (1.5H, s), 0.94 (1.5H, s), 0.76 (1.5H, s), 0.75 (1.5H, s).

EXAMPLE 14

(E,Z) 3-[3-(R)-Pyrrolidinyl]oxyimino-6α-hydroxyandrostan-17-one hydrochloride (I-an)

Following the procedure described in Example 1 and starting from 6α-hydroxyandrostane-3,17-dione (278 mg) and 3-(R)-pyrrolidinyloxyamine dihydrochloride (III-e, Prepn. 5, 160 mg), the title compound I-an was obtained as a white solid from the crude after evaporation of THF, washing of the residue with EtOAc containing 10% EtOH and filtration (270 mg, 70%). $^1$H-NMR (300 MHz, DMSO-$d_6$, ppm from TMS): δ 9.15 (2H, bb), 4.73 (1H, m), 4.52 (1H, d), 3.50-2.90 (6H, m), 2.60-0.60 (21H, m), 0.87 (1.5H, s), 0.85 (1.5H, s), 0.77 (3H, s).

EXAMPLE 15

(E,Z) 3-[3-(S)-Pyrrolidinyl]oxyimino-6α-hydroxyandrostan-17-one hydrochloride (I-ao)

Following the procedure described in Example 1 and starting from 6α-hydroxyandrostane-3,17-dione (209 mg) and 3-(S)-pyrrolidinyloxyamine dihydrochloride (III-d, Prepn. 4, 120 mg), the title compound I-ao was obtained as a white solid from the crude after evaporation of THF, washing of the residue with EtOAc/5% EtOH and filtration (204 mg, 70%). $^1$H-NMR (300 MHz, DMSO-$d_6$, ppm from TMS): δ 9.13 (2H, bb), 4.72 (1H, m), 4.54 (1H, d), 3.50-2.90 (6H, m), 2.60-0.60 (21H, m), 0.86 (1.5H, s), 0.85 (1.5H, s), 0.77 (3H, s).

EXAMPLE 16

(E,Z) 3-[3-(R)-Pyrrolidinyl]oxyimino-17-oxoandrostane-6α-yl nitrate hydrochloride (I-ap)

Prepared in 41% yield as described in Example 1 starting from 3,17-dioxoandrostane-6α-yl nitrate (II-ab, Prepn. 12) and 3-(R)-pyrrolidinyloxyamine dihydrochloride (III-e, Prepn. 5). $^1$H-NMR (300 MHz, DMSO-$d_6$, ppm from TMS): δ 8.96 (2H, bb), 4.99 (1H, m), 4.74 (1H, m), 3.40-2.90 (5H, m), 2.45-0.74 (21H, m), 0.99 (1.5H, s), 0.98 (1.5H, s), 0.80 (3H, s).

EXAMPLE 17

(E,Z) 3-[3-(R)-Pyrrolidinyl]oxyimino-6-methyleneandrostane-17-one hydrochloride (I-aq)

Prepared in 75% yield as described in Example 1 starting from 6-methyleneandrostane-3,17-dione (II-ac, Prepn. 13) and 3-(R)pyrrolidinyloxyamine dihydrochloride (III-e, Prepn. 5). $^1$H-NMR (300 MHz, DMSO-$d_6$, ppm from TMS): δ 9.01 (2H, bb), 4.83 (0.5H, m), 4.81 (0.5H, bs), 4.74 (1H, m), 4.50 (1H, m), 4.09 (2H, m), 3.50-0.88 (26H, m), 0.77 (3H, s), 0.76 (3H, s).

EXAMPLE 18

(E,Z) 3-[3-(R)-Pyrrolidinyl]oxyimino-6α-hydroxymethylandrostan-17-one hydrochloride (I-ar)

Following the procedure described in Example 1 and starting from 6α-hydroxymethylandrostane-3,17-dione (II-ad, Prepn. 14, 260 mg) and 3-(R)-pyrrolidinyloxyamine dihydrochloride (III-e, Prepn. 5, 149 mg), the title compound I-ar was obtained as a white solid from the crude after washing with EtOAc and Et$_2$O and filtration (190 mg, 57%). $^1$H-NMR (300 MHz, DMSO-$d_6$, ppm from TMS): δ 9.23 (2H, bb), 4.72 (1H, m), 4.37 (1H, t), 3.40-2.90 (7H, m), 2.50-0.60 (22H, m).

EXAMPLE 19

(E,Z) 3-[3-(R)-Pyrrolidinyl]oxyimino-6α-methoxymethylandrostane-17-one hydrochloride (I-as)

Prepared in 60% yield as described in Example 1 starting from 6α-methoxymethylandrostane-3,17-dione (II-ae, Prepn. 15) and 3-(R)pyrrolidinyloxyamine dihydrochloride (III-e, Prepn. 5). The crude was purified by flash chromatography (SiO$_2$, CH$_2$Cl$_2$:MeOH:NH$_3$ 9:1:0.1). Fumaric acid was added to the concentrated fractions to give the title compound I-as (0.43 g, 60%). $^1$H-NMR (300 MHz, DMSO-$d_6$, ppm from TMS): $^1$H-NMR (300 MHz, DMSO-$d_6$, ppm from TMS): δ 9.00 (3H, bb), 6.40 (2H, s), 4.71 (1H, m), 3.34-2.90 (7H, m), 3.22 (1.5H, s), 3.21 (1.5H, s), 2.44-0.59 (22H, m), 0.88 (3H, s), 0.78 (3H, s).

EXAMPLE 20

(Z,E) 3-(3-(R)-Pyrrolidinyloxyimino)-6α-carbamoylandrostane-17-one hydrochloride (I-at)

By Using the same reaction conditions described in Example 3 and starting from 6α-carbamoylandrostane-3,17-dione (I-af, Prepn. 16, 500 mg) and 3-(R)-pyrrolidinyloxyamine dihydrochloride (III-e, Prepn. 5, 262 mg). After 3 hrs the reaction mixture was concentrated to give a solid which was washed with boiling EtOAc. The solid was filtered to give, after drying, the title compound I-at (440 mg, 65%) as a white powder. $^1$H-NMR (300 MHz, DMSO-$d_6$, ppm from TMS): δ 7.57 (2H, bb), 7.38 (0.5H, bb), 7.31 (0.5H, bb), 6.92 (0.5H, bb), 6.78 (0.5H, bb), 4.62 (1H, m), 2.98 (5H, m), 2.45-0.63 (22H, m), 0.89 (3H, s), 0.78 (3H, s).

EXAMPLE 21

(Z,E) 3-(3-(R)-Pyrrolidinyloxyimino)-6α-methoxycarbonylandrostane-17-one hydrochloride (I-au)

By using the same reaction conditions described in Example 3 and starting from 6α-methoxycarbonylandrostane-3,17-dione (II-ag, Prepn. 17, 325 mg) and 3-(R)-pyrrolidinyloxyamine dihydrochloride (III-e, Prepn. 5, 167 mg). After 1 h the reaction mixture was extracted with THF. The organic layer was washed with brine, dried over Na$_2$SO$_4$ and evaporated to dryness. The resulting solid was washed with Et$_2$O and centrifuged to give, after drying, the title compound I-au (326 mg, 74%) as a white powder. $^1$H-NMR (300 MHz, DMSO-$d_6$, ppm from TMS): δ 8.88 (2H, bb), 4.72 (1H, m), 3.61 (1.5H, s), 3.60 (1.5H, s), 3.37-3.05 (4H, m), 2.99 (0.5H, m), 2.74 (0.5H, m), 2.46-0.70 (22H, m), 0.91 (1.5H, s), 0.90 (1.5H, s), 0.78 (3H, s).

EXAMPLE 22

(E,Z) 3-[3-(R)-Pyrrolidinyl]oxyimino-6(E)-hydroxyiminoandrostan-17-one hydrochloride (I-av)

Following the procedure described in Example 1 and starting from 6-(E)-hydroxyiminoandrostane-3,17-dione (II-ah, Prepn. 18, 380 mg) and 3-(R)-pyrrolidinyloxyamine dihydrochloride (III-e, Prepn. 5, 250 mg), the title compound I-av was obtained as a white solid after filtration from THF (404 mg, 77%). $^1$H-NMR (300 MHz, DMSO-$d_6$, ppm from TMS): δ 10.56 (0.5H, s), 10.52 (0.5H, s), 9.25 (2H, bb), 4.74 (1H, m), 3.40-3.00 (6H, m), 2.50-1.00 (20H, m), 0.78 (6H, s).

EXAMPLE 23

(E) 3-[3-(R)-Pyrrolidinyl]oxyimino-6α-methyland-rostane-17-one fumarate (I-aw)

Prepared in 84% yield as described in Example 1 starting from 6α-methylandrostane-3,17-dione (II-ai, Prepn. 19) and 3-(R)-pyrrolidinyloxyamine dihydrochloride (III-e, Prepn. 5). The crude product was purified by flash chromatography (SiO$_2$, CHCl$_3$/MeOH/26% NH$_4$OH 90/10/1). To the concentrated fractions a stoichiometric amount of fumaric acid in MeOH was added. After addition of a 1/1 mixture of EtOAc/Et$_2$O, the precipitate was triturated with Et$_2$O to give the title compound I-aw. $^1$H-NMR (300 MHz, DMSO-d$_6$, ppm from TMS): δ 8.50 (3H, bb), 6.41 (2H, m), 4.70 (1H, m), 3.30-2.90 (5H, m), 2.45-0.60 (22H, m), 0.88 (3H, s), 0.81 (3H, s), 0.77 (3H, s).

EXAMPLE 24

(Z) 3-[3-(R)-Pyrrolidinyl]oxyimino-6α-methyland-rostane-17-one hydrochloride (I-ax)

Prepared in 70% yield as described in Example 1 starting from 6α-methylandrostane-3,17-dione (II-ai, Prepn. 19) and 3-(R)-pyrrolidinyloxyamine dihydrochloride (III-e, Prepn. 5). The crude product was dissolved in H$_2$O and freeze-dried to give the title compound I-ax. $^1$H-NMR (300 MHz, DMSO-d$_6$, ppm from TMS): δ 9.03 (2H, bb), 4.73 (1H, m), 3.30-3.02 (5H, m), 2.45-0.56 (22H, m), 0.87 (3H, m), 0.84 (3H, s), 0.78 (3H, s).

EXAMPLE 25

(E,Z) 3-[3-(R)-Pyrrolidinyl]oxyimino-6α-formamidoandrostane-17-one hydrochloride (I-ay)

Prepared in 70% yield as described in Example 1 starting from 6α-formamidoandrostane-3,17-dione (II-aj, Prepn. 20) and 3-(R)pyrrolidinyloxyamine dihydrochloride (III-e, Prepn. 5). The crude product was dissolved in H$_2$O and freeze-dried to give the title compound I-ay. $^1$H-NMR (300 MHz, DMSO-d$_6$, ppm from TMS): δ 9.38 (3H, bb), 8.42-7.50 (2H, m), 4.76 (0.5H, m), 4.71 (0.5H, m), 3.72 (1H, m), 3.29-2.93 (5H, m), 2.44-0.61 (21H, m), 0.93 (1.5H, s), 0.92 (1.5H, s), 0.78 (3H, s).

EXAMPLE 26

(E,Z) 3-[3-(R)-Pyrrolidinyl]oxyimino-6-difluoromethyleneandrostan-17-one hydrochloride (I-az)

Prepared in 71% yield as described in Example 1 starting from 6-difluoromethyleneandrostane-3,17-dione (II-ak, Prepn. 21) and 3-(R)pyrrolidinyloxyamine dihydrochloride (III-e, Prepn. 5). The crude product was triturated with EtOAc. $^1$H-NMR (300 MHz, DMSO-d$_6$, ppm from TMS): δ 9.10 (2H, bb), 4.70 (1H, m), 3.20-2.90 (5H, m), 2.45-0.80 (21H, m), 0.89 (3H, s), 0.78 (3H, s).

EXAMPLE 27

(Z,E) 3-(3-(R)-Pyrrolidinyloxyimino)-6-(spirocyclopropane)androstane-17-one hydrochloride (I-ba)

Prepared in 91% yield as described in Example 1 starting 6-(spirocyclopropane)androstane-3,17-dione (II-al, Prepn. 22) and 3-(R)pyrrolidinyloxyamine dihydrochloride (III-e, Prepn. 5). The combined organic extracts were dried over Na$_2$SO$_4$, filtered and evaporated to dryness to give title compound I-ba. $^1$H-NMR (300 MHz, DMSO-d$_6$, ppm from TMS): δ 9.02 (2H, bb), 4.72 (1H, m), 3.30-3.04 (4H, m), 2.98 (0.5H, m), 2.63 (0.5H, m), 2.43-0.71 (21H, m), 0.96 (1.5H, s), 0.95 (1.5H, s), 0.79 (3H, s), 0.52 (1H, m), 0.43 (1H, m), 0.25 (1H, m), 0.10 (1H, m).

EXAMPLE 28

(E,Z) 3-[3'-(R)-Pyrrolidinyl]oxyimino-6α-ethynylandrostane-17-one hydrochloride (I-bb)

Following the procedure described in Example 1 and starting from 6α-ethynylandrostane-3,17-dione (II-am, Prepn. 23, 80 mg) and 3-(R)pyrrolidinyloxyamine dihydrochloride (III-e, Prepn. 5, 46 mg), the title compound I-bb was obtained (128 mg, 90%) as a white powder. $^1$H-NMR (300 MHz, DMSO-d$_6$, ppm from TMS): δ 8.98 (2H, bb), 4.75 (1H, m), 3.30-2.90 (6H, m), 2.49-0.85 (22H, m), 0.88 (1.5H, s), 0.87 (1.5H, s), 0.79 (3H, s).

EXAMPLE 29

(E,Z) 3-[3'-(R)-Pyrrolidinyl]oxyimino-6α-(2-hydroxyethyl)androstane-17-one hydrochloride (I-bc)

Following the procedure described in Example 1 and starting from 6α-(2-hydroxyethyl)androstane-3,17-dione (II-an, Prepn. 24, 310 mg) and -(R)-pyrrolidinyloxyamine dihydrochloride (III-e, Prepn. 5, 163 mg), the title compound I-bc was obtained (350 mg, 78%) as a white powder. $^1$H-NMR (300 MHz, DMSO-d$_6$, ppm from TMS): δ 8.95 (2H, bb), 4.74 (1H, bs), 4.30 (1H, t), 3.59-3.20 (8H, m), 3.15 (0.5H, m), 3.00 (0.5H, m), 2.45-0.60 (22H, m), 0.89 (1.5H, s), 0.88 (1.5H, s), 0.76 (3H, s).

EXAMPLE 30

(E,Z) 3-(3'-(R)-Pyrrolidinyloxyimino)-6-(E)-methoxyiminoandrostan-17-one hydrochloride (I-bd)

Following the procedure described in Example 1 and starting from 6-(E)-methoxyimino-androstane-3,17-dione (II-ao, Prepn. 25, 390 mg) and 3-(R)-pyrrolidinyloxyamine dihydrochloride (III-e, Prepn. 5, 206 mg), the title compound I-bd was obtained (363 mg, 70%) as a white powder. $^1$H-NMR (300 MHz, DMSO-d$_6$, ppm from TMS): δ 9.05 (bb, 2H), 4.65-4.55 (bs, 1H), 3.77 (s, 1.5H), 3.75 (s, 1.5H), 3.30-3.00 (s, 7H), 2.47-1.00 (m, 20H), 0.81 (s, 3H), 0.76 (s, 3H).

EXAMPLE 31

(E,Z) 3-[3'-(S)-Pyrrolidinyl]oxyimino-6-(E)-methoxyimino-androstane-17-one fumarate (I-be)

Prepared in 50% yield following the procedure described in Example 1 starting from 6-(E)-methoxyimino-androstane-3,17-dione (II-ao, Prepn. 25, 400 mg) and 3-(S)-pyrrolidinyloxyamine dihydrochloride (III-d, Prepn. 4, 210 mg). The crude product was purified by flash chromatography (SiO$_2$, CHCl$_3$/MeOH/26% NH$_4$OH 90/10/0.1). To the concentrated fractions the stoichiometric amount of fumaric acid in MeOH was added. After addition of a 1/1 mixture of EtOAc/Et$_2$O, the precipitate was filtered to give the title compound I-be as a white powder. $^1$H-NMR (300 MHz, DMSO-d$_6$, ppm from TMS): δ 6.41 (s, 2H), 4.82-4.75 (m, 1H), 3.75 (s, 1.5H), 3.74 (s, 1.5H), 3.30-2.90 (m, 7H), 2.40-1.00 (m, 19H), 0.76 (s, 3H), 0.75 (s, 3H).

EXAMPLE 32

(E,Z) 3-[3'-(S)-(1-Methyl)pyrrolidinyl]oxyimino-6-(E)-methoxyimino-androstane-17-one hydrochloride (I-bf)

Following the procedure described in Example 1 and starting from 6-(E)-methoxyiminoandrostane-3,17-dione (II-ao, Prepn. 25, 386 mg) and 3-(S)-(1-methyl)pyrrolidinyloxyamine dihydrochloride (III-i, Prepn. 9, 220 mg), the title compound I-bf was obtained (220 mg, 41%), after freeze-drying, as a white powder. $^1$H-NMR (300 MHz, DMSO-$d_6$, ppm from TMS): δ 4.80-4.60 (m, 1H), 4.76 (s, 1.5H), 4.75 (s, 1.5H), 3.25-3.15 (dd, 0.5H), 3.10-0.95 (dd, 0.5H), 2.75 (bs, 3H), 2.40-1.00 (m, 25H), 0.77 (s, 3H), 0.75 (s, 3H).

EXAMPLE 33

(E,Z) 3-[3'-(R)-(1-Methyl)pyrrolidinyl]oxyimino-(E)-6-methoxyiminoandrostane-17-one hydrochloride (I-bg)

Following the procedure described in Example 1 and starting from 6-(E)-methoxyiminoandrostane-3,17-dione (II-ao, Prepn. 25, 365 mg) and 3(R)-1-methyl-pyrrolidinyloxyamine dihydrochloride (III-j, Prepn. 10, 208 mg), the title compound I-bg was obtained (340 mg, 67%) as a white powder. $^1$H-NMR (300 MHz, DMSO-$d_6$, ppm from TMS): δ 10.12 (bb, 1H), 4.80-4.60 (m, 1H), 3.76 (s, 1.5H), 3.75 (s, 1.5H), 3.25-3.15 (dd, 0.5H), 3.10-2.95 (dd, 0.5H), 2.75 (s, 3H), 2.45-1.00 (m, 25H), 0.77 (s, 3H), 0.76 (s, 3H).

EXAMPLE 34

(E,Z) 3-[3'-(R)-Pyrrolidinyl]oxyimino-5α-hydroxy-6-methylenandrostane-17-one hydrochloride (I-bh)

Following the procedure described in Example 1 and starting from 5α-hydroxy-6-methyleneandrostane-3,17-dione (II-ap, Prepn. 26, 500 mg) and 3-(R)-pyrrolidinyloxyamine dihydrochloride (III-e, Prepn. 5, 280 mg), the title compound I-bh was obtained (550 mg, 80%) as a white powder. $^1$H-NMR (300 MHz, DMSO-$d_6$, ppm from TMS): δ 9.38 (2H, bb), 4.82 (1H, bs), 4.75 (1H, bs), 4.68 (1H, bs), 3.40-3.10 (6H, m), 3.15 (0.5H, m), 3.00 (0.5H, m), 2.70-1.00 (18H, m), 0.82 (3H, s), 0.75 (3H, s).

EXAMPLE 35

(Z) 3-[3'-(S)-Pyrrolidinyl]oxyimino-5α-hydroxy-6-methyleneandrostane-17-one fumarate (I-bi)

The title compound I-bi was obtained following the procedure described in Example 1 starting from 5α-hydroxy-6-methyleneandrostane-3,17-dione (I-ap, Prepn. 26, 125 mg) and 3-(S)-pyrrolidinyloxyamine dihydrochloride (III-d, Prepn. 4, 55 mg). The crude product was purified by flash chromatography (SiO$_2$, CHCl$_3$/MeOH/26% NH$_4$OH 90/10/0.1). To the concentrated less polar fractions the stoichiometric amount of fumaric acid in MeOH was added. After addition of a 1/1 mixture of EtOAc/Et$_2$O, the precipitate was filtered to give the title compound I-bi (64 mg, 40%) as a white powder. $^1$H-NMR (300 MHz, DMSO-$d_6$, ppm from TMS): δ 6.41 (s, 2H), 4.80 (1H, bs), 4.70 (2H, m), 4.63 (1H, bs), 3.35-3.20 (6H, m), 3.15 (1H, m), 2.40-1.00 (18H, m), 0.84 (3H, s), 0.75 (3H, s).

EXAMPLE 36

(E) 3-[3'-(S)-Pyrrolidinyl]oxyimino-5α-hydroxy-6-methyleneandrostane-17-one fumarate (I-bj)

Isolated from the concentrated more polar fractions after the flash chromatography described in Example 35. The stoichiometric amount of fumaric acid in MeOH was added. After addition of a 1/1 mixture of EtOAc/Et$_2$O, the precipitate was filtered to give the title compound I-bj (60 mg, 37%) as a white powder. $^1$H-NMR (300 MHz, DMSO-$d_6$, ppm from TMS): δ 6.41 (s, 2H), 4.78 (1H, bs), 4.70 (2H, m), 4.60 (1H, bs), 3.35-3.15 (6H, m), 3.02 (1H, m), 2.70-1.00 (18H, m), 0.82 (3H, s), 0.75 (3H, s).

EXAMPLE 37

(E,Z) 3-[3'-(S)-Pyrrolidinyl]oxyimino-5α-hydroxy-6-methylene-androstane-17-one fumarate (I-bk)

Isolated from the unseparated fractions of the flash chromatography described in Example 35. To the concentrated fractions a stoichiometric amount of fumaric acid in MeOH was added. After addition of a 1/1 mixture of EtOAc/Et$_2$O, the precipitate was filtered to give the title compound I-bk, after freeze-drying, as a white powder. $^1$H-NMR (300 MHz, DMSO-$d_6$, ppm from TMS): δ 6.61 (s, 2H), 4.87 (0.5H, bs), 4.84 (0.5H, bs), 4.75 (2H, m), 4.69 (0.5H, bs), 4.67 (0.5H, bs), 3.40-3.10 (6H, m), 3.15 (0.5H, m), 3.00 (0.5H, m), 2.70-1.00 (18H, m), 0.84 (1.5H, s), 0.82 (1.5H, s), 0.75 (3H, s).

EXAMPLE 38

(Z) 3-[3'-(R)-(1-Methyl)pyrrolidinyl]oxyimino-5α-hydroxy-6-methyleneandrostane-17-one fumarate (I-bl)

The title compound I-bl was prepared following the procedure described in Example 1 starting from 5α-hydroxy-6-methyleneandrostane-3,17-dione (II-ap, Prepn. 26, 70 mg) and 3-(R)-(1-methyl)pyrrolidinyloxyamine dihydrochloride (III-j, Prepn. 10, 42 mg). The crude product was purified by flash chromatography (SiO$_2$, CHCl$_3$/MeOH/26% NH$_4$OH 90/10/0.1). To the concentrated less polar fractions the stoichiometric amount of fumaric acid in MeOH was added. After addition of a 1/1 mixture of EtOAc/Et$_2$O, the precipitate was filtered to give the title compound I-bl (40 mg, 34%) as a white powder. $^1$H-NMR (300 MHz, DMSO-$d_6$, ppm from TMS): δ 6.45 (s, 2H), 4.82 (1 h, bs), 4.68 (2H, bs), 4.58 (1H, m), 3.30-3.20 (6H, m), 3.15-3.08 (1H, bs), 2.80-1.10 (18H, m), 2.26 (3H, s), 0.82 (3H, s), 0.76 (3H, s).

EXAMPLE 39

(E) 3-[3'-(R)-(1-Methyl)-pyrrolidinyl]oxyimino-5α-hydroxy-6-methyleneandrostane-17-one fumarate (I-bm)

Isolated from the concentrated more polar fractions after the flash chromatography described in Example 38. The stoichiometric amount of fumaric acid in MeOH was added. After addition of a 1/1 mixture of EtOAc/Et$_2$O, the precipitate was filtered to give the title compound I-bm (64 mg, 55%) as a white powder. $^1$H-NMR (300 MHz, DMSO-d$_6$, ppm from TMS): δ 6.45 (s, 2H), 4.81 (1H, bs), 4.65 (1H, bs), 4.60 (2H, m), 3.30-3.20 (6H, m), 2.98-2.88 (1H, m), 2.80-1.10 (18H, m), 2.24 (3H, s), 0.83 (3H, s), 0.76 (3H, s).

EXAMPLE 40

(Z) 3-[3'-(S)-(1-Methyl)pyrrolidinyl]oxyimino)-5α-hydroxy-6-methyleneandrostane-17-one fumarate (I-bn)

The title compound I-bn was prepared following the procedure described in Example 1 starting from 5α-hydroxy-6-methyleneandrostane-3,17-dione (II-ap, Prepn. 26, 100 mg) and 3-(S)-1-Methylpyrrolidinyloxyamine dihydrochloride (III-i, Prepn. 9, 60 mg). The crude product was purified by flash chromatography (SiO$_2$, CHCl$_3$/MeOH/26% NH$_4$OH 90/10/0.1). To the concentrated less polar fractions the stoichiometric amount of fumaric acid in MeOH was added. After addition of a 1/1 mixture of EtOAc/Et$_2$O, the precipitate was filtered to give the title compound I-bn (67 mg, 40%) as a white powder. $^1$H-NMR (300 MHz, DMSO-d$_6$, ppm from TMS): δ 6.52 (2H, s), 4.81 (1H, bs), 4.66 (1H, bs), 4.59 (2H, m), 3.40-3.20 (6H, m), 3.10-2.98 (1H, m), 2.80-1.10 (18H, m), 2.31 (3H, s), 0.81 (3H, s), 0.75 (3H, s).

EXAMPLE 41

(E) 3-[3'-(S)-(1-Methyl)pyrrolidinyl]oxyimino)-5α-hydroxy-6-methyleneandrostane-17-one fumarate (I-bo)

Isolated from the concentrated more polar fractions after the flash chromatography described in Example 40. The stoichiometric amount of fumaric acid in MeOH was added. After addition of a 1/1 mixture of EtOAc/Et$_2$O, the precipitate was filtered to give the title compound I-bo (70 mg, 41%). $^1$H-NMR (300 MHz, DMSO-d$_6$, ppm from TMS): δ 6.51 (2H, s), 4.82 (1H, bs), 4.67 (1H, bs), 4.61 (2H, m), 3.40-3.20 (6H, m), 3.05-3.00 (1H, bs), 2.90-1.10 (18H, m), 2.32 (3H, s), 0.79 (3H, s), 0.74 (3H, s).

EXAMPLE 42

(E,Z) 3-[3-(R)-Pyrrolidinyl]oxyimino-5α-hydroxy-6-(E)-hydroxyiminoandrostane-17-one hydrochloride (I-bp)

Prepared in 77% yield as described in Example 1 starting 5α-hydroxy-6-(E)-hydroxyiminoandrostane-3,17-dione (II-aq, Prepn. 27) and 3-(R)-pyrrolidinyloxyamine dihydrochloride (III-e, Prepn. 5). The combined organic extracts were dried over Na$_2$SO$_4$, filtered and evaporated to dryness to give title compound I-bp. $^1$H-NMR (300 MHz, DMSO-d$_6$, ppm from TMS): δ 10.67 (0.5H, s), 10.64 (0.5H, s), 9.01 (2H, bb), 5.08 (0.5H, s), 4.95 (0.5H, s), 4.73 (1H, m), 3.51-2.90 (6H, m), 2.62-1.10 (19H, m), 0.82 (3H, s), 0.76 (3H, s).

EXAMPLE 43

(E,Z) 3-[3-(S)-Pyrrolidinyl]oxyimino-5α-hydroxy-6-(E)-hydroxyiminoandrostane-17-one hydrochloride (I-bq)

Following the procedure described in Example 1 and starting from 5α-Hydroxy-6-(E)-hydroxyiminoandrostane-3,17-dione (II-aq, Prepn. 27, 100 mg) and 3-(S)-pyrrolidinyloxyamine dihydrochloride (III-d, Prepn. 4, 50 mg), the title compound I-bq was obtained (90 mg, 68%), after freeze-drying of the precipitated hydrochloride, as a white powder. $^1$H-NMR (300 MHz, DMSO-d$_6$, ppm from TMS): δ 10.72 (0.5H, bs), 10.63 (0.5H, bs), 9.02 (2H, bb), 4.85 (1H, bs), 4.73 (1H, bs), 3.35-3.10 (6H, m), 3.15 (1H, m), 2.99 (1H, m), 2.70-1.00 (17H, m), 0.84 (1.5H, s), 0.83 (1.5H, s), 0.78 (3H, s).

EXAMPLE 44

(Z) 3-[3'-(S)-(1-Methyl)pyrrolidinyl]oxyimino-5α-hydroxy-6-(E)-hydroxyiminoandrostane-17-one hemifumarate (I-br)

The title compound I-cf was obtained following the procedure described in Example 1 and starting from 5α-Hydroxy-6-(E)-hydroxyiminoandrostane-3,17-dione (II-aq, Prepn. 27, 100 mg) and 3-(S)-(1-methyl)pyrrolidinyloxyamine dihydrochloride (III-i, Prepn. 9, 55 mg). The crude product was purified by flash chromatography (SiO$_2$, CHCl$_3$/MeOH/26% NH$_4$OH 90/10/1). To the concentrated less polar fractions the stoichiometric amount of fumaric acid in MeOH was added, followed by a 1/1 mixture of EtOAc/Et$_2$O. The precipitate was filtered to give the title compound I-br (70 mg, 48%), after freeze-drying, as a white powder. $^1$H-NMR (300 MHz, dmso-d$_6$, ppm from TMS): δ 10.62 (s, 1H), 6.39 (s, 1H), 5.00 (s, 1H), 4.70-4.60 (m, 1H), 3.20-1.00 (m, 25H), 2.22 (s, 3H), 0.80 S, 3H), 0.78 (s, 3H).

EXAMPLE 45

(E) 3-[3'-(S)-(1-Methyl)pyrrolidinyl]oxyimino-5α-hydroxy-6-(E)-hydroxyiminoandrostane-17-one fumarate (I-bs)

Isolated from the concentrated more polar fractions after the flash chromatography described in Example 44. The stoichiometric amount of fumaric acid in MeOH was added, followed by a 1/1 mixture of EtOAc/Et$_2$O. The precipitate was filtered to give the title compound I-bs (50 mg, 32%), as a white solid. $^1$H-NMR (300 MHz, dmso-d$_6$, ppm from TMS): δ 10.62 (s, 1H), 6.48 (s, 2H), 5.00 (s, 1H), 4.63-4.48 (m, 1H), 3.20-1.00 (m, 25H), 2.22 (s, 3H), 0.82 (s, 3H), 0.73 (s, 3H).

EXAMPLE 46

(Z) 3-[3'-(R)-(1-Methyl)pyrrolidinyl]oxyimino-5α-hydroxy-6-(E)-hydroxyiminoandrostane-17-one fumarate (I-bt)

The title compound I-bt was obtained following the procedure described in Example 1 and starting from 5α-Hydroxy-6-(E)hydroxyiminoandrostane-3,17-dione (II-aq, Prepn. 27, 100 mg) and 3-(R)-(1-Methyl)pyrrolidinyloxyamine dihydrochloride (III-j, Prepn. 10, 55 mg). The crude product was purified by flash chromatography (SiO$_2$, CHCl$_3$/MeOH/26% NH$_4$OH 90/10/1). To the concentrated less polar fractions the stoichiometric amount of fumaric acid in MeOH was added, followed by a 1/1 mixture of EtOAc/Et$_2$O. The precipitate was filtered to give the title compound I-bt (32 mg, 20%), after freeze-drying, as a white amorphous powder. $^1$H-NMR (300 MHz, dmso-d$_6$, ppm from TMS): δ 10.58 (s, 1H), 6.52 (s, 2H), 5.20-5.10 (m, 1H), 4.65-4.55 (m, 1H), 3.20-1.00 (m, 25H), 2.32 (s, 3H), 0.82 (s, 3H), 0.75 (s, 3H).

EXAMPLE 47

(E) 3-[3'-(R)-(1-Methyl)pyrrolidinyl]oxyimino-5α-hydroxy-6-(E)-hydroxyiminoandrostane-17-one fumarate (I-bu)

Isolated from the concentrated more polar fractions after the flash chromatography described in Example 46. The stoichiometric amount of fumaric acid in MeOH was added, followed by a 1/1 mixture of EtOAc/Et$_2$O. The precipitate was filtered to give the title compound I-bu (70 mg, 44%), as a white solid. $^1$H-NMR (300 MHz, dmso-d$_6$, ppm from TMS): δ 10.63 (s, 1H), 6.51 (s, 2H), 5.10 (bs, 1H), 4.65-4.55 (m, 1H), 3.20-1.00 (m, 25H), 2.32 (s, 3H), 0.82 (s, 3H), 0.78 (s, 3H).

EXAMPLE 48

(E,Z)-3-(3'-(S)-Pyrrolidinyloxyimino)-5α-hydroxy-6-(E)-methoxyiminoandrostane-17-one fumarate (I-bv)

The title compound I-bv was obtained in 40% yield following the procedure described in Example 1 and starting from 5α-hydroxy-6-(E)methoxyiminoandrostane-3,17-dione (II-ar, Prepn. 28, 73 mg) and 3-(S)-pyrrolidinyloxyamine dihydrochloride (III-d, Prepn. 4, 37 mg). The crude product was purified by flash chromatography (SiO$_2$, CHCl$_3$/MeOH/26% NH$_4$OH 90/10/0.1). To the concentrated fractions a stoichiometric amount of fumaric acid in MeOH was added. After addition of a 1/1 mixture of EtOAc/Et$_2$O, the precipitate was filtered to give the title compound I-bv as a white powder. $^1$H-NMR (300 MHz, DMSO-d$_6$, ppm from TMS): δ 6.41 (s, 2H), 5.35 (bs, 0.5H), 5.21 (bs, 0.5H), 4.70 (bs, 1H), 3.73 (s, 1.5H), 3.71 (s, 1.5H), 3.30-2.90 (m, 7H), 2.41-1.00 (m, 18H), 0.81 (s, 3H), 0.72 (s, 3H).

EXAMPLE 49

(E,Z) 3-[3'-(R)-Pyrrolidinyl]oxyimino-5α-hydroxy-6-(E)-methoxyiminoandrostane-17-one fumarate (I-bw)

Prepared in 40% following the procedure described in Example 1 starting from 5α-hydroxy-6-(E)-methoxyiminoandrostane-3,17-dione (II-ar, Prepn. 28, 420 mg) and 3-(R)-pyrrolidinyloxyamine dihydrochloride (III-e, Prepn. 5, 210 mg). The crude product was purified by flash chromatography (SiO$_2$, CHCl$_3$/MeOH/26% NH$_4$OH 90/10/0.1). To the concentrated fractions the stoichiometric amount of fumaric acid in MeOH was added. After addition of a 1/1 mixture of EtOAc/Et$_2$O, the precipitate was filtered to give the title compound I-bw, after freeze-drying, as a white powder. $^1$H-NMR (300 MHz, DMSO-d$_6$, ppm from TMS): δ 6.41 (s, 2H), 5.30-5.20 (bs, 1H), 4.76-4.65 (m, 1H), 4.75 (s, 1.5H), 4.65 (s, 1.5H), 3.30-2.90 (m, 7H), 2.42-1.00 (m, 18H), 0.82 (s, 3H), 0.73 (s, 3H).

EXAMPLE 50

(Z) 3-[3'-(S)-(1-Methyl)pyrrolidinyl]oxyimino)-5α-hydroxy-6-(E)-methoxyiminoandrostane-17-one fumarate (I-bx)

The title compound I-bx was obtained following the procedure described in Example 1 starting from 5α-hydroxy-6-(E)methoxyiminoandrostane-3,17-dione (II-ar, Prepn. 28, 100 mg) and 3-(S)-(1-methyl)pyrrolidinyloxyamine dihydrochloride (III-i, Prepn. 9, 55 mg). The crude product was purified by flash chromatography (SiO$_2$, CHCl$_3$/MeOH/26% NH$_4$OH 90/10/0.1). To the concentrated less polar fractions the stoichiometric amount of fumaric acid in MeOH was added. After addition of a 1/1 mixture of EtOAc/Et$_2$O, the precipitate was filtered to give the title compound I-bx (49 mg, 30%) as a white powder. $^1$H-NMR (300 MHz, DMSO-d$_6$, ppm from TMS): δ 6.41 (2H, s), 5.24 (1H, bb), 4.67 (1H, m), 3.72 (3H, s), 3.15-2.75 (6H, m), 2.43 (3H, s), 2.65-1.00 (19H, m), 0.83 (3H, s), 0.75 (3H, s).

EXAMPLE 51

(E) 3-[3'(S)-(1-Methyl)-pyrrolidinyl]oxyimino)-5α-hydroxy-6-(E)-methoxyiminoandrostane-17-one fumarate (I-by)

Isolated from the concentrated more polar fractions after the flash chromatography described in Example 50. The stoichiometric amount of fumaric acid in MeOH was added. After addition of a 1/1 mixture of EtOAc/Et$_2$O, the precipitate was filtered to give the title compound I-by (50 mg, 30%) as a white powder. $^1$H-NMR (300 MHz, DMSO-d$_6$, ppm from TMS): δ 6.41 (s, 2H), 5.20 (1H, bb), 4.58 (1H, m), 3.76 (3H, s), 3.15-2.75 (6H, m), 2.33 (3H, s), 2.60-1.10 (19H, m), 0.83 (3H, s), 0.75 (3H, s).

EXAMPLE 52

(Z) 3-[3'-(R)-(1-Methyl)pyrrolidinyl]oxyimino)-5α-hydroxy-6-(E)-methoxyiminoandrostane-17-one fumarate (I-bz)

The title compound I-bz was obtained following the procedure described in Example 1 starting from 5α-hydroxy-6-(E)-methoxyiminoandrostane-3,17-dione (II-ar, Prepn. 28, 70 mg) and 3-(R)-(1-methyl)pyrrolidinyloxyamine dihydrochloride (III-j, Prepn. 10, 37 mg). The crude product was purified by flash chromatography (SiO$_2$, CHCl$_3$/MeOH/26% NH$_4$OH 90/10/0.1). To the concentrated less polar fractions the stoichiometric amount of fumaric acid in MeOH was added. After addition of a 1/1 mixture of EtOAc/Et$_2$O, the precipitate was filtered to give the title compound I-bz (40 mg, 36%) as a white powder. $^1$H-NMR (300 MHz, DMSO-d$_6$, ppm from TMS): δ 6.52 (s, 2H), 5.18 (1H, s), 4.58 (1H, m), 3.74 (3H, s), 3.30-3.20 (6H, m), 3.15-3.02 (1H, m), 2.80-1.10 (18H, m), 2.24 (3H, s), 0.82 (3H, s), 0.76 (3H, s).

EXAMPLE 53

(E) 3-[3'-(R)-(1-Methyl)-pyrrolidinyl]oxyimino)-5α-hydroxy-6-(E)-methoxyiminoandrostane-17-one fumarate (1-ca)

Isolated from the concentrated more polar fractions after the flash chromatography described in Example 52. The stoichiometric amount of fumaric acid in MeOH was added. After addition of a 1/1 mixture of EtOAc/Et$_2$O, the precipitate was filtered to give the title compound I-ca (56 mg, 50%) as a white powder. $^1$H-NMR (300 MHz, DMSO-d$_6$, ppm from TMS): δ 6.51 (s, 2H), 5.28 (1H, bb), 4.62 (1H, m), 3.78 (3H, s), 3.30-3.20 (6H, m), 3.05-2.95 (1H, m), 2.90-1.10 (18H, m), 2.32 (3H, s), 0.82 (3H, s), 0.76 (3H, s).

EXAMPLE 54

(E,Z) 3-[3-(R)-Pyrrolidinyl]oxyiminoandrostane-7,17-dione fumarate (I-cb)

Prepared in 50% yield as described in Example 1 starting from androstane-3,7,17-trione (II-as, Prepn. 29) and 3-(R)-pyrrolidinyloxyamine dihydrochloride (III-e, Prepn. 5). $^1$H-NMR (300 MHz, DMSO-$d_6$, ppm from TMS): δ 8.00 (3H, bb), 6.40 (2H, s), 4.74 (1H, m), 3.35-0.94 (26H, m), 1.13 (3H, s), 0.78 (3H, s).

EXAMPLE 55

(E,Z) 3-[3'-(S)-Pyrrolidinyl]oxyiminoandrostane-7,7-dione fumarate (I-cc)

Prepared in 82% following the procedure described in Example 1 starting from and androstane-3,7,17-trione (II-as, Prepn. 29, 122 mg) and 3-(S)-pyrrolidinyloxyamine dihydrochloride (III-d, Prepn. 4, 75 mg). The crude product was purified by flash chromatography (SiO$_2$, CHCl$_3$/MeOH/26% NH$_4$OH 90/10/0.1). To the concentrated fractions a stoichiometric amount of fumaric acid in MeOH was added. After addition of a 1/1 mixture of EtOAc/Et$_2$O, the precipitate was filtered to give the title compound I-cc as a white powder. $^1$H-NMR (300 MHz, DMSO-$d_6$, ppm from TMS): δ 6.41 (s, 2H), 5.75-5.65 (m, 1H), 3.30-3.00 (m, 6H), 2.95-2.80 (dd, 0.5H), 2.75-2.60 (dd, 0.5H), 2.45-1.05 (m, 19H), 1.12 (s, 3H), 0.78 (s, 3H).

EXAMPLE 56

(E,Z) 3-[3-(R)-Pyrrolidinyl]oxyimino-7(E)-hydroxyiminoandrostan-17-one fumarate (I-cd)

Prepared in 50% yield as described in Example 1 starting from 7-(E)hydroxyiminoandrostane-3,17-dione (II-at, Prepn. 30) and 3-(R)pyrrolidinyloxyamine dihydrochloride (III-e, Prepn. 5). $^1$H-NMR (300 MHz, DMSO-$d_6$, ppm from TMS): δ 10.39 (0.5H, s), 10.36 (0.5H, s), 8.66 (3H, bb), 6.40 (2H, s), 4.66 (1H, m), 3.20-2.78 (6H, m), 2.45-0.83 (20H, m), 1.01 (3H, s), 0.80 (3H, s).

EXAMPLE 57

(E,Z) 3-[3-(R)-Pyrrolidinyl]oxyimino-7(E)-methoxyiminoandrostan-17-one fumarate (I-ce)

Prepared in 50% yield as described in Example 1 starting from 7-(E)-methoxyiminoandrostane-3,17-dione (II-au, Prepn. 31) and 3-(R)-pyrrolidinyloxyamine dihydrochloride (III-e, Prepn. 5). $^1$H-NMR (300 MHz, DMSO-$d_6$, ppm from TMS): δ 8.00 (3H, bb), 6.40 (2H, s), 4.69 (1H, m), 3.72 (3H, s), 3.22-2.78 (6H, m), 2.61-0.87 (20H, m) 1.00 (3H, s), 0.80 (3H, s).

EXAMPLE 58

(E,Z) 3-[3'-(R)-Pyrrolidinyl]oxyimino-7-(E)-allyloxyiminoandrostane-17-one fumarate (I-cf)

Prepared in 49% yield as described in Example 1 starting from 7-(E)-allyloxyiminoandrostane-3,17-dione (II-av, Prepn. 32, 270 mg) and 3-(R)-pyrrolidinyloxyamine dihydrochloride (III-e, Prepn. 5, 133 mg). The crude product was purified by flash chromatography (SiO$_2$, CHCl$_3$/MeOH/26% NH$_4$OH 90/10/0.1). To the concentrated fractions a stoichiometric amount of fumaric acid in MeOH was added. After addition of a 1/1 mixture of EtOAc/Et$_2$O, the precipitate was filtered to give the title compound I-cf as a white powder. $^1$H-NMR (300 MHz, DMSO-$d_6$, ppm from TMS): δ 7.48 (1H, bs), 6.42 (2H, s), 6.00-5.85 (1H, m), 5.30-5.10 (2H, m), 4.70 (1H, bs), 4.45 (2H, d), 3.20-2.80 (6H, m), 2.40-1.10 (20H, m), 1.00 (3H, s), 0.81 (3H, s).

EXAMPLE 59

(E,Z) 3-[3'-(R)-Pyrrolidinyl]oxyimino-7-methyleneandrostane-17-one hydrochloride (I-cg)

Following the procedure described in Example 1 and starting from 7-methyleneandrostane-3,17-dione (II-aw, Prepn. 33, 110 mg) and 3-(R)-pyrrolidinyloxyamine dihydrochloride (III-e, Prepn. 5, 64 mg), the title compound I-cg was obtained (134 mg, 87%) as a light yellow powder. $^1$H-NMR (300 MHz, DMSO-$d_6$, ppm from TMS): δ 8.91 (2H, bb), 4.72 (2H, bs), 4.67 (1H, bs), 3.30-3.15 (6H, m), 3.00 (0.5H, m), 2.85 (0.5H, m), 2.45-1.00 (19H, m), 1.00 (1.5H, s), 0.99 (1.5H, s), 0.81 (3H, s).

EXAMPLE 60

(E,Z) 3-[3'-(R)-Pyrrolidinyl]oxyimino-7α-hydroxymethylandrostane-17-one hydrochloride (I-ch)

Following the procedure described in Example 1 and starting from 7α-hydroxymethylandrostane-3,17-dione (II-av, Prepn. 34, 90 mg) and 3-(R)-pyrrolidinyloxyamine dihydrochloride (III-e, Prepn. 5, 50 mg), the title compound I-ch was obtained (100 mg, 80%) as a white powder. $^1$H-NMR (300 MHz, DMSO-$d_6$, ppm from TMS): δ 9.08 (2H, bb), 4.72 (1H, m), 4.32 (1H, m), 3.60-3.15 (8H, m), 3.01 (0.5H, m), 2.75 (0.5H, m), 2.40-0.90 (20H, m), 0.89 (1.5H, s), 0.88 (1.5H, s), 0.76 (3H, s).

EXAMPLE 61

(E,Z) 3-[3'-(R)-Pyrrolidinyl]oxyimino-7β-hydroxymethylandrostane-17-one hydrochloride (I-ci)

Following the procedure described in Example 1 and starting from 7β-hydroxymethylandrostane-3,17-dione (II-aw, Prepn. 34, 80 mg) and 3-(R)-pyrrolidinyloxyamine dihydrochloride (III-e, Prepn. 5, 44 mg), the title compound I-ci was obtained (53 mg, 48%) as a white powder. $^1$H-NMR (300 MHz, dmso-$d_6$, ppm from TMS): δ 9.08 (2H, bb), 4.76 (1H, m), 4.40 (1H, m), 3.60-3.15 (8H, m), 3.05 (0.5H, m), 2.85 (0.5H, m), 2.40-0.90 (20H, m), 0.85 (3H, s), 0.79 (3H, s).

EXAMPLE 62

(E,Z) 3-[3'-(R)-Pyrrolidinyl]oxyimino-7α-hydroxyandrostane-17-one fumarate (I-cj)

Prepared in 41% yield as described in Example 1 starting from 7α-hydroxyandrostane-3,17-dione (II-ax, Prepn. 35, 210 mg) and 3-(R)pyrrolidinyloxyamine dihydrochloride (III-e, Prepn. 5, 120 mg). The crude product was purified by flash chromatography (SiO$_2$, CHCl$_3$/MeOH/26% NH$_4$OH 90/10/0.1). To the concentrated fractions a stoichiometric amount of fumaric acid in MeOH was added. After addition of a 1/1 mixture of EtOAc/Et$_2$O, the precipitate was filtered to give the title compound I-cj as a white powder. $^1$H-NMR (300

MHz, DMSO-$d_6$, ppm from TMS): δ 6.42 (2H, s), 4.62 (1H, bs), 4.32 (1H, bb), 3.75 (1H, m), 3.15-2.90 (5H, m), 2.40-1.00 (21H, m), 0.85 (3H, s), 0.72 (3H, s).

EXAMPLE 63

(E,Z) 3-[3'-(R)-Pyrrolidinyl]oxyimino-7α-methylandrostane-17-one hydrochloride (I-ck)

Following the procedure described in Example 1 and starting from 7α-methylandrostane-3,17-dione (II-ay, Prepn. 36, 31 mg) and 3-(R)-pyrrolidinyloxyamine dihydrochloride (III-e, Prepn. 5, 21 mg), the title compound was obtained (40 mg, 93%), after freeze-drying, as a white powder. $^1$H-NMR (300 MHz, DMSO-$d_6$, ppm from TMS): δ 8.94 (2H, bb), 4.72 (1H, m), 3.50-3.10 (6H, m), 3.01 (1H, m), 2.40-0.99 (20H, m), 0.92-0.83 (6H, m), 0.79 (3H, s).

EXAMPLE 64

(E,Z) 3-[3'-(R)-Pyrrolidinyl]oxyimino-7β-methylandrostane-17-one hydrochloride (I-cl)

Prepared in 92% yield as described in Example 1 starting from 7β-methylandrostane-3,17-dione (II-az, Prepn. 37, 512 mg) and 3-(R)pyrrolidinyloxyamine dihydrochloride (III-e, Prepn. 5, 282 mg). The organic phase was extracted with THF, washed with brine, dried over $Na_2SO_4$, filtered and evaporated to dryness to give the title compound I-cl as a white powder. $^1$H-NMR (300 MHz, DMSO-$d_6$, ppm from TMS): δ 9.08 (2H, bb), 4.71 (1H, m), 3.30-3.10 (6H, m), 3.05 (0.5H, m), 2.78 (0.5H, m), 2.40-0.90 (19H, m), 0.99 (3H, d), 0.82 (3H, s), 0.78 (3H, s), 0.80-0.70 (1H, m).

EXAMPLE 65

(E) 3-[3'-(R)-Pyrrolidinyl]oxyimino-7β-methylandrostane-17-one hydrochloride (I-cm)

Following the procedure described in Example 65 and starting from 7β-methylandrostane-3,17-dione (I-az, Prepn. 37, 90 mg) and 3-(R)pyrrolidinyloxyamine dihydrochloride (III-e, Prepn. 5, 50 mg), the title compound I-cm was obtained (46 mg, 36%), after crystallization from MeOH/EtOAc, as a white powder. $^1$H-NMR (300 MHz, DMSO-$d_6$, ppm from TMS): δ 8.94 (2H, bb), 4.72 (1H, m), 3.50-3.10 (6H, m), 3.01 (1H, m), 2.40-0.95 (20H, m), 0.98 (3H, d), 0.84 (3H, s), 0.78 (3H, s).

EXAMPLE 66

(Z) 3-[3'-(R)-Pyrrolidinyl]oxyimino-7β-methylandrostane-17-one hydrochloride (I-cn)

The title compound I-cn was obtained (50 mg, 40%) from the mother liquor of Example 65, after evaporation, trituration of the residue with EtOAc, as an off white solid. $^1$H-NMR (300 MHz, DMSO-$d_6$, ppm from TMS): δ 9.14 (2H, bb), 4.72 (1H, m), 3.45-3.05 (6H, m), 2.78 (1H, m), 2.40-0.95 (20H, m), 0.98 (3H, d), 0.84 (3H, s), 0.79 (3H, s).

EXAMPLE 67

(Z,E) 3-(3'-(R)-Pyrrolidinyloxyimino)-7-(spirocyclopropane)androstane-17-one hydrochloride (I-co)

Following the procedure described in Example 1 and starting from 7-(spirocyclopropane)androstane-3,17-dione (II-ba, Prepn. 38, 55 mg) and 3-(R)-pyrrolidinyloxyamine dihydrochloride (III-e, Prepn. 5, 30.mg), the title compound I-co was obtained (61 mg, 80%) as a white powder. $^1$H-NMR (300 MHz, DMSO-$d_6$, ppm from TMS): δ 9.02 (2H, bb), 4.71 (1H, m), 3.30-3.15 (6H, m), 3.05 (0.5H, m), 2.70 (0.5H, dd), 2.42-0.84 (19H, m), 0.93 (1.5H, s), 0.92 (1.5H, s), 0.80 (3H, s), 0.75-0.70 (2H, m), 0.62 (1H, m), 0.34 (1H, m).

EXAMPLE 68

(E,Z) 3-[3'-(R)-Pyrrolidinyl]oxyimino-7α-formamidoandrostane-17-one hydrochloride (1-cp)

Following the procedure described in Example 1 and starting from 7α-formamidoandrostane-6,17-dione (II-bb, Prepn. 39, 70 mg) and 3-(R)pyrrolidinyloxyamine dihydrochloride (III-e, Prepn. 5, 40 mg), the title compound I-cp was obtained (73 mg, 77%), after centrifugation, as a white powder. $^1$H-NMR (300 MHz, DMSO-$d_6$, ppm from TMS): δ 9.15 (2H, bb), 8.12 (1H, m), 7.98 (1H, m), 4.73 (1H, m), 4.05 (1H, m), 3.30-3.10 (6H, m), 3.05 (0.5H, m), 2.70 (0.5H, m), 2.40-1.00 (19H, m), 0.90 (1.5H, s), 0.89 (1.5H, s), 0.79 (3H, s).

EXAMPLE 69

(E) 3-[3'-(R)-Pyrrolidinyl]oxyimino-7α-methoxycarbonylandrostane-17-one hydrochloride (I-cq)

Following the procedure described in Example 1 and starting from 7α-methoxycarbonylandrostane-3,17-dione (II-bc, Prepn. 40, 60 mg) and 3-(R)-pyrrolidinyloxyamine dihydrochloride (III-e, Prepn. 5, 30 mg), the title compound I-cq was obtained (26 mg, 32%) as a white solid. $^1$H-NMR (300 MHz, dmso-$d_6$, ppm from TMS): δ 8.99 (2H, bb), 4.71 (1H, m), 3.57 (3H, s), 3.35-3.20 (6H, m), 3.15 (1H, m), 3.05 (1H, m), 2.74 (1H, m), 2.40-0.95 (18H, m), 0.89 (3H, s), 0.78 (3H, s).

EXAMPLE 70

(E,Z) 3-(3'-(R)-Pyrrolidinyloxyimino)-6-(E)-hydroxyimino-7α-hydroxyandrostane-17-one hydrochloride (I-cr)

Following the procedure described in Example 1 and starting from 6-(E)-hydroxyimino-7α-hydroxyandrostane-3,17-dione (II-bd, Prepn. 41, 83 mg) and 3-(R)-pyrrolidinyloxyamine dihydrochloride (III-e, Prepn. 5, 48 mg), the title compound I-cr was obtained (75 mg, 66%) as a white powder. $^1$H-NMR (300 MHz, DMSO-$d_6$, ppm from TMS): δ 10.72 (0.5H, bs), 10.63 (0.5H, bs), 9.02 (2H, bb), 5.17 (1H, d), 5.02 (1H, bs), 4.73 (1H, bs), 3.35-3.10 (6H, m), 3.15 (1H, m), 2.99 (1H, m), 2.70-1.00 (16H, m), 0.89 (3H, s), 0.88 (3H, s).

EXAMPLE 71

(E,Z) 3-[3'-(R)-Pyrrolidinyl]oxyimino-6α-hydroxymethylandrostane-7,17-dione fumarate (I-cs)

Prepared in 67% yield as described in Example 1 and starting from 6α-hydroxymethylandrostane-3,7,17-trione (II-be, Prepn. 42) and 3-(R)pyrrolidinyloxyamine dihydrochloride (III-e, Prepn. 5). The crude product was purified by flash chromatography ($SiO_2$, $CHCl_3$/MeOH/26% $NH_4OH$ 90/10/0.1). To the concentrated fractions a stoichiometric amount of fumaric acid in MeOH was added. After addition of a 1/1 mixture of EtOAc/$Et_2O$, the precipitate was filtered to give the title compound I-cs as white solid. $^1$H-NMR (300

MHz, DMSO-d$_6$, ppm from TMS): δ 6.41 (2H, s), 4.69 (1H, m), 4.18 (1H, bb), 3.70-3.00 (8H, m), 2-80-1.00 (19H, m), 1.15 (3H, s), 0.79 (3H, s).

EXAMPLE 72

(E,Z) 3-[3'-(R)-(1-Methyl)pyrrolidinyl]oxyimino-6α-hydroxymethylandrostane-7,17-dione fumarate (I-ct)

Prepared in 57% yield as described in Example 1 and starting from 6α-hydroxymethylandrostane-3,7,17-trione (II-be, Prepn. 42) and 3-(R)(1-methyl)pyrrolidinyloxyamine dihydrochloride (III-j, Prepn. 10). The crude product was purified by flash chromatography (SiO$_2$, CHCl$_3$/MeOH/26% NH$_4$OH 90/10/0.1). To the concentrated fractions a stoichiometric amount of fumaric acid in MeOH was added. After addition of a 1/1 mixture of EtOAc/Et$_2$O, the precipitate was filtered to give the title compound I-ct as a white solid. $^1$H-NMR (300 MHz, DMSO-d$_6$, ppm from TMS): δ 6.56 (2H, s), 4.62 (1H, m), 4.17 (1H, bb), 3.70-3.30 (8H, m), 3.22-3.12 (1H, m), 3.06-2.92 (1H, m), 2.37 (1.5H, s), 2.35 (1.5H, s), 2.90-1.00 (17H, m), 1.17 (1.5H, s), 1.16 (1.5H, s), 0.78 (3H, s).

EXAMPLE 73

(E,Z) 3-[3'-(S)-(1-Methyl)-pyrrolidinyl]oxyimino-6α-hydroxymethylandrostane-7,17-dione fumarate (I-cu)

Prepared in 72% yield as described in Example 1 and starting from 6α-hydroxymethylandrostane-3,7,17-trione (II-be, Prepn. 42) and 3-(S)(1-methyl)pyrrolidinyloxyamine dihydrochloride (III-i, Prepn. 9). The crude product was purified by flash chromatography (SiO$_2$, CHCl$_3$/MeOH/26% NH$_4$OH 90/10/0.1). To the concentrated fractions a stoichiometric amount of fumaric acid in MeOH was added. After addition of a 1/1 mixture of EtOAc/Et$_2$O, the precipitate was filtered to give the title compound I-cu as a white solid. $^1$H-NMR (300 MHz, DMSO-d$_6$, ppm from TMS): δ 6.55 (2H, s), 4.62 (1H, m), 4.18 (1H, bb), 3.70-3.30 (8H, m), 3.20-3.10 (1H, m), 3.05-2.95 (1H, m), 2.32 (3H, s), 2.80-1.00 (17H, m), 1.16 (3H, s), 0.79 (3H, s).

EXAMPLE 74

3β-(3-(R,S)-Piperidinylcarbonyloxy)androstane-6,7-dione hydrochloride (I-cv)

To a solution of 3β-[(R,S)-(1-tert-butoxycarbonylpiperidin-3-yl)carbonyloxy]androstane-6,17-dione (II-bf, Prepn. 43, 49 mg) in EtOAc (0.6 mL) at 0° C., 5 N HCl in EtOAc (0.85 mL) was added. After stirring for 15 min at room temperature the solution was evaporated and the residue was triturated with Et$_2$O to give the title compound I-cv (21 mg, 50%). $^1$H-NMR (300 MHz, DMSO-d$_6$, ppm from TMS): δ 8.84 (1H, bb), 8.56 (1H, bb), 4.61 (1H, m), 3.50-1.20 (29H, m), 0.78 (3H, s), 0.69 (3H, s).

EXAMPLE 75

3β-(4-Piperidinylcarbonyloxy)androstane-6,17-dione hydrochloride (I-cw)

Prepared in 61% yield as described in Example 29 starting from 3β-(N-(tert-butoxycarbonyl)piperidin-4-ylcarbonyloxy)androstane-6,17-dione (II-bg, Prepn. 44). $^1$H-NMR (300 MHz, DMSO-d$_6$, ppm from TMS): δ 8.90 (1H, bb), 8.80 (1H, bb), 4.62 (1H, m), 3.50-1.20 (29H, m), 0.78 (3H, s), 0.69 (3H, s).

EXAMPLE 76

3β-(3-Azetidincarbonyloxy)androstane-6,17-dione hydrochloride (I-cx)

Prepared in 30% yield as described in Example 29 starting from 3β-(N-(tert-butoxycarbonyl)azetidin-3-ylcarbonyloxy) androstane-6,17-dione (II-bh, Prepn. 45). $^1$H-NMR (300 MHz, DMSO-d$_6$, ppm from TMS): δ 8.95 (2H, bb), 4.64 (1H, m), 4.2-1 (25H, m), 0.78 (3H, s), 0.69 (3H, s).

EXAMPLE 77

3β-(3(R,S)-Pirrolidinylcarbonyloxy)androstane-6,17-dione fumarate (I-cy)

Prepared in 50% yield as described in Example 29 starting from 3β-(N-(tert-butoxycarbonyl)-pirrolidin-3(R,S)-ylcarbonyloxy)androstane-6,17-dione (II-bi, Prepn. 46). The crude product was purified by flash chromatography (SiO$_2$, CHCl$_3$/MeOH/26% NH$_4$OH 90/10/1). To the concentrated fractions, the stoichiometric amount of fumaric acid in MeOH was added, followed by a 1/1 mixture of EtOAc/Et$_2$O. The precipitate was filtered to give the title compound I-cy. $^1$H-NMR (300 MHz, DMSO-d$_6$, ppm from TMS): δ 8.00 (3H, bb) 6.43 (2H, s), 4.60 (1H, m), 3.30-2.90 (5H, m), 2.45-1.13 (22H, m), 0.78 (3H, s), 0.69 (3H, s).

EXAMPLE 78

3β-(2(R,S)-Morpholinylcarbonyloxy)androstane-6,7-dione fumarate (I-cz)

Prepared in 54% yield as described in Example 32 starting from 3β-(N-(tert-butoxycarbonyl)morpholin-2(R,S)-ylcarbonyloxy)androstane-6,17-dione (II-bj, Prepn. 47). $^1$H-NMR (300 MHz, DMSO-d$_6$, ppm from TMS): δ 8.00 (3H, bb), 6.43 (2H, s), 4.63 (1H, m), 4.09 (1H, m), 3.79 (1H, m), 3.50-2.60 (5H, m), 2.45-1.14 (20H, m), 0.78 (3H, s), 0.69 (3H, s).

EXAMPLE 79

3β-(2-(R,S)-piperazinylcarbonyloxy)androstane-6,7-dione dihydrochloride (I-da)

Prepared in 80% yield as described in Example 29 starting from 3β-(N,N'-bis(tert-butoxycarbonyl)piperazin-2(R,S)-ylcarbonyloxy)androstane-6,17-dione (II-bk, Prepn. 48). $^1$H-NMR (300 MHz, DMSO-d$_6$, ppm from TMS): δ 8.56 (4H, bb), 4.75 (1H, m), 4.53 (1H, m), 3.70-3.10 (6H, m), 2.60-1.15 (20H, m), 0.78 (3H, s), 0.71 (3H, s).

EXAMPLE 80

3α-[3-(RS)-Pyrrolidinylthio]-6-methyleneandrostane-17-one fumarate (I-db)

To a stirred solution of 3α-mercapto-6-methyleneandrostane-17-one (II-bl, Prepn. 49) (100 mg) in dry DMF (2 mL), NaH 60% in oil (30 mg) was added at 0° C. After 5 min. a solution of (RS) 3-bromopyrrolidine hydrochloride (Prepn. 64, 60 mg) in DMF (1 mL) was dropped in 30 min. at room temperature. After 2 hrs, a 5% NaH$_2$PO$_4$ solution was added.

The phases were separated and the aqueous phase was extracted with EtOAc. The organic layers were washed with brine, dried over $Na_2SO_4$ and evaporated to dryness. The crude product was purified by flash chromatography ($SiO_2$, $CH_2Cl_2$/MeOH/$NH_3$ 93/7/0.7). To the concentrated fractions the stoichiometric amount of fumaric acid in MeOH was added. After addition of EtOAc, the precipitate was filtered to give 0.10 g (62%) of the title compound I-db as a white solid. $^1$H-NMR (300 MHz, DMSO-$d_6$, ppm from TMS): δ 9.01 (2H, bb), 6.42 (2H, s), 4.78 (1H, m), 4.73 (1H, m), 4.38 (1H, m), 3.57 (1H, m), 3.30-3.10 (6H, m), 2.45-0.95 (20H, m), 0.76 (3H, s), 0.63 (3H, s).

EXAMPLE 81

3α-[3-(RS)-Pyrrolidinylthio]androstane-6,17-dione fumarate (I-dc)

Following the procedure described in Example 80 and starting from 3α-mercaptoandrostane-6,17-dione (II-bm, Prepn. 50) (200 mg), 3α-[3-(RS)-pyrrolidinylthio]androstane-6,17-dione fumarate was obtained from the crude product by addition of fumaric acid (58 mg) and washing the precipitate with EtOAc to give 130 mg (60% yield). $^1$H-NMR (300 MHz, DMSO-$d_6$, ppm from TMS): δ 6.42 (2H, s), 4.69 (1H, m), 3.57 (1H, m), 3.30-3.10 (6H, m), 2.45-0.95 (20H, m), 0.76 (3H, s), 0.63 (3H, s).

EXAMPLE 82

3α-[3-(RS)-Pyrrolidinylthio]-6-(E)-hydroxyiminoandrostane-17-one fumarate (I-dd)

The title compound was prepared following the procedure described in Example 1 and starting from 3α-[3-(RS)-pyrrolidinylthio]androstane-6,17-dione fumarate (I-dc, Example 81, 115 mg) and hydroxylamine hydrochloride (20 mg). The crude product was purified by flash chromatography ($SiO_2$, $CH_2Cl_2$/MeOH/$NH_3$ 9/1/0.1). To the concentrated fractions the stoichiometric amount of fumaric acid in MeOH was added. After addition of EtOAc, the precipitate was filtered to give the title compound I-dd as a white solid in 65% yield. $^1$H-NMR (300 MHz, DMSO-$d_6$, ppm from TMS): δ 10.72 (1H, bs), 6.42 (1H, m), 4.69 (1H, m), 3.57 (1H, m), 3.30-3.10 (6H, m), 2.40-0.95 (20H, m), 0.76 (3H, s), 0.63 (3H, s).

EXAMPLE 83

3α-[2-(Pyrrolidin-3-(S)-yl)-(Z)-vinyl]androstane-6,17-dione formate (I-de)

A solution of 3α-[1-(tert-butoxycarbonyl)pyrrolidin-3-(S)-yl)-(Z)vinyl]androstane-6,17-dione (II-bn, Prepn. 51, 110 mg) in formic acid (3 mL) was stirred at room temperature for 2 h. 15 mL of distilled water were then added and the resulting mixture freeze-dried to give the title compound I-de as a white solid, in 95% yield. $^1$H-NMR (300 MHz, DMSO-$d_6$, ppm from TMS): δ 9.01 (2H, bb), 5.82 (1H, t), 5.25 (1H, t), 3.55-3.05 (4H, m), 3.00-2.05 (7H, m), 2.00-1.10 (17H, m), 0.86 (3H, s), 0.78 (3H, s).

EXAMPLE 84

3α-[2-(Pyrrolidin-3-(R)-yl)-(Z)-vinyl]androstane-6,7-dione formate (I-df)

The title compound was prepared in 93% yield as described in Example 83 starting from 3α-[1-(tert-butoxycarbonyl)pyrrolidin-3-(R)-yl)-(Z)vinyl]androstane-6,17-dione (II-bc, Prepn. 53). $^1$H-NMR (300 MHz, DMSO-$d_6$, ppm from TMS): δ 8.99 (2H, bb), 5.80 (1H, t), 5.20 (1H, t), 3.55-3.05 (4H, m), 3.00-2.05 (7H, m), 2.00-1.10 (17H, m), 0.85 (3H, s), 0.77 (3H, s).

EXAMPLE 85

3α-[2-(Pyperidin-4-yl)-(Z)-vinyl]androstane-6,17-dione formate (I-dg)

The title compound was prepared in 90% yield as described in Example 83 starting from 3α-[1-(tert-butoxycarbonyl)pyperidin-4-yl)-(Z)vinyl]androstane-6,17-dione (Prepn. 55, II-bp). $^1$H-NMR (300 MHz, DMSO-$d_6$, ppm from TMS): δ 8.98 (2H, bb), 5.74 (1H, t), 5.19 (1H, t), 4.20-3.95 (2H, m), 3.00-1.05 (28H, m), 0.85 (3H, s), 0.77 (3H, s).

EXAMPLE 86

3α-[2-(Azetidin-3-yl)-(Z)-vinyl]androstane-6,7-dione formate (I-dh)

The title compound was prepared in 70% yield as described in Example 83 starting from 3α-[1-(tert-butoxycarbonyl)azetidin-3-yl)-(Z)vinyl]androstane-6,17-dione (Prepn. 57, II-bq). $^1$H-NMR (300 MHz, DMSO-$d_6$, ppm from TMS): δ 8.99 (2H, bb), 5.82 (1H, t), 5.65 (1H, t), 4.15-3.95 (2H, m), 3.65-3.45 (3H, m), 2.60-1.10 (21H, m), 0.86 (3H, s), 0.77 (3H, s).

EXAMPLE 87

(Z)-3-[3-(S)-Pyrrolidinyl)oxyimino]-6α-hydroxymethylandrostane-7,17-dione fumarate (I-di)

Prepared in 67% yield as described in Example 1 and starting from 6α-hydroxymethylandrostane-3,7,17-trione (II-be, Prepn. 42) and 3-(S)pyrrolidinyloxyamine dihydrochloride (III-d, Prepn. 4). The crude product was purified by flash chromatography ($SiO_2$, $CHCl_3$/MeOH/26% $NH_4OH$ 90/10/0.1). To the concentrated fractions a stoichiometric amount of fumaric acid in MeOH was added. After addition of $Et_2O$, the precipitate was filtered to give the title compound I-di in 35% yield, as white solid. $^1$H-NMR (300 MHz, DMSO-$d_6$, ppm from TMS): δ 9.02 (2H, bb), 6.41 (2H, s), 4.69 (1H, m), 4.25 (1H, t), 3.55 (2H, m), 3.32-3.10 (6H, m), 2.51 (2H, m), 2.10 (1H, m), 1.90-1.10 (16H, m), 0.95 (3H, s), 0.80 (3H, s).

EXAMPLE 88

(E)-3-[3-(S)-Pyrrolidinyl)oxyimino]-6α-hydroxymethylandrostane-7,17-dione fumarate (I-dj)

The title compound was obtained from the second fractions of the column described in Example 87. To the concentrated fractions a stoichiometric amount of fumaric acid in MeOH was added. After addition of $Et_2O$, the precipitate was filtered to give the title compound I-dj in 40% yield, as white solid. $^1$H-NMR (300 MHz, DMSO-$d_6$, ppm from TMS): δ 9.01 (2H, bb), 6.42 (2H, s), 4.69 (1H, m), 4.25 (1H, t), 3.55 (2H, m), 3.30-3.05 (6H, m), 2.51 (2H, m), 2.10 (1H, m), 1.90-1.10 (16H, m), 0.95 (3H, s), 0.80 (3H, s).

EXAMPLE 89

(E,Z) 3-[3-(R)-Pyrrolidinyl]oxyimino-6α-hydroxymethyl-7α-hydroxyandrostane-17-one hydrochloride (I-dk)

Prepared as described in Example 1 and starting from 6α-hydroxymethyl-7α-hydroxyandrostane-3,17-dione (II-br, Prepn. 59) (280 mg) and 3-(R)-pyrrolidinyloxyamine dihydrochloride (III-e, Prepn. 5) (150 mg). After 2 hours at room temperature, NaCl was added and stirred for 15 min. The mixture was extracted with THF (3 x) and the combined organic phases were washed with brine, dried over $Na_2SO_4$, and filtered. The solid precipitated from the filtrate was centrifuged, washed with AcOEt/iPrOH 9:1, to give the title compound I-dk in 55% yield. $^1$H-NMR (300 MHz, DMSO-$d_6$, ppm from TMS): δ 8.99 (2H, bb), 4.69 (1H, m), 4.35 (1H, t), 4.26 (1H, d), 3.86 (1H, m), 3.40 (2H, t), 3.25-3.00 (6H, m), 2.40-1.10 (19H, m), 1.00 (3H, s), 0.84 (3H, s).

EXAMPLE 90

(E,Z) 3-[3-(S)-Pyrrolidinyl]oxyimino-6α-hydroxymethyl-7α-hydroxyandrostane-17-one hydrochloride (I-dl)

Prepared in 61% yield as described in Example 89 and starting from 6α-hydroxymethyl-7α-hydroxyandrostane-3,17-dione (II-br, Prepn. 59) (280 mg) and 3-(S)-pyrrolidinyloxyamine dihydrochloride (III-d, Prepn. 4) (150 mg) as a white powder. $^1$H-NMR (300 MHz, DMSO-$d_6$, ppm from TMS): δ 9.02 (2H, bb), 4.69 (1H, m), 4.35 (1H, t), 4.26 (1H, d), 3.86 (1H, m), 3.40 (2H, t), 3.20-3.00 (6H, m), 2.40-1.10 (19H, m), 1.01 (3H, s), 0.82 (3H, s).

EXAMPLE 91

(E,Z) 3-[3-(R)-Pyrrolidinyl]oxyimino-7α-methoxymethylandrostane-17-one hydrochloride (I-dm)

Prepared in 80% yield as described in Example 1 and starting from 7α-methoxymethylandrostane-3,17-dione (II-bs, Prepn. 60) (200 mg) and 3-(R)-pyrrolidinyloxyamine dihydrochloride (III-e, Prepn. 5) (115 mg) as a white powder. $^1$H-NMR (300 MHz, DMSO-$d_6$, ppm from TMS): δ 9.01 (2H, bb), 4.69 (1H, m), 3.35 (3H, s), 3.28-3.00 (8H, m), 2.53-0.75 (21H, m), 1.10 (3H, s), 0.90 (3H, s).

EXAMPLE 92

(E,Z) 3-[3-(R)-Pyrrolidinyl]oxyimino-7α-methoxyandrostane-17-one fumarate (I-dn)

Prepared in 75% yield as described in Example 1 and starting from 7αmethoxyandrostane-3,17-dione (II-bt, Prepn. 61) (150 mg) and 3-(R)pyrrolidinyloxyamine dihydrochloride (III-e, Prepn. 5) (110 mg) as a white powder. $^1$H-NMR (300 MHz, DMSO-$d_6$, ppm from TMS): δ 8.99 (2H, bb), 6.42 (2H, s), 4.69 (1H, m), 3.35 (3H, s), 3.20-3.00 (6H, m), 2.58-1.00 (21H, m), 0.96 (3H, s), 0.78 (3H, s).

EXAMPLE 93

(E,Z) 3-[3-(R)-Pyrrolidinyl]oxyiminoandrostane-6α, 17β-diol hydrochloride (I-do)

Prepared in 85% yield as described in Example 1 and starting from 6α,17β-dihydroxyandrostane-3-one (prepared as described in EP 0825197 B1, 100 mg) and 3-(R)-pyrrolidinyloxyamine dihydrochloride (III-e, Prepn. 5) (60 mg) as a white powder. $^1$H-NMR (300 MHz, DMSO-$d_6$, ppm from TMS): δ 9.01 (2H, bb), 4.69 (1H, m), 4.30-4.20 (2H, m), 3.70-3.50 (2H, m), 3.35-3.10 (6H, m), 2.50-1.00 (20H, m), 0.96 (3H, s), 0.78 (3H, s).

EXAMPLE 94

(E,Z) 3-[3'-(R)-Pyrrolidinyl]oxyimino-6β-hydroxyandrostane-17-one hydrochloride (I-dp)

Prepared in 80% yield as described in Example 1 and starting from 6β-hydroxyandrostane-3,17-dione (100 mg) and 3-(R)pyrrolidinyloxyamine dihydrochloride (III-e, Prepn. 5) (60 mg) as a white powder. $^1$H-NMR (300 MHz, DMSO-$d_6$, ppm from TMS): δ 9.02 (2H, bb), 4.69 (1H, m), 4.34 (1H, d), 3.75 (1H, m), 3.35-3.10 (6H, m), 2.50-1.00 (20H, m), 0.96 (3H, s), 0.78 (3H, s).

EXAMPLE 95

(E,Z) 3-[3'-(R)-(1-Methyl)pyrrolidinyl]oxyimino-5α-hydroxy-6-(E)hydroxyiminoandrostane-17-one fumarate (I-dq)

Prepared in 65% yield as described in Example 1 and starting from 5α-hydroxy-6-(E)-hydroxyiminoandrostane-3,17-dione (II-aq, Prepn. 27) (100 mg) and 3-(R)-(1-methyl)pyrrolidinyloxyamine dihydrochloride (III-j, Prepn. 10) (60 mg) as a white powder. $^1$H-NMR (300 MHz, DMSO-$d_6$, ppm from TMS): δ 10.71 (1H, bs), 6.41 (2H, s), 5.28 (1H, bb), 4.69 (1H, m), 3.37-3.10 (7H, m), 2.32 (3H, s), 2.25-1.10 (18H, m), 0.85 (3H, s), 0.74 (3H, s).

EXAMPLE 96

(Z) 3-[3-(R)-Pyrrolidinyl]oxyimino-5α-hydroxy-6-(E)-hydroxyiminoandrostane-17-one fumarate (I-dr)

The title compound I-dr was obtained following the procedure described in Example 1 and starting from 5α-hydroxy-6-(E)hydroxyiminoandrostane-3,17-dione (II-aq, Prepn. 27, 3 g) and 3-(R)pyrrolidinyloxyamine dihydrochloride (III-e, Prepn. 5, 1.7 g). The crude product (a mixture 70/30 of the E/Z isomers) was purified by flash chromatography ($SiO_2$, $CH_2Cl_2$/MeOH/26% $NH_4OH$ 90/10/1). To the concentrated less polar fractions the stoichiometric amount of fumaric acid in MeOH was added, followed by a 1/1 mixture of EtOAc/$Et_2O$. The precipitate was filtered to give the title compound I-dr in 32% yield. $^1$H-NMR (300 MHz, DMSO-$d_6$, ppm from TMS): δ 10.67 (1H, s), 9.01 (2H, bb), 6.41 (2H, s), 5.08 (0.5H, s), 4.95 (0.5H, s), 4.73 (1H, m), 3.51-2.90 (6H, m), 2.62-1.10 (19H, m), 0.82 (3H, s), 0.76 (3H, s).

EXAMPLE 97

(E) 3-[3-(R)-Pyrrolidinyl]oxyimino-5α-hydroxy-6-(E)-hydroxyiminoandrostane-17-one fumarate (I-ds)

Isolated from the concentrated more polar fractions after the flash chromatography described in Example 95. The stoichiometric amount of fumaric acid in MeOH was added, followed by a 1/1 mixture of EtOAc/Et$_2$O. The precipitate was filtered to give the title compound I-ds in 48% yield as a white solid. $^1$H-NMR (300 MHz, DMSO-d$_6$, ppm from TMS): δ 10.64 (0.5H, s), 9.01 (2H, bb), 6.41 (2H, s), 5.08 (0.5H, s), 4.95 (0.5H, s), 4.73 (1H, m), 3.51-2.90 (6H, m), 2.62-1.10 (19H, m), 0.82 (3H, s), 0.76 (3H, s).

EXAMPLE 98

(Z) 3-[3-(S)-Pyrrolidinyl]oxyimino-5α-hydroxy-6-(E)-hydroxyiminoandrostane-17-one fumarate (I-dt)

To a stirred solution of (Z) 3-[(S)-3-N-(9H-fluoren-9-ylmethyl)pyrrolidinyl]oxyimino-5α-hydroxy-6-(E)-hydroxyiminoandrostane-17-one (II-bu, Prepn. 62, 920 mg) in dry THF (12 mL) at 0° C., 1M tetrabutylammonium fluoride in THF (1.7 mL) was added. After stirring at room temperature for 3 h, the solution was concentrated to small volume and purified by flash chromatography (SiO$_2$, CH$_2$Cl$_2$/MeOH/26% NH$_4$OH 90/10/1). To the concentrated fractions the stoichiometric amount of fumaric acid in MeOH was added. The precipitate was filtered to give the title compound I-dt in 80% yield. $^1$H-NMR (300 MHz, DMSO-d$_6$, ppm from TMS): δ 10.72 (1H, bs), 9.02 (2H, bb), 6.41 (2H, s), 4.85 (1H, bs), 4.73 (1H, bs), 3.35-3.10 (6H, m), 3.15 (1H, m), 2.99 (1H, m), 2.70-1.00 (17H, m), 0.84 (3H, s), 0.78 (3H, s).

EXAMPLE 99

(E) 3-[3-(S)-Pyrrolidinyl]oxyimino-5α-hydroxy-6-(E)-hydroxyiminoandrostane-17-one fumarate (I-du)

To a stirred solution of (E) 3-[(S)-3-N-(9H-fluoren-9-ylmethyl)pyrrolidinyl]oxyimino-5α-hydroxy-6-(E)-hydroxyiminoandrostane-17-one (II-by, Prepn. 62, 930 mg) in dry THF (12 mL) at 0° C., 1M tetrabutylammonium fluoride in THF (1.7 mL) was added. After stirring at room temperature for 3 h, the solution was concentrated to small volume and purified by flash chromatography (SiO$_2$, CH$_2$Cl$_2$/MeOH/26% NH$_4$OH 90/10/1). The stoichiometric amount of fumaric acid in MeOH was added, the precipitate was filtered to give the title compound I-du in 80% yield. $^1$H-NMR (300 MHz, DMSO-d$_6$, ppm from TMS): δ 10.63 (1H, bs), 9.02 (2H, bb), 6.41 (2H, s), 4.85 (1H, bs), 4.73 (1H, bs), 3.35-3.10 (6H, m), 3.15 (1H, m), 2.99 (1H, m), 2.70-1.00 (17H, m), 0.83 (3H, s), 0.78 (3H, s).

EXAMPLE 100

(E,Z) 3-[3-(S)-Pyrrolidinyl]oxyimino-6-(E)-hydroxyiminoandrost-4-ene-17-one fumarate (I-dv)

Prepared as described in Example 1 and starting from 6-(E)-hydroxyiminoandrost-4-ene-3,17-dione (II-bw, Prepn. 63) (160 mg) and 3-(S)-pyrrolidinyloxyamine dihydrochloride (III-d, Prepn. 4) (90 mg). The crude product was purified by flash chromatography (SiO$_2$, CH$_2$Cl$_2$/MeOH/26% NH$_4$OH 90/10/1). To the concentrated fractions the stoichiometric amount of fumaric acid in MeOH was added, the precipitate was filtered to give the title compound I-dv in 70% yield. $^1$H-NMR (300 MHz, DMSO-d$_6$, ppm from TMS): δ 10.72 (1H, bs), 9.01 (2H, bb), 6.41 (2H, s), 6.16 (1H, bs), 3.37-3.10 (7H, m), 2.55-1.10 (16H, m), 0.95 (3H, s), 0.83 (3H, s).

EXAMPLE 101

(Z) 3-[3-(S)-Pyrrolidinyl]oxyimino-6-(E)-hydroxyiminoandrost-4-ene-17-one (I-dw)

The title compound I-dw was obtained following the procedure described in Example 100 and starting from 6-(E)-hydroxyiminoandrost-4-ene-3,17-dione (II-bw, Prepn. 63, 200 mg) and 3-(S)-pyrrolidinyloxyamine dihydrochloride (III-d, Prepn. 4) (110 mg). The crude product (1/1 ratio of the E/Z isomers) was purified by flash chromatography (SiO$_2$, CH$_2$Cl$_2$/MeOH/26% NH$_4$OH 90/10/1). The less polar fractions were evaporated to dryness to give the title compound I-dw in 65% yield. $^1$H-NMR (300 MHz, DMSO-d$_6$, ppm from TMS): δ 10.72 (1H, bs), 6.16 (1H, bs), 4.69 (1H, m), 3.36-3.10 (7H, m), 2.60-1.10 (16H, m), 0.96 (3H, s), 0.83 (3H, s).

EXAMPLE 102

(E) 3-[3-(S)-Pyrrolidinyl]oxyimino-6-(E)-hydroxyiminoandrostane-4-ene-17-one (I-dx)

Isolated from the concentrated more polar fractions after the flash chromatography described in Example 101, after evaporation to dryness, in 55% yield. $^1$H-NMR (300 MHz, DMSO-d$_6$, ppm from TMS): δ 10.71 (1H, bs), 6.16 (1H, bs), 4.69 (1H, m), 3.36-3.10 (7H, m), 2.55-1.10 (16H, m), 0.95 (3H, s), 0.82 (3H, s).

PREPARATION 1

4-Piperidyloxyamine dihydrochloride (III-a)

To a solution of tert-butyl 4-hydroxy-1-piperidinecarboxylate (1.00 g), triphenyl phosphine (2.62 g) and N-hydroxyphthalimide (1.63 g) in THF (55 mL) at 0° C., diisopropyl azodicarboxylate (2.16 mL) was added dropwise. After stirring for 6 hrs, the solvent was evaporated and the crude product was purified by flash chromatography (SiO$_2$, n-hexane:EtOAc, from 8:2 to 6:4) to give of 1-tert-butoxycarbonyl-4-phthalimidoxypiperidine (1.48 g, 85%). $^1$H-NMR (300 MHz, DMSO-d$_6$, ppm from TMS): δ 7.87 (4H, m), 4.46 (1H, m), 3.82 (2H, m), 3.23 (2H, m), 1.98 (2H, m), 1.73 (2H, m), 1.45 (9H, s).

To a suspension of 1-tert-butoxycarbonyl-4-phthalimidoxypiperidine (430 mg) in MeOH (5 mL), hydrazine (26% in water, 0.23 mL) was added. After stirring at room temperature for 15 min, the mixture was filtered. The filtrate was evaporated to dryness and purified by flash chromatography (SiO$_2$, CH$_2$Cl$_2$:MeOH 9:1) to give of 1-tert-butoxycarbonyl-4-piperidyloxyamine (120 mg, 46%). $^1$H-NMR (300 MHz, DMSO-d$_6$, ppm from TMS): δ 5.86 (2H, bb), 3.55 (3H, m), 3.00 (2H, m), 1.75 (2H, m), 1.37 (9H, s), 1.32 (2H, m).

1-tert-Butoxycarbonyl-4-piperidyloxyamine (120 mg) was dissolved in a 5M HCl solution in EtOAc (3 mL). After 1 h the solvent was removed under reduced pressure to give the title compound III-a (100 mg, 96%). $^1$H-NMR (300 MHz, DMSO-d$_6$, ppm from TMS): δ 10.95 (3H, bb), 8.96 (2H, bb), 4.33 (1H, m), 3.13 (2H, m), 3.00 (2H, m), 2.09 (2H, m), 1.85 (2H, m).

PREPARATION 2

3-Azetidinyloxyamine dihydrochloride (III-b)

1-(Diphenylmethyl)-3-hydroxyazetidine (9.70 g) was suspended in 4.5 M HCl in EtOAc (35 mL) at room temperature and stirred for 10 min. The solvent was then evaporated to dryness to give 1-(diphenylmethyl)-3-hydroxyazetidine hydrochloride (12.0 g, 100%). $^1$H-NMR (300 MHz, DMSO-$d_6$, ppm from TMS): δ 7.30-7.70 (10H, m), 5.85 (1H, s), 5.80 (1H, d), 4.46 (1H, m), 3.70-4.20 (4H, m).

A solution of 1-(diphenylmethyl)-3-hydroxyazetidine hydrochloride (11.8 g) in absolute ethanol (700 mL) was hydrogenated at room temperature over Pd(OH)$_2$/C in a Parr shaker at 4 atm. After 12 hr the catalyst was filtered off and the filtrate evaporated to dryness to give 3-hydroxyazetidine hydrochloride (4.20 g, 94%). $^1$H-NMR (300 MHz, DMSO-$d_6$, ppm from TMS): δ 9.07 (2H, bb), 6.19 (1H, bb), 4.49 (1H, m), 3.99 (2H, m), 3.71 (2H, m).

To a solution of 3-hydroxyazetidine hydrochloride (2.20 g) and triethylamine (4.0 mL) in MeOH (20 mL) at 0° C., di-tert-butyl dicarbonate (3.12 g) was added. After stirring at room temperature for 6 h, the solvent was evaporated. The residue was diluted with CH$_2$Cl$_2$, washed with water and the organic phase was evaporated to dryness to give tert-butyl 3-hydroxy-1-azetidinecarboxylate (3.22 g, 93%) which was used without purification in the next step. $^1$H-NMR (300 MHz, DMSO-$d_6$, ppm from TMS): δ 5.62 (1H, d), 4.35 (1H, m), 3.96 (2H, m), 3.55 (2H, m), 1.35 (9H, s).

To a solution of tert-butyl 3-hydroxy-1-azetidinecarboxylate (2.28 g), triphenyl phosphine (6.80 g) and N-hydroxyphthalimide (4.24 g) in THF (162 mL) at 0° C., 1,1'-(azodicarbonyl)dipiperidine (7.21 g) was added. After stirring at room temperature for 27 h, the solvent was evaporated and the crude product purified by flash chromatography (SiO$_2$, n-hexane:EtOAc 6:4) to give 1-tert-butoxycarbonyl-3-phthalimidoxyazetidine (2.10 g, 50%). $^1$H-NMR (300 MHz, DMSO-$d_6$, ppm from TMS): δ 7.86 (4H, m), 4.98 (1H, m), 4.12 (2H, m), 3.95 (2H, m), 1.38 (9H, s).

tert-Butoxycarbonyl-3-phthalimidoxyazetidine (1.00 g) was dissolved in 5M EtOAc (10 mL). After 5 hrs, the mixture was filtered and 3-phthalimidoxyazetidine hydrochloride was obtained after evaporation of the filtrate (0.90 g, 100%) and used without purification in the next step. $^1$H-NMR (300 MHz, DMSO-$d_6$, ppm from TMS): δ 9.28 (2H, bb), 7.88 (4H, m), 5.09 (1H, m), 4.28 (2H, m), 4.13 (2H, m).

To a solution of 3-phthalimidoxyazetidine hydrochloride (0.90 g) in MeOH (20 mL), hydrazine hydrate (0.15 mL) was added. After 6 hr, water was added, the solvent concentrated and 1N HCl (10 mL) was added. After 30 min the white solid was filtered and the filtrate was freeze-dried to give the title compound III-b (500 mg. 100%). $^1$H-NMR (300 MHz, DMSO-$d_6$, ppm from TMS): δ 11.00 (3H, bb), 9.58 (1H, bb), 9.32 (1H, bb), 5.06 (1H, m), 4.18 (2H, m), 4.01 (2H, m).

PREPARATION 3

3(RS)-Pyrrolidinyloxyamine dihydrochloride (III-c)

Following the procedure described in Prepn. 2 and starting from (RS) 3-hydroxypyrrolidine (2.15 g), (RS) 1-tert-butoxycarbonyl-3-pyrrolidinol was obtained (4.10 g, 89%) and used without purification in the next step. $^1$H-NMR (300 MHz, DMSO-$d_6$, ppm from TMS): δ 4.98 (1H, d), 4.19 (1H, m), 3.30-3.00 (4H, m), 1.90-1.60 (2H, m), 1.37 (9H, s).

Following the procedure described in Prepn. 2 and starting from (RS) 1-tert-butoxycarbonylpyrrolidin-3-ol (4.10 g), (RS) 1-tert-butoxycarbonyl-3-phthalimidoxypyrrolidine was obtained, after purification by flash chromatography (SiO$_2$, CH$_2$Cl$_2$:n-hexane:acetone 5:4:1) (3.10 g, 40%). $^1$H-NMR (300 MHz, DMSO-$d_6$, ppm from TMS): δ 7.86 (4H, m), 4.88 (1H, m), 3.65-3.35 (4H, m), 2.20-1.90 (2H, m), 1.41 (9H, s).

Following the procedure described in Prepn. 1 and starting from (RS) 1-tert-butoxycarbonyl-3-phthalimidoxypyrrolidine (1.08 g), (RS) 1-tert-butoxycarbonyl-3-pyrrolidinyloxyamine hydrochloride was obtained as a yellow oil (480 mg, 74%), after purification by flash chromatography (SiO$_2$, CH$_2$Cl$_2$:EtOAc 8:2). $^1$H-NMR (300 MHz, DMSO-$d_6$, ppm from TMS): δ 6.00 (2H, bb), 4.08 (1H, m), 3.45-3.05 (4H, m), 2.00-1.70 (2H, m), 1.38 (9H, s).

Following the procedure described in Prepn. 1 and starting from (RS) 1-tert-butoxycarbonyl-3-pyrrolidinyloxyamine hydrochloride (480 mg), (RS) 3-pyrrolidinyloxyamine dihydrochloride (III-c) was obtained (294 mg, 75%) as a white solid. $^1$H-NMR (300 MHz, DMSO-$d_6$, ppm from TMS): δ 11.01 (3H, bb), 9.62 (1H, bb), 9.46 (1H, bb), 4.94 (1H, m), 3.50-3.05 (4H, m), 2.35-2.00 (2H, m).

PREPARATION 4

3(S)-Pyrrolidinyloxyamine dihydrochloride (III-d)

Following the procedure described in Prepn. 2 and starting from (R)-3-pyrrolidinol, (R)—N-tert-butoxycarbonyl-3-pyrrolidinol was obtained and used without purification in the next step. $^1$H-NMR (300 MHz, DMSO-$d_6$, ppm from TMS): δ 4.98 (1H, d), 4.19 (1H, m), 3.30-3.00 (4H, m), 1.90-1.60 (2H, m), 1.37 (9H, s).

Following the procedure described in Prepn. 2 and starting from (R)—N-tert-butoxycarbonyl-3-pyrrolidinol (4.00 g), (S) 1-tert-butoxycarbonyl-3-O-phthalimidoxypyrrolidine was obtained (2.50 g, 35%). after flash chromatography (SiO$_2$, CH$_2$Cl$_2$:n-hexane:acetone 5:4:1), $^1$H-NMR (300 MHz, DMSO-$d_6$, ppm from TMS): δ 7.86 (10H, m), 4.88 (1H, m), 3.65-3.35 (4H, m), 2.22-1.88 (2H, m), 1.41 (9H, s).

Following the procedure described in Prepn. 1 and starting from (S) 1-tert-butoxycarbonyl-3-phthalimidoxypyrrolidine (2.50 g) (S) 1-tert-butoxycarbonyl-3-pyrrolidinyloxyamine was obtained (1.49 g, 98%) as a green oil. $^1$H-NMR (300 MHz, DMSO-$d_6$, ppm from TMS): δ 4.87 (1H, d), 4.19 (1H, m), 3.30-3.00 (4H, m), 1.90-1.60 (2H, m), 1.37 (9H, s).

Following the procedure described in Prepn. 1 and starting from (S) 1-tert-butoxycarbonyl-3-pyrrolidinyloxyamine (1.67 g), (S) 3-pyrrolidinyloxyamine dihydrochloride was obtained (1.04 g, 73%) as an off-white solid. $^1$H-NMR (300 MHz, DMSO-$d_6$, ppm from TMS): δ 11.09 (3H, bb), 9.64 (1H, bb), 9.47 (1H, bb), 4.95 (1H, m), 3.55-3.00 (4H, m), 2.35-1.95 (2H, m).

PREPARATION 5

3(R)-Pyrrolidinyloxyamine dihydrochloride (III-e)

Following the procedure described in Prepn. 2 and starting from (S)-3-hydroxypyrrolidine hydrochloride (15.0 g), N-tert-butoxycarbonyl-(S)pyrrolidinol (21.4 g, 95% yield) was obtained and used without purification in the next step. $^1$H-NMR (300 MHz, DMSO-$d_6$, ppm from TMS): δ 4.87 (1H, d), 4.19 (1H, m), 3.30-3.00 (4H, m), 1.90-1.60 (2H, m), 1.37 (9H, s).

To a solution of N-tert-butoxycarbonyl-(S)-pyrrolidinol (10.0 g) and triethylamine (8.2 mL) in CH$_2$Cl$_2$ (150 mL) at 0° C., methanesulfonyl chloride (4.34 mL) was added. After stirring at room temperature for 3 h, the reaction mixture was poured into ice/water and extracted with CH$_2$Cl$_2$. The organic phase was washed with 5% aqueous NaHCO$_3$, water, brine, dried and evaporated to dryness to give an oil which solidified after standing overnight in the refrigerator. The solid was triturated with Et$_2$O to give N-tert-butoxycarbonyl-(S)-3-pyrrolidinyl methansulfonate (13.0 g, 92%) as a light yellow solid. $^1$H-NMR (300 MHz, DMSO-d$_6$, ppm from TMS): δ 5.23 (1H, m), 3.60-3.10 (4H, m), 3.23 (3H, s), 2.11 (2H, m), 1.39 (9H, s).

To a suspension of KOH powder (4.86 g) in DMSO (250 mL) under vigorous stirring, benzophenone oxime (7.86 g) was added. After stirring at room temperature for 30 min, a solution of N-tert-butoxycarbonyl(S)-3-pyrrolidinyl methansulfonate (10 g) in DMSO (70 mL) was added. After 18 h at room temperature the reaction was poured into iced water (900 mL) and extracted with Et$_2$O. The combined organic layers were washed with water, brine, dried and the solvent evaporated. Benzophenone O—[(R)-3-pyrrolidinyl]oxime was obtained (13.0 g, 96%) as a white solid and used without purification in the next step. $^1$H-NMR (300 MHz, DMSO-d$_6$, ppm from TMS): δ 7.50-7.20 (10H, m), 4.84 (1H, m), 3.50-3.00 (4H, m), 2.01 (2H, m), 1.38 (9H, s).

Benzophenone O—[(R)-3-pyrrolidinyl]oxime (13.0 g) was suspended in 6N HCl (250 mL) and the mixture was refluxed for 2 h. After cooling, the reaction was extracted with Et$_2$O. The aqueous layer was evaporated to give a crude brown solid which was treated with 0.34 g of activated carbon in absolute EtOH (255 mL) at reflux for 2 h. The solid obtained after evaporation was crystallized with 96% EtOH (40 mL) to give the title compound III-e (2.98 g, 72%), as an off white solid. $^1$H-NMR (300 MHz, DMSO-d$_6$, ppm from TMS): δ 11.22 (3H, bb), 9.74 (1H, bb), 9.54 (1H, bb), 4.98 (1H, m), 3.60-3.00 (4H, m), 2.40-2.00 (2H, m).

PREPARATION 6

2(R)-Pyrrolidinylmethoxyamine dihydrochloride (III-f)

Following the procedure described in Prepn. 1 and starting from (R)-1-(tert-butoxycarbonyl)-2-pyrrolidinemethanol (1.50 g), (R)-1-(tert-butoxycarbonyl)-2-(phthalimidoxymethyl)pyrrolidine was obtained (1.70 g, 66%) after purification by flash chromatography (SiO$_2$, CH$_2$Cl$_2$:n-hexane:acetone 50:45:5). $^1$H-NMR (300 MHz, DMSO-d$_6$, ppm from TMS): δ 7.87 (4H, m), 4.34 (1H, m), 4.20-3.95 (2H, m), 3.32 (2H, m), 2.35-1.80 (4H, m), 1.37 (9H, s).

Following the procedure described in Prepn. 1 and starting from (R)-1-(tert-butoxycarbonyl)-2-(phthalimidoxymethyl)pyrrolidine (1.21 g), (R)-1-(tert-butoxycarbonyl)-2-pyrrolidinylmethoxyamine was obtained (0.76 g, 100%) from the residue of the evaporation by washing with EtOAc and filtration and used without purification. $^1$H-NMR (300 MHz, DMSO-d$_6$, ppm from TMS): δ 6.01 (2H, bb), 4.00-3.00 (5H, m), 1.77 (4H, m), 1.38 (9H, s).

Following the procedure described in Prepn. 1 and starting from (R)-1-(tert-butoxycarbonyl)-2-pyrrolidinylmethoxyamine (0.76 g), (R)-2-pyrrolidinylmethoxyamine dihydrochloride (III-f) was obtained from the crude by washing with EtOH and filtering (0.60 g, 90%). $^1$H-NMR (300 MHz, DMSO-d$_6$, ppm from TMS): δ 11.07 (3H, bb), 9.84 (2H, bb), 4.26 (2H, m), 3.79 (1H, m), 3.14 (2H, m), 2.15-1.50 (4H, m).

PREPARATION 7

2(S)-Pyrrolidinylmethoxyamine dihydrochloride (III-v)

Following the procedure described in Prepn. 1 and starting from (S)-1-(tert-butoxycarbonyl)-2-pyrrolidinemethanol (1.50 g), (S)-1-(tert-butoxycarbonyl)-2-(phthalimidoxymethyl)pyrrolidine was obtained (1.70 g, 66%) after purification by flash chromatography (SiO$_2$, CH$_2$Cl$_2$:n-hexane:acetone 50:45:5). $^1$H-NMR (300 MHz, DMSO-d$_6$, ppm from TMS): δ 7.86 (4H, m), 4.25-3.80 (3H, m), 3.21 (2H, m), 2.20-1.70 (4H, m), 1.30 (9H, s).

Following the procedure described in Prepn. 1 and starting from (S)-1-(tert-butoxycarbonyl)-2-(phthalimidoxymethyl)pyrrolidine (1.46 g), (S)-1-(tert-butoxycarbonyl)-2-pyrrolidinylmethoxy-amine was obtained (0.73 g, 80%) from the residue of the evaporation by washing with EtOAc and filtration and used without purification $^1$H-NMR (300 MHz, DMSO-d$_6$, ppm from TMS): δ 6.02 (2H, bb), 3.86 (1H, m), 3.60-3.30 (2H, m), 3.18 (2H, m), 1.76 (4H, m), 1.38 (9H, s).

Following the procedure described in Prepn. 1 and starting from (S)-1-(tert-butoxycarbonyl)-2-pyrrolidinylmethoxyamine (730 mg), (S)-2-pyrrolidinylmethoxyamine dihydrochloride (III-g) was obtained from the crude by washing with EtOH. (600 mg, 90%). $^1$H-NMR (300 MHz, DMSO-d$_6$, ppm from TMS): δ 11.12 (3H, bb), 9.83 (2H, bb), 4.26 (2H, m), 3.79 (1H, m), 3.14 (2H, m), 2.10-1.50 (4H, m).

PREPARATION 8

3(RS)-Piperidinyloxyamine dihydrochloride (III-h)

Following the procedure described in Prepn. 2 and starting from (R,S) 3-hydroxypiperidine hydrochloride (1.00 g), (R,S) tert-butyl 3-hydroxy-1-piperidinecarboxylate was obtained (1.50 g, 75%) as a white solid. $^1$H-NMR (300 MHz, DMSO-d$_6$, ppm from TMS): δ 4.82 (1H, d), 3.72 (1H, m), 3.60 (1H, m), 3.34 (1H, m), 2.76 (1H, m), 2.60 (1H, m), 1.85-1.20 (4H, m), 1.37 (9H, s).

Following the procedure described in Prepn. 1 and starting from (R,S) tert-butyl 3-hydroxy-1-piperidinecarboxylate (1.00 g), (R,S) tert-butoxycarbonyl-3-phthalimidoxypiperidine was obtained (1.00 g, 70%), after purification by flash chromatography (SiO$_2$, CH$_2$Cl$_2$:n-hexane:acetone 3:6:1). $^1$H-NMR (300 MHz, DMSO-d$_6$, ppm from TMS): δ 7.87 (4H, m), 4.20 (1H, m), 3.80-3.00 (4H, m), 2.00-1.30 (4H, m), 1.35 (9H, s).

Following the procedure described in Prepn. 1 and starting from (R,S) tert-butoxycarbonyl-3-phthalimidoxypiperidine (600 mg), 1-tert-butoxycarbonyl-3-(R,S)-piperidinyloxyamine was obtained (335 mg, 90%) as an oil. $^1$H-NMR (300 MHz, DMSO-d$_6$, ppm from TMS): δ 5.87 (2H, bb), 4.35 (1H, m), 3.60-3.10 (4H, m), 1.90-1.20 (4H, m), 1.37 (9H, s).

Following the procedure described in Prepn. 1 and starting from 1-tert-butoxycarbonyl-3-(R,S)-piperidinyloxyamine (200 mg) and 2N HCl in Et$_2$O (1.5 mL), 3-(R,S)-piperidinyloxyamine dihydrochloride (III-h) was obtained (138 mg, 100%) as an off white solid. $^1$H-NMR (300 MHz, DMSO-d$_6$, ppm from TMS): δ 11.07 (3H, bb), 9.55 (1H, bb), 8.83 (1H, bb), 4.45 (1H, m), 3.31 (2H, m), 2.96 (2H, m), 2.00-1.50 (4H, m).

PREPARATION 9

3-(S)-(1-Methyl)pyrrolidinyloxyamine dihydrochloride (III-i)

Following the procedure described in Prepn. 5 and starting from 3-(R)(1-methyl)pyrrolidinol (3.2 g), 3-(R)-(1-methyl)pyrrolidinyl methansulfonate was obtained (5.0 g, 73%) as a light yellow solid. $^1$H-NMR (300 MHz, DMSO-d$_6$, ppm from TMS): δ 5.18-5.08 (1H, m), 3.15 (3H, s), 2.80-2.55 (3H, m), 2.35-2.15 (5H, m), 1.95-1.80 (1H, m).

Following the procedure described in Prepn. 5 and starting from benzophenone oxime (5.9 g) and 3-(R)-(1-methyl)pyrrolidinyl methansulfonate (5.0 g) benzophenone O-[3-(S)-(1-Methyl)pyrrolidinyl]oxime was obtained (7.8 g, quantitative yield) as a white solid. $^1$H-NMR (300 MHz, DMSO-d$_6$, ppm from TMS): δ 7.50-7.20 (10H, m), 4.87 (1H, m), 2.80-2.60 (3H, m), 2.40-2.15 (5H, m), 1.95-1.80 (1H, m).

Following the procedure described in Prepn. 5 and starting from benzophenone O-[3-(S)-(1-methyl)pyrrolidinyl]oxime (7.8 g), the title compound III-i was obtained (3.8 g, 70%), as an off white solid. $^1$H-NMR (300 MHz, DMSO-d$_6$, ppm from TMS): δ 11.50-10.50 (4H, bb), 5.00-4.85 (1H, bb), 3.60-3.00 (7H, m), 2.40-2.00 (2H, m).

PREPARATION 10

3-(R)-(1-Methyl)-pyrrolidinyloxyamine dihydrochloride (III-i)

Following the procedure described in Prepn. 5 and starting from 3-(S)(1-methyl)pyrrolidinol (3.2 g), 3-(S)-(1-methyl)pyrrolidinyl methansulfonate was obtained (5.0 g, 73%) and used without purification in the next step. $^1$H-NMR (300 MHz, DMSO-d$_6$, ppm from TMS): δ 5.18-5.08 (1H, m), 3.15 (3H, s), 2.80-2.55 (3H, m), 2.35-2.15 (5H, m), 1.95-1.80 (1H, m).

Following the procedure described in Prepn. 5 and starting from 3-(S)(1-methyl)pyrrolidinyl methansulfonate (5.0 g), benzophenone O-[3-(R)(1-methyl)pyrrolidinyl]oxime was obtained (7.8 g, quantitative yield) as a white solid and used without purification in the next step. $^1$H-NMR (300 MHz, DMSO-d$_6$, ppm from TMS): δ 7.50-7.20 (10H, m), 4.87 (1H, m), 2.80-2.60 (3H, m), 2.40-2.15 (5H, m), 1.95-1.80 (1H, m).

Following the procedure described in Prepn. 5 and starting from benzophenone O-[3-(R)-(1-methyl)pyrrolidinyl]oxime (7.8 g), the title compound III-j was obtained (4.0 g, 74%) as a white solid. $^1$H-NMR (300 MHz, DMSO-d$_6$, ppm from TMS): δ 11.50-10.50 (4H, bb), 5.00-4.85 (1H, bb), 3.60-3.00 (7H, m), 2.40-2.00 (2H, m).

PREPARATION 11

5α-Hydroxyandrostane-3,17-dione (II-aa)

To a stirred solution of 3β-hydroxyandrost-4-en-17-one (0.81 g) in CH$_2$Cl$_2$ (7.4 mL) cooled at 0° C., a solution of mCPBA (0.77 mg) in CH$_2$Cl$_2$ (13.6 mL) was added dropwise. After 0.5 h at 0° C. and 0.5 h at room temperature, a 10% aqueous solution of Na$_2$SO$_3$ was added. The mixture was neutralized by addition of 5% NaHCO$_3$ solution and extracted with CH$_2$Cl$_2$ (3×100 mL). The combined organic extracts were washed with H$_2$O, dried over Na$_2$SO$_4$, and evaporated to dryness. The residue was purified by flash chromatography (SiO$_2$, n-hexane/CH$_2$Cl$_2$/acetone 60/20/20) to give 3β-hydroxy-5α,6α-epoxyandrostane-17-one (0.64 g, 75%). $^1$H-NMR (300 MHz, DMSO-d$_6$, ppm from TMS): δ 4.62 (1H, d), 3.52 (1H, m), 2.87 (1H, d), 2.44-0.56 (19H, m), 1.00 (3H, s), 0.72 (3H, s).

To a stirred suspension of LiAlH$_4$ (0.247 mg) in THF under N$_2$ (10.5 mL), a solution of 3β-hydroxy-5α,6α-epoxyandrostane-17-one (0.64 g) in THF (20 mL) was added dropwise and the mixture was stirred at reflux for 8 h. The suspension was cooled with an ice bath and then quenched by careful addition of H$_2$O (1 mL) and 4N NaOH (0.20 mL). The mixture was filtered through a Celite pad and the filter cake was washed with THF (3×10 mL). The filtrate was dried over Na$_2$SO$_4$, evaporated to dryness and the residue was purified by flash chromatography (SiO$_2$, n-hexane/CH$_2$Cl$_2$/acetone 40/30/30) to give androstane-3β,5α,17β-triol (0.48 g, 74%). $^1$H-NMR (300 MHz, DMSO-d$_6$, ppm from TMS): δ 4.37 (1H, d), 4.19 (1H, d), 3.78 (1H, m), 3.62 (1H, s), 3.39 (1H, m), 1.87-0.80 (21H, m), 0.86 (3H, s), 0.59 (3H, s).

A solution of androstane-3β,5α,17β-triol (0.48 g) and IBX (0.72 g) in DMSO (8 mL) was stirred at −15° C. overnight and then quenched at room temperature by addition of H$_2$O (40 mL). After stirring for 15 min, the mixture was filtered and the cake was washed with EtOAc. The layers were separated, and the aqueous phase was extracted with EtOAc (3×40 mL). The combined organic extracts were dried over Na$_2$SO$_4$ and evaporated to dryness. The residue was purified by flash chromatography (SiO$_2$, n-hexane/CH$_2$Cl$_2$/acetone 60/20/20) to give the title compound II-aa (0.36 g, 75%). $^1$H-NMR (300 MHz, acetone-d$_6$, ppm from TMS): δ 3.48 (1H, s), 2.72 (1H, d), 2.60-1.18 (20H, m), 1.23 (3H, s), 0.86 (3H, s).

PREPARATION 12

3,17-Dioxoandrostane-6α-yl nitrate (II-ab)

To a solution of acetic anhydride (2.53 mL) and 65% HNO$_3$ (0.592 mL) cooled at 0° C., 3,3:17,17-bis(ethylendioxy)androstane-6α-ol (2.5 g) was added in one portion. After 2 h the mixture was quenched by careful addition of ice and 5% aqueous NaHCO$_3$ solution and was extracted with CH$_2$Cl$_2$ (3×). The combined organic extracts were washed with H$_2$O, dried over Na$_2$SO$_4$, and evaporated to dryness to give 3,3:17,17-bis(ethylendioxy)androstane-6α-yl nitrate as a white solid (2.50 g, 89%). $^1$H-NMR (300 MHz, acetone-d$_6$, ppm from TMS): δ 4.94 (1H, m), 3.94-3.75 (8H, m), 2.24-0.74 (20H, m), 0.98 (3H, s), 0.85 (3H, s).

A solution of 3,3:17,17-bis(ethylendioxy)androstane-6α-yl nitrate (2.50 g) and pTSA.H$_2$O (6.05 g) in acetone (150 mL) was stirred at room temperature for 1.5 h. The solution was neutralized by addition of 5% aqueous NaHCO$_3$, and acetone was evaporated. The aqueous phase was extracted with CH$_2$Cl$_2$ (3×50 mL). The combined organic extracts were washed with H$_2$O, dried over Na$_2$SO$_4$ and evaporated to dryness. The residue was purified by flash chromatography (SiO$_2$, cyclohexane/Acetone/CH$_2$Cl$_2$ 70/15/15) to give the title compound II-ab as a white solid (1.66 g, 75%). $^1$H-NMR (300 MHz, acetone-d$_6$, ppm from TMS): δ 5.09 (1H, ddd), 2.60-0.95 (17H, m), 1.25 (3H, s), 0.90 (3H, s).

PREPARATION 13

6-Methyleneandrostane-3,17-dione (II-ac)

To a stirred suspension of methyltriphenylphosphonium bromide (9.50 g) in dry THF (77 mL) cooled at 0° C. under N$_2$, potassium tert-butoxide (2.91 g) was added. After stirring for 10 min, a solution of 3,3:17,17-bis(ethylendioxy)androstane-6-one (2.60 g) in dry THF (77 mL) was added dropwise at room temperature over 0.5 h. After 0.5 h at room temperature, the mixture was quenched by addition of 5% NaH$_2$PO$_4$ aqueous solution and extracted with Et$_2$O (2×60 mL). The combined organic extracts were washed with 5% NaH$_2$PO$_4$ aqueous solution, brine, dried over Na$_2$SO$_4$ and evaporated to dryness. The residue was purified by flash chromatography (SiO$_2$, cyclohexane/EtOAc 85/15) to give 3,3:17,17-bis(ethylendioxy)-6-methyleneandrostane (2.66 g, 97%). $^1$H-NMR (300 MHz, acetone-d$_6$, ppm from TMS): δ 4.68 (1H, m), 4.36 (1H, m), 3.88-3.71 (8H, m), 2.27-0.78 (20H, m), 0.74 (3H, s), 0.62 (3H, s).

A solution of 3,3:17,17-bis(ethylendioxy)-6-methyleneandrostane (1.05 g) and pTSA.H$_2$O (2.46 g) in acetone (105 mL) was stirred at room temperature for 3 h. The solution was neutralized by addition of 5% aqueous NaHCO$_3$ and acetone was evaporated. The aqueous suspension was extracted with CH$_2$Cl$_2$ (3×). The combined organic extracts were washed with H$_2$O, dried over Na$_2$SO$_4$ and evaporated to dryness to give the title compound II-ac in 87% yield. $^1$H-NMR (300 MHz, acetone-d$_6$, ppm from TMS): δ 4.85 (1H, m), 4.50 (1H, m), 2.63-1.02 (20H, m), 0.92 (3H, s), 0.86 (3H, s).

PREPARATION 14

6α-Hydroxymethylandrostane-3,17-dione (II-ad)

To a stirred solution of 3,3:17,17-bis(ethylendioxy)-6-methyleneandrostane (Prepn. 13, 2.89 g) in dry THF (29 mL) at 0° C. under N$_2$, 1M BH$_3$.THF complex in THF (5.21 mL) was added. After completing the addition, the mixture was stirred at 0° C. for 3 h. H$_2$O (2.3 mL) was cautiously added dropwise followed by 3N NaOH (3 mL) and 9.8 M H$_2$O$_2$ (0.91 mL). After stirring at room temperature overnight, H$_2$O (20 mL) was added and the mixture was extracted with EtOAc (2×20 mL). The combined organic extracts were washed with brine, dried over Na$_2$SO$_4$, filtered and evaporated to dryness. The residue was purified by flash chromatography (SiO$_2$, n-hexane/EtOAc 45/55) to give 3,3:17,17-bis(ethylendioxy)-6β-hydroxymethylandrostane (2.86 g, 95%). $^1$H-NMR (300 MHz, acetone-d$_6$, ppm from TMS): δ 3.94-3.75 (8H, m), 3.52 (2H, m), 3.36 (1H, t), 2.05-0.65 (21H, m), 0.84 (3H, s), 0.81 (3H, s).

To a solution of 3,3:17,17-bis(ethylendioxy)-6β-hydroxymethylandrostane (0.63 g) in DMSO (6 mL), IBX (0.87 g) was added and stirred at room temperature for 1 h. The mixture was quenched by addition of H$_2$O (30 mL) and Et$_2$O (30 mL). After stirring for 15 min, the mixture was filtered and the cake was washed with Et$_2$O. The layers were separated and the aqueous phase was extracted with Et$_2$O (3×). The combined organic extracts were washed with brine, dried over Na$_2$SO$_4$ and evaporated to dryness. The residue was purified by flash chromatography (SiO$_2$, n-hexane/EtOAc 75/35) to give 3,3:17,17-bis(ethylendioxy)-6β-formylandrostane (0.52 g, 83%). $^1$H-NMR (300 MHz, acetone-d$_6$, ppm from TMS): δ 9.92 (1H, d), 3.96-3.75 (8H, m), 2.32-0.68 (21H, m), 0.81 (3H, s), 0.77 (3H, s), A mixture of 3,3:17,17-bis(ethylendioxy)-6β-formylandrostane (0.61 g), K$_2$CO$_3$ (0.90 g) in MeOH (57 mL) was stirred overnight at room temperature. After evaporation, the residue was treated with H$_2$O (20 mL) and extracted with EtOAc (3×30 mL). The combined organic extracts were washed with brine (3×20 mL), dried over Na$_2$SO$_4$ and evaporated to dryness to give 3,3:17,17-bis(ethylendioxy)-6α-formylandrostane (0.57 g, 94%). $^1$H-NMR (300 MHz, acetone-d$_6$, ppm from TMS): δ 9.41 (1H, d), 3.95-3.72 (8H, m), 2.24-0.73 (21H, m), 0.90 (3H, s), 0.84 (3H, s).

To a stirred suspension of 3,3:17,17-bis(ethylendioxy)-6α-formylandrostane (0.52 g) in dioxane/H$_2$O 9/1 (25 mL), NaBH$_4$ (0.049 g) was added and the mixture was stirred overnight at room temperature. To the solution NaCl was added and the layers were separated. The aqueous phase was extracted with EtOAc (3×). The combined organic extracts were washed with brine, dried over Na$_2$SO$_4$ and evaporated to dryness to give 3,3:17,17-bis(ethylendioxy)-6α-hydroxymethylandrostane (0.45 g, 86%) $^1$H-NMR (300 MHz, acetone-d$_6$, ppm from TMS): δ 3.94-3.75 (8H, m),3.57-3.25 (3H, m), 1.98-0.60 (21H, m), 0.86 (3H, s), 0.83 (3H, s).

The title compound II-ad was prepared in 85% yield from 3,3:17,17-bis(ethylendioxy)-6α-hydroxymethylandrostane by the procedure described above for the preparation of 6-methyleneandrostane-3,17-dione (II-ac, Prepn. 13). The combined organic extracts were washed with H$_2$O, dried and evaporated to dryness. $^1$H-NMR (300 MHz, acetone-d$_6$, ppm from TMS): δ 3.50 (3H, m), 2.52-0.74 (21H, m), 1.11 (3H, s), 0.88 (3H, s).

PREPARATION 15

6α-Methoxymethylandrostane-3,17-dione (II-ae)

To a stirred solution of 3,3:17,17-bis(ethylendioxy)-6α-hydroxymethylandrostane (Prepn. 14, 0.80 g) in dry THF (11 mL) at 0° C., under N$_2$, NaH (60% dispersion, 96 mg) was added. After stirring the mixture at 0° C. for 1 h, CH$_3$I (144 µL) was added. After stirring overnight at room temperature, H$_2$O (10 mL) was added and the mixture extracted with EtOAc (2×20 mL). The combined organic extracts were dried over Na$_2$SO$_4$, filtered and evaporated to dryness. The residue was purified by flash chromatography (SiO$_2$, n-hexane/acetone 90/10) to give 3,3:17,17-bis(ethylendioxy)-6α-methoxymethylandrostane (0.70 g, 84%). $^1$H-NMR (300 MHz, acetone-d$_6$, ppm from TMS): δ 3.92-3.70 (8H, m), 3.25 (1H, dd), 3.23 (3H, s), 3.14 (1H, dd), 1.97-0.59 (21H, m), 0.85 (3H, s), 0.82 (3H, s).

The title compound II-ae was prepared in 88% yield from 3,3:17,17-bis(ethylendioxy)-6α-methoxymethylandrostane by the procedure described above for the preparation of 6-methyleneandrostane-3,17-dione (II-ac, Prepn. 13). The combined organic extracts were washed with H$_2$O, dried over Na$_2$SO$_4$ and evaporated to dryness. $^1$H-NMR (300 MHz, acetone-d$_6$, ppm from TMS): δ 3.25 (3H, s), 3.24 (2H, m), 2.53-0.75 (21H, m), 1.11 (3H, s), 0.87 (3H, s).

PREPARATION 16

6α-Carbamoylandrostane-3,17-dione (II-af)

6α-Formylandrostane-3,17-dione was prepared in 85% yield from 3,3:17,17-bis(ethylendioxy)-6α-formylandrostane (Prepn. 14) by the procedure described above for the preparation of 6-methyleneandrostane-3,17-dione (II-ac, Prepn. 13). The combined organic extracts were washed with H$_2$O, dried over Na$_2$SO$_4$ and evaporated to dryness to give 6α-formylandrostane-3,17-dione. $^1$H-NMR (300 MHz, acetone-d$_6$, ppm from TMS): δ 9.50 (1H, d), 2.56-0.82 (21H, m), 1.16 (3H, s), 0.88 (3H, s).

To a stirred suspension of 6α-formylandrostane-3,17-dione (1.77 g) in t-ButOH (35 mL) and 5% aqueous Na$_2$HPO$_4$ solution (21.5 mL), 1N aqueous KMnO$_4$ (35 mL) was added. After 5 minutes at room temperature, the mixture was quenched by addition of 40% aqueous NaHSO$_3$ solution. The suspension was filtered, washed with H$_2$O and the filtrate was freeze-dried. The residue was taken up with H$_2$O (50 mL) and extracted with EtOAc (4×70 mL). The combined organic extracts were dried over Na$_2$SO$_4$ and evaporated to dryness to give 6α-carboxyandrostane-3,17-dione (1.80 g, 96%). $^1$H-NMR (300 MHz, acetone-d$_6$, ppm from TMS): δ 11.99 (1H, bb), 2.46-0.73 (21H, m), 1.01 (3H, s), 0.79 (3H, s).

To a stirred suspension of 6α-carboxyandrostane-3,17-dione (1.20 g) in dry toluene (12 mL), SOCl$_2$ (1.2 mL) was added. After stirring 5.5 h at 85° C. the solution was cooled at 0° C. and 2M NH$_3$ solution in THF (6 mL) was added. After stirring overnight at room temperature, the mixture was evaporated to dryness. The residue was treated with CH$_2$Cl$_2$ and H$_2$O and extracted with CH$_2$Cl$_2$. The combined organic extracts were washed with 10% K$_2$CO$_3$ solution, brine, dried over Na$_2$SO$_4$ and evaporated to dryness. The residue was purified by flash chromatography (SiO$_2$, n-hexane/acetone 50/50) to give the title compound II-af (720 mg, 60%). $^1$H-NMR (300 MHz, DMSO-d$_6$, ppm from TMS): δ 7.27 (1H, bs), 6.78 (1H, bs), 2.50-0.72 (21H, m), 1.00 (3H, s), 0.80 (3H, s).

PREPARATION 17

6α-Methoxycarbonylandrostane-3,17-dione (II-ag)

To a stirred solution of 6α-carboxyandrostane-3,17-dione (Prepn. 16, 680 mg) in CH$_2$Cl$_2$ (30 mL) at 0° C., MeOH (160 μL), DMAP (20 mg) and EDAC (800 mg) were added. After stirring overnight at room temperature, H$_2$O was added and the mixture was extracted with CH$_2$Cl$_2$ (2×). The combined organic extracts were washed with H$_2$O, brine, dried over Na$_2$SO$_4$, filtered and evaporated to dryness. The residue was purified by flash chromatography (SiO$_2$, n-hexane/EtOAc 60/40) to give the title compound II-ag (500 mg, 70%). $^1$H-NMR (300 MHz, DMSO-d$_6$, ppm from TMS): δ 3.59 (3H, s), 2.53-0.75 (21H, m), 1.02 (3H, s), 0.79 (3H, s).

PREPARATION 18

6-(E)-Hydroxyiminoandrostane-3,17-dione (II-ah)

To a stirred solution of 3,3:17,17-bis(ethylendioxy)androstane-6-one (1.10 g) in THF (22 mL) a solution of NH$_2$OH.HCl (0.33 g), Na$_2$HPO$_4$.12H$_2$O (1.71 g) in H$_2$O (7.2 mL) was added. After stirring overnight at room temperature, NaCl was added and the mixture was extracted with EtOAc (2×). The combined organic extracts were washed with brine, dried over Na$_2$SO$_4$, filtered and evaporated to dryness to give 3,3:17,17-bis(ethylendioxy)-6-(E)-hydroxyimino-androstane (1.08 g, 93%). $^1$H-NMR (300 MHz, DMSO-d$_6$, ppm from TMS): δ 10.34 (1H, s), 3.88-3.71 (8H, m), 3.16 (1H, dd), 2.22-0.86 (19H, m), 0.74 (3H, s), 0.64 (3H, s).

The title compound II-ah was prepared in 70% yield from 3,3:17,17-bis(ethylendioxy)-6-(E)-hydroxyiminoandrostane by the procedure described above for the preparation of 6-methyleneandrostane-3,17-dione (II-ac, Prepn. 13). The combined organic extracts were washed with H$_2$O, dried and evaporated to dryness. The residue was purified by flash chromatography (SiO$_2$, n-hexane/acetone 70/30). $^1$H-NMR (300 MHz, DMSO-d$_6$, ppm from TMS): δ 10.61 (1H, s), 3.29 (1H, dd), 2.61-1.03 (19H, m), 0.88 (3H, s), 0.79 (3H, s).

PREPARATION 19

6α-Methylandrostane-3,17-dione (II-ai)

To a stirred solution of DABCO (0.55 g) and 3,3:17,17-bis(ethylendioxy)-6α-hydroxymethylandrostane (Prepn. 14, 1.00 g) in dry CH$_2$Cl$_2$ (20 mL), under N$_2$ at 0° C., p-TSCl (0.703 g) was added. After stirring 2 h at room temperature, the mixture was filtered and the cake was washed with CH$_2$Cl$_2$. The organic layer was washed with brine, dried over Na$_2$SO$_4$ and evaporated to dryness. The crude product was triturated with n-hexane/EtOAc (60/40) and filtered. After drying under vacuum at 40° C., 3,3:17,17-bis(ethylendioxy)-6α-[4-methyl(benzenesulfonyloxy)methyl]androstane (1.11 g, 80%) was obtained. $^1$H-NMR (300 MHz, acetone-d$_6$, ppm from TMS): δ 7.82 (2H, m), 7.49 (2H, m), 4.00-3.74 (10H, m), 2.46 (3H, s), 1.97-0.57 (21H, m), 0.82 (3H, s), 0.80 (3H, s).

To a stirred solution of NaBH$_4$ (0.15 g) in dry DMSO (90 mL), under N$_2$, 3, 3:17,17-bis(ethylendioxy)-6α-[4-methyl (benzenesulfonyloxy)methyl]androstane (1.11 g) was added in portions over 15 min. After stirring for 3 h at 80° C., the mixture was quenched at room temperature by careful addition of H$_2$O (200 mL). The suspension was extracted with Et$_2$O. The combined organic extracts were washed with brine, dried over Na$_2$SO$_4$ and evaporated to dryness. The mixture was purified by flash chromatography (SiO$_2$, n-hexane/EtOAc 90/10) to give 3,3:17,17-bis(ethylendioxy)-6α-methylandrostane (0.70 g, 90%). $^1$H-NMR (300 MHz, acetone-d$_6$, ppm from TMS): δ 3.94-3.72 (8H, m), 1.98-0.53 (21H, m), 0.85 (3H, s), 0.83 (3H, s), 0.79 (3H, d).

The title compound II-ai was prepared in 94% yield from 3,3:17,17-bis(ethylendioxy)-6α-methylandrostane by the procedure described above for the preparation of 6-methyleneandrostane-3,17-dione (II-ac, Prepn. 13). The combined organic extracts were washed with H$_2$O, dried and evaporated to dryness. $^1$H-NMR (300 MHz, acetone-d$_6$, ppm from TMS): δ 2.77-0.75 (21H, m), 1.18 (3H, s), 0.98 (3H, d), 0.90 (3H, s).

PREPARATION 20

6α-Formamidoandrostane-3,17-dione (II-aj)

To a stirred solution of 3,3:17,17-bis(ethylendioxy)-6-(E)-hydroxyimino-androstane (Prepn. 18, 0.88 g) in n-PrOH (26 mL), Na (2.0 g) was added in small pieces over 20 min. The mixture was stirred at reflux for 2 h. After cooling to room temperature, the mixture was quenched by careful addition of MeOH. To the solution H$_2$O was added carefully and the organic solvent was evaporated. The mixture was extracted with CH$_2$Cl$_2$ (3×). The combined organic extracts were washed with brine, dried over Na$_2$SO$_4$, filtered and evaporated to dryness. The mixture was purified by flash chromatography (SiO$_2$, CHCl$_3$/MeOH/26% NH$_4$OH 90/10/1) to give 3,3:17,17-bis(ethylendioxy)-6α-aminoandrostane (0.45 g, 53%). $^1$H-NMR (300 MHz, DMSO-d$_6$, ppm from TMS): δ 3.87-3.70 (8H, m), 2.29 (1H, m), 1.98-0.50 (22H, m), 0.75 (3H, s), 0.74 (3H, s)

A 2 M solution of formic acid in CHCl$_3$ (0.67 mL) was added dropwise to a solution of DCC (106 mg) in CHCl$_3$ at 0° C. The mixture was stirred for further 5 min and then added to an ice-cooled solution of 3,3:17,17-bis(ethylendioxy)-6α-aminoandrostane (100 mg) in pyridine (0.70 mL) over 30 min. The mixture was then stirred in an ice bath for 4 h. Evaporation of the solvent was followed by addition of Et$_2$O. The precipitate was removed by filtration and washed with Et$_2$O. The combined organic extracts were evaporated to dryness to give 3,3:17,17-bis(ethylendioxy)-6α-formamidoandrostane (100 mg, 95%). $^1$H-NMR (300 MHz, DMSO-d$_6$, ppm from TMS): δ 7.98-7.43 (2H, m), 3.89-3.00 (9H, m), 1.93-0.50 (20H, m), 0.81 (3H, s), 0.77 (3H, s).

The title compound II-aj was prepared in 96% yield from 3,3:17,17-bis(ethylendioxy)-6α-formamidoandrostane by the procedure described above for the preparation of 6-methyleneandrostane-3,17-dione (II-ac, Prepn. 13). The combined organic extracts were washed with H$_2$O, dried over Na$_2$SO$_4$ and evaporated to dryness. $^1$H-NMR (300 MHz, DMSO-d$_6$, ppm from TMS): δ 8.02-7.56 (2H, m), 3.74 (1H, m), 2.54-0.70 (20H, m), 1.04 (3H, s), 0.80 (3H, s).

PREPARATION 21

6-Difluoromethyleneandrostane-3,17-dione (II-ak)

To a stirred solution of diethyl difluoromethylenephosphonate (0.67 μL) in DME (5.75 mL) in n-pentane (1.1 mL) at −78° C., 1.5 M pentane solution of tert-butyllithium (2.75 mL) was added dropwise under argon. After 15 min at the same temperature, a solution of 3,3:17,17-bis(ethylendioxy)androstane-6-one (0.50 g) in DME (4.5 mL) and n-pentane (1.25 mL) was added dropwise. The mixture was stirred at −78° C. for further 30 min and warmed up to room temperature. n-Pentane was distilled off and after heating at 80° C. for 4 h the mixture was quenched with $H_2O$ and extracted with $CH_2Cl_2$ (3×). The combined organic extracts were dried over $Na_2SO_4$ and evaporated to dryness. The residue was purified by flash chromatography ($SiO_2$, cyclohexane/$Et_2O$ 70/30) to give 3,3:17,17-bis(ethylendioxy)-6-difluoromethyleneandrostane (0.47 g, 85%). $^1$H-NMR (300 MHz, acetone-$d_6$, ppm from TMS): δ 3.85 (8H, m), 2.52-0.80 (20H, m), 0.83 (3H, s), 0.84 (3H, s).

The title compound II-ak was prepared in 99% yield from 3,3:17,17-bis(ethylendioxy)-6-difluoromethyleneandrostane by the procedure described above for the preparation of 6-methyleneandrostane-3,17-dione (II-ac, Prepn. 13). The combined organic extracts were washed with $H_2O$, dried over $Na_2SO_4$ and evaporated to dryness. $^1$H-NMR (300 MHz, acetone-$d_6$, ppm from TMS): δ 2.85-0.95 (20H, m), 1.12 (3H, s), 0.88 (3H, s).

PREPARATION 22

6-(Spirocyclopropane)androstane-3,17-dione (II-al)

To a stirred solution of 3,3:17,17-bis(ethylendioxy)-6-methylene-androstane (Prepn. 13, 200 mg) in dry toluene (10 mL) under $N_2$, 1 M $Et_2Zn$ in n-hexane (2.5 mL) was added. After heating at 60° C., $CH_2I_2$ (0.42 mL) was added in portions over 15 min. After 26 h the mixture was cooled and quenched by careful addition of 1N HCl. The suspension was extracted with $Et_2O$. The combined organic extracts were washed with 5% aqueous $NaHCO_3$ solution, brine, dried over $Na_2SO_4$ and evaporated to dryness. The crude product was dissolved in acetone (20 mL) and pTSA.$H_2O$ (39 mg) was added and the solution stirred at room temperature for 1 h. The solution was neutralized by addition of 5% aqueous $NaHCO_3$ and acetone was evaporated. The aqueous suspension was extracted with EtOAc. The combined organic extracts were washed with $H_2O$, dried over $Na_2SO_4$ and evaporated to dryness. The residue was purified by flash chromatography ($SiO_2$, n-hexane/$CH_2Cl_2$/EtOAc 90/5/5) to give the title compound II-al (78 mg, 48%). $^1$H-NMR (300 MHz, acetone-$d_6$, ppm from TMS: δ 2.51-0.83 (20H, m), 1.17 (3H, s), 0.88 (3H, s), 0.60 (1H, m), 0.41 (1H, m), 0.34 (1H, m), −0.08 (1H, m).

PREPARATION 23

6α-Ethynylandrostane-3,17-dione (II-am)

To a stirred solution of (chloromethyl)triphenylphosphonium chloride (1.20 g) in dry THF (20 mL) at −78° C. under argon, 1.6 M n-butyllithium in n-hexane (1.5 mL) was added dropwise. After 30 min at room temperature, a solution of 3,3:17,17-bis(ethylendioxy)-6α-formylandrostane (Prepn. 14, 0.28 g) in dry THF (7 mL) was added dropwise. The mixture was heated at 70° C. for 1 h and then cooled to room temperature. The mixture was quenched by addition of brine and extracted with EtOAc (3×). The combined organic extracts were dried over $Na_2SO_4$, and evaporated to dryness. The crude product was dissolved in dry THF (20 mL) and stirred at −78° C. To the resulting solution 1.6 M n-butyllithium in n-hexane (2.24 mL) under argon was added dropwise. After 1 h at room temperature the mixture was quenched by addition of brine and extracted with $Et_2O$ (3×). The combined organic extracts were dried over $Na_2SO_4$, and evaporated to dryness to give 3,3:17,17-bis(ethylendioxy)-6α-ethynylandrostane (160 mg, 46%), sufficiently pure to be used in the next step without further purification. $^1$H-NMR (300 MHz, acetone-$d_6$, ppm from TMS): δ 3.85 (8H, m), 2.46 (1H, d), 2.30-0.67 (21H, m), 0.82 (3H, s), 0.86 (3H, s).

The title compound II-am was prepared in 46% yield from 3,3:17,17-bis(ethylendioxy)-6α-ethynylandrostane by the procedure described for the preparation of 6-methyleneandrostane-3,17-dione (II-ac, Prepn. 13). The combined organic extracts were washed with $H_2O$, dried over $Na_2SO_4$ and evaporated to dryness. The residue was purified by flash chromatography ($SiO_2$, cyclohexane/$CH_2Cl_2$/acetone 80/10/10). $^1$H-NMR (300 MHz, acetone-$d_6$, ppm from TMS): δ 2.69-0.78 (22H, m), 1.12 (3H, s), 0.87 (3H, s).

PREPARATION 24

6α-(2-Hydroxyethyl)androstane-3,17-dione (II-an)

3,3:17,17-Bis(ethylendioxy)-6α-vinylandrostane was prepared in 70% yield from 3,3:17,17-bis(ethylendioxy)-6α-formylandrostane (Prepn. 14) by the procedure described above for the preparation of 3,3:17,17-bis(ethylendioxy)-6-methyleneandrostane (Prepn. 13). The crude was purified by flash chromatography ($SiO_2$, n-hexane/EtOAc 88/12). $^1$H-NMR (300 MHz, acetone-$d_6$, ppm from TMS): δ 5.47 (1H, m), 4.91 (2H, m), 3.94-3.73 (8H, m), 2.00-0.67 (21H, m), 0.88 (3H, s), 0.83 (3H, s).

3,3:17,17-Bis(ethylendioxy)-6α-(2-hydroxyethyl)androstane was prepared in 96% yield from 3,3:17,17-bis(ethylendioxy)-6α-vinylandrostane by the procedure described above for the preparation of 3,3:17,17-bis(ethylendioxy)-6α-hydroxymethyl-androstane (Prepn. 14). The crude was purified by flash chromatography ($SiO_2$, n-hexane/acetone 80/20). $^1$H-NMR (300 MHz, DMSO-$d_6$, ppm from TMS): δ 4.25 (1H, t), 3.86-3.70 (8H, m), 3.35 (2H, m), 1.91-0.42 (23H, m), 0.75 (3H, s), 0.74 (3H, s).

The title compound II-an was prepared in 100% yield from 3,3:17,17-bis(ethylendioxy)-6α-(2-hydroxyethyl)androstane by the procedure described above for the preparation of 6-methyleneandrostane-3,17-dione (II-ac, Prepn. 13). The combined organic extracts were washed with $H_2O$, dried over $Na_2SO_4$ and evaporated to dryness. $^1$H-NMR (300 MHz, DMSO-$d_6$, ppm from TMS): δ 4.32 (1H, t), 3.39 (2H, m), 2.46-0.54 (23H, m), 0.98 (3H, s), 0.79 (3H, s).

PREPARATION 25

6-(E)-Methoxyiminoandrostane-3,17-dione (II-ao)

3,3:17,17-Bis(ethylendioxy)-6-(E)-methoxyiminoandrostane was prepared in 90% yield from 3,3:17,17-bis(ethylendioxy)androstan-6-one (1.00 g) by the procedure described above for the preparation of 3,3:17,17-bis(ethylendioxy)-6 (E)-hydroxyiminoandrostane (Prepn. 18). The combined organic extracts were washed with brine, dried over $Na_2SO_4$, filtered and evaporated to dryness to give 3,3:17,17-bis(ethylendioxy)-6-(E)-methoxyiminoandrostane (1.04 g, 97%).

¹H-NMR (300 MHz, acetone-d₆, ppm from TMS): δ 3.94-3.76 (8H, m), 3.73 (3H, s), 3.22 (1H, dd), 2.29-0.95 (19H, m), 0.82 (3H, s), 0.75 (3H, s).

The title compound II-ao was prepared in 70% yield from 3,3:17,17-bis(ethylendioxy)-6-(E)-methoxyiminoandrostane by the procedure described above for the preparation of 6-methyleneandrostane-3,17-dione (II-ac, Prepn. 13). The combined organic extracts were washed with H₂O, dried over Na₂SO₄ and evaporated to dryness. ¹H-NMR (300 MHz, acetone-d₆, ppm from TMS): δ 3.78 (3H, s), 3.37 (1H, dd), 2.68-1.14 (19H, m), 1.01 (3H, s), 0.98 (3H, s).

PREPARATION 26

5α-Hydroxy-6-methyleneandrostane-3,17-dione (II-ap)

To a stirred solution of 3β-hydroxyandrost-5-en-17-one (0.81 g) in CH₂Cl₂ (7.4 mL) cooled at 0° C., a solution of mCPBA (0.77 mg) in CH₂Cl₂ (14 mL) was added dropwise. After 0.5 h at 0° C. and 0.5 h at room temperature, a 10% Na₂SO₃ aqueous solution was added. The mixture was neutralized by addition of 5% aqueous NaHCO₃ solution and extracted with CH₂Cl₂ (3×100 mL). The combined organic extracts were washed with H₂O, dried over Na₂SO₄, and evaporated to dryness to give 5α,6α-epoxyandrostan-17-one and 5β,6β-epoxyandrostan-17-one as a white foam (1/1 mixture; 1.24 g, 97%). ¹H-NMR (300 MHz, acetone-d₆, ppm from TMS): 3β-hydroxy-5α,6α-epoxyandrostan-17-one δ 3.26 (1H, d), 2.96 (1H, d), 2.70-1.12 (18H, m), 1.36 (3H, s), 0.83 (3H, s); 3β-hydroxy-5α,6β-epoxyandrostan-17-one: δ 2.98 (1H, d), 2.93 (1H, d), 2.71-1.13 (18H, m), 1.06 (3H, s), 0.84 (3H, s).

To a solution of a 1/1 mixture of 3β-hydroxy-5α,6α-epoxyandrostane-17-one and 3β-hydroxy-5β,6β-epoxyandrostan-17-one (2.10 g, 6.90 mmol) in acetone (38 mL), Jones reagent (8.35 mL) was added dropwise, maintaining the temperature below 40° C. 5 min after completion of the addition, i-PrOH (10 mL) was added and, after further 10 min, the suspension was filtered and the filtrate evaporated to dryness. The residue was treated with H₂O (300 mL) and extracted with EtOAc (3×100 mL). The combined organic extracts were washed with H₂O (100 mL), 5% aqueous NaHCO₃ solution (100 mL), H₂O (100 mL), dried over Na₂SO₄ and evaporated to dryness to give 5α-hydroxyandrostane-3,6,17-trione as a white solid (1.65 g, 75%). ¹H-NMR (300 MHz, acetone-d₆, ppm from TMS): δ 5.00 (1H, s), 2.85 (2H, m), 2.45-1.25 (17H, m), 1.06 (3H, s), 0.88 (3H, s).

A solution of 5α-hydroxyandrostane-3,6,17-trione (2.23 g) and pTSA.H₂O (80 mg) in 2-methyl-2-ethyl-1,3-dioxolane (29 mL) was stirred at 40° C. for 6 h. The solution was neutralized by addition of 5% aqueous Na₂HPO₄ and extracted with EtOAc. The combined organic extracts were washed with brine, dried over Na₂SO₄ and evaporated to dryness. The residue was purified by flash chromatography (SiO₂, cyclohexane/acetone/CH₂Cl₂ 80/10/10) to give 3,3:17,17-bis(ethylendioxy)-5α-hydroxyandrostane-6-one (1.56 g, 55%). ¹H-NMR (300 MHz, acetone-d₆, ppm from TMS: δ 4.36 (1H, s), 4.07-3.74 (8H, m), 2.64 (1H, m), 2.10-1.17 (18H, m), 0.82 (3H, s), 0.78 (3H, s).

To a stirred suspension of methyltriphenylphosphonium bromide (14.1 g) in dry THF (240 mL) cooled at 0° C. under N₂, potassium tert-butoxide (4.31 g) was added. After stirring for 10 min, a solution of 3,3:17,17-bis(ethylendioxy)-5α-hydroxyandrostane-6-one (4.00 g) in dry THF (77 mL) was added dropwise at room temperature over 0.5 h. After 2 h at room temperature, the mixture was quenched by addition of 5% NaH₂PO₄ aqueous solution and extracted with EtOAc (2×100 mL). The combined organic extracts were washed with 5% NaH₂PO₄ aqueous solution, brine, dried over Na₂SO₄ and evaporated to dryness. The residue was purified by flash chromatography (SiO₂, n-hexane/CH₂Cl₂/acetone 80/10/10) to give 3,3:17,17-bis(ethylendioxy)-5α-hydroxy-6-methyleneandrostane (2.40 g, 60%). ¹H-NMR (300 MHz, DMSO-d₆, ppm from TMS): δ 4.71 (1H, bs), 4.51 (1H, bs), 4.12 (1H, s), 3.95-3.65 (8H, m), 2.10-1.10 (18H, m), 0.72 (3H, s), 0.70 (3H, s).

The title compound II-ap was prepared in 85% yield from 3,3:17,17-bis(ethylendioxy)-5α-hydroxy-6-methyleneandrostane by the procedure described above for the preparation of 6-methyleneandrostane-3,17-dione (II-ac, Prepn. 13). The combined organic extracts were washed with H₂O, dried over Na₂SO₄ and evaporated to dryness. The residue was purified by flash chromatography (SiO₂, n-hexane/AcOEt 60/40). ¹H-NMR (300 MHz, DMSO-d₆, ppm from TMS): δ 4.91 (1H, s), 4.81 (1H, bs), 4.58 (1H, bs), 2.82 (1H, d), 2.42-1.10 (17H, m), 0.94 (3H, s), 0.77 (3H, s).

PREPARATION 27

5α-Hydroxy-6-(E)-hydroxyiminoandrostane-3,17-dione (I-aq)

3,3:17,17-Bis(ethylendioxy)-5α-hydroxy-6-(E)-hydroxyimino-androstane was prepared in 85% yield from 3,3:17,17-bis(ethylendioxy)-5α-hydroxyandrostan-6-one (Prepn. 26) by the procedure described above for the preparation of 6-(E)-hydroxyiminoandrostane-3,17-dione (II-ah, Prepn. 18). The crude was purified by flash chromatography (SiO₂, cyclohexane/acetone/CH₂Cl₂ 70/15/15). ¹H-NMR (300 MHz, DMSO-d₆, ppm from TMS: δ 10.45 (1H, s), 4.33 (1H, s), 3.96-3.69 (8H, m), 2.96 (1H, dd), 2.02-1.08 (18H, m), 0.74 (3H, s), 0.71 (3H, s).

The title compound II-aq was prepared in 80% yield from 3,3:17,17-bis(ethylendioxy)-5α-hydroxy-6-(E)-hydroxyiminoandrostane by the procedure described above for the preparation of 6-methyleneandrostane-3,17-dione (I-ac, Prepn. 13). The combined organic extracts were washed with H₂O, dried over Na₂SO₄ and evaporated to dryness. The residue was purified by flash chromatography (SiO₂, n-hexane/acetone/CH₂Cl₂ 60/20/20). ¹H-NMR (300 MHz, acetone-d₆, ppm from TMS): δ 10.72 (1H, s), 5.35 (1H, s), 3.12 (1H, dd), 2.85-1.09 (18H, m), 0.94 (3H, s), 0.78 (3H, s).

PREPARATION 28

5α-Hydroxy-6-(E)-methoxyiminoandrostane-3,17-dione (II-ar)

3,3:17,17-Bis(ethylendioxy)-5α-hydroxy-6-(E)-methoxyimino-androstane was prepared in 85% yield from 3,3:17,17-bis(ethylendioxy)-5α-hydroxyandrostane-6-one (Prepn. 26) by the procedure described above for the preparation of 6-(E)-hydroxyiminoandrostane-3,17-dione (II-ah, Prepn. 18). The crude was purified by flash chromatography (SiO₂, cyclohexane/Acetone/CH₂Cl₂ 70/15/15). ¹H-NMR (300 MHz, DMSO-d₆, ppm from TMS): δ 4.42 (1H, s), 3.95-3.75 (8H, m), 3.70 (3H, s), 2.87 (1H, dd), 2.00-1.10 (18H, m), 0.74 (3H, s), 0.72 (3H, s).

The title compound II-ar was prepared in 80% yield from 3,3:17,17-bis(ethylendioxy)-5α-hydroxy-6-(E)-methoxyiminoandrostane by the procedure described above for the preparation of 6-methyleneandrostane-3,17-dione (II-ac, Prepn. 13). The combined organic extracts were washed with H$_2$O, dried over Na$_2$SO$_4$ and evaporated to dryness. The residue was purified by flash chromatography (SiO$_2$, n-hexane/acetone/CH$_2$Cl$_2$ 60/20/20). $^1$H-NMR (300 MHz, DMSO-d$_6$, ppm from TMS): δ 5.46 (1H, s), 3.75 (3H, s), 3.20-2.93 (1H, dd), 2.86-2.75 (1H, d), 2.30-1.10 (17H, m), 0.96 (3H, s), 0.77 (3H, s).

PREPARATION 29

Androstane-3,7,17-trione (II-as)

A mixture of 3β-acetoxyandrost-5-ene-7,17-dione (7.97 g) and 10% Pd/C (0.80 g) in EtOH (0.5 L) was stirred under H$_2$ at atm pressure for 2 h. The mixture was filtered through Celite and the filtrate evaporated to dryness. The crude product was crystallized from Et$_2$O to give 3β-acetoxyandrostane-7,17-dione (4.75 g, 60%) $^1$H-NMR (300 MHz, acetone-d$_6$, ppm from TMS): δ 4.57 (1H, m), 2.66-0.96 (20H, m), 1.96 (3H, s), 1.05 (3H, s), 0.77 (3H, s).

To a solution of 3β-acetoxyandrostane-7,17-dione in MeOH (156 mL), 5N NaOH (54 mL) was added. After stirring at room temperature for 10 min the solution was evaporated and the residue extracted with CH$_2$Cl$_2$ (2×). The combined organic extracts were washed with brine, dried over Na$_2$SO$_4$, filtered and evaporated to dryness to give 3β-hydroxyandrostane-7,17-dione (1.70 g, 95%). $^1$H-NMR (300 MHz, acetone-d$_6$, ppm from TMS): δ 4.56 (1H, d), 3.35 (1H, m), 2.66-0.87 (20H, m), 1.02 (3H, s), 0.76 (3H, s).

To a stirred solution of 3β-hydroxyandrostane-7,17-dione (1.60 g), TPAP (0.09 mg), NMNO (1.43 g) under N$_2$ in CH$_2$Cl$_2$ (100 mL), molecular sieve type 4 Å powder (2.6 g) was added. After 0.5 h the mixture was filtered and the filtrate was purified by flash chromatography (SiO$_2$, CH$_2$Cl$_2$) to give the title compound II-as (1.29 g, 81%). $^1$H-NMR (300 MHz, acetone-d$_6$, ppm from TMS): δ 2.82-1.12 (20H, m), 1.39 (3H, s), 0.88 (3H, s).

PREPARATION 30

7-(E)-Hydroxyiminoandrostane-3,17-dione (II-at)

3,3:17,17-Bis(ethylendioxy)androstane-7-one was prepared in 82% yield from 3,3:17,17-bis(ethylendioxy)-5-androsten-7-one by the procedure described above for the preparation of 3β-acetoxyandrostane-7,17-dione (Prepn. 29) using EtOAc instead of EtOH. The crude product was purified by flash chromatography (SiO$_2$, n-hexane/EtOAc 6/4). $^1$H-NMR (300 MHz, acetone-d$_6$, ppm from TMS: δ 3.96-3.75 (8H, m), 2.54-1.10 (20H, m), 1.13 (3H, s), 0.83 (3H, s).

3,3:17,17-Bis(ethylendioxy)-7-(E)-hydroxyiminoandrostane was prepared in 95% yield from 3,3:17,17-bis(ethylendioxy)androstan-7-one by the procedure described above for the preparation of 3,3:17,17-bis(ethylendioxy)-6-(E)-hydroxyiminoandrostane (Prepn. 18). The crude product was purified by flash chromatography (SiO$_2$, CH$_2$Cl$_2$/MeOH 9/1). $^1$H-NMR (300 MHz, DMSO-d$_6$, ppm from TMS): δ 10.17 (1H, s), 3.88-3.70 (8H, m), 2.89 (1H, m), 2.23-0.71 (19H, m), 0.90 (3H, s), 0.77 (3H, s).

The title compound II-at was prepared in 50% yield from 3,3:17,17-bis(ethylendioxy)-7-(E)-hydroxyiminoandrostane by the procedure described above for the preparation of 6-methyleneandrostane-3,17-dione (II-ac, Prepn. 13). The combined organic extracts were washed with H$_2$O, dried over Na$_2$SO$_4$ and evaporated to dryness. The crude product was purified by flash chromatography (SiO$_2$, n-hexane/EtOAc 6/4). $^1$H-NMR (300 MHz, DMSO-d$_6$, ppm from TMS: δ 10.37 (1H, s), 2.99 (1H, m), 2.58-0.67 (19H, m), 1.12 (3H, s), 0.82 (3H, s).

PREPARATION 31

7-(E)-Methoxyiminoandrostane-3,17-dione (II-au)

3,3:17,17-Bis(ethylendioxy)-7-(E)-methoxyiminoandrostane was prepared in 90% yield from 3,3:17,17-bis(ethylendioxy)androstan-7-one by the procedure described above for the preparation of 3,3:17,17-bis(ethylendioxy)-6-(E)-hydroxyiminoandrostane (Prepn. 18). The crude product was purified by flash chromatography (SiO$_2$, CH$_2$Cl$_2$/MeOH 9/1). $^1$H-NMR (300 MHz, DMSO-d$_6$, ppm from TMS: δ 3.88-3.70 (8H, m), 3.69 (3H, s), 2.79 (1H, m), 2.28-0.72 (19H, m), 0.89 (3H, s), 0.77 (3H, s).

The title compound II-au was prepared in 55% yield from 3,3:17,17-bis(ethylendioxy)-7-(E)-methoxyiminoandrostane by the procedure described above for the preparation of 6-methyleneandrostane-3,17-dione (II-ac, Prepn. 13). The crude product was purified by flash chromatography (SiO$_2$, n-hexane/EtOAc 6/4). $^1$H-NMR (300 MHz, DMSO-d$_6$, ppm from TMS): δ 3.72 (3H, s), 2.89 (1H, m), 2.63-0.93 (19H, m), 1.12 (3H, s), 0.82 (3H, s).

PREPARATION 32

7-(E)-Allyloxyiminoandrostane-3,17-dione (II-av)

3,3:17,17-Bis(ethylendioxy)-7-(E)-allyloxyiminoandrostane was prepared in 86% yield from 3,3:17,17-bis(ethylendioxy)androstane-7-one by the procedure described above for the preparation of 3,3:17,17-bis(ethylendioxy)-6-(E)-hydroxyiminoandrostane (Prepn. 18). The crude product was purified by flash chromatography (SiO$_2$, n-hexane/EtOAc 6/4). $^1$H-NMR (300 MHz, acetone-d$_6$, ppm from TMS): δ 5.98 (1H, m), 5.23 (1H, m), 5.12 (1H, m), 4.48 (2H, ddd), 3.97-3.88 (8H, m), 2.98 (1H, m), 2.32 (1H, m), 2.24 (1H, t), 2.00-1.00 (16H, m), 1.00 (3H, s), 0.95 (1H, m), 0.85 (3H, s).

The title compound II-av was prepared in 76% yield from 3,3:17,17-bis(ethylendioxy)-7-(E)-allyloxyiminoandrostane by the procedure described above for the preparation of 6-methyleneandrostane-3,17-dione (II-ac, Prepn. 13). The crude product was purified by flash chromatography (SiO$_2$, n-hexane/EtOAc 8/2). $^1$H-NMR (300 MHz, DMSO-d$_6$, ppm from TMS): δ 5.98 (1H, m), 5.24 (1H, m), 5.14 (1H, m), 4.48 (2H, m), 2.40-1.10 (20H, m), 1.00 (3H, s), 0.81 (3H, s).

PREPARATION 33

7-Methyleneandrostane-3,17-dione (II-aw)

The 3,3:17,17-Bis(ethylendioxy)-7-methyleneandrostane was prepared in 85% yield from 3,3:17,17-bis(ethylendioxy)androstane-7-one by the procedure described above for the preparation of 3,3:17,17-bis(ethylendioxy)-6-methyleneandrostane (Prepn. 13). The combined organic extracts were washed with H$_2$O, dried over Na$_2$SO$_4$ and evaporated to dryness. $^1$H-NMR (300 MHz, acetone-d$_6$, ppm from TMS): δ 4.67 (1H, m), 4.60 (1H, m), 3.86 (8H, m), 2.20-1.10 (20H, m), 0.97 (3H, s), 0.86 (3H, s).

The title compound II-aw was prepared in 87% yield from 3,3:17,17-bis(ethylendioxy)-7-methyleneandrostane by the procedure described above for the preparation of 6-methyleneandrostane-3,17-dione (I-ac, Prepn. 13). The combined organic extracts were washed with H$_2$O, dried over Na$_2$SO$_4$ and evaporated to dryness. $^1$H-NMR (300 MHz, DMSO-d$_6$, ppm from TMS): δ 4.70 (1H, m), 4.62 (1H, m), 2.20-1.10 (20H, m), 1.00 (3H, s), 0.88 (3H, s).

PREPARATION 34

7α-Hydroxymethylandrostane-3,17-dione (II-av) and 7β-hydroxymethylandrostane-3,17-dione (II-aw)

3,3:17,17-bis(ethylendioxy)-7α-hydroxymethylandrostane and 3,3:17,17-bis(ethylendioxy)-7β-hydroxymethylandrostane were prepared in 10% and 70% yield, respectively, from 3,3:17,17-bis(ethylendioxy)-7-methyleneandrostane (Prepn. 33, 2.9 g) by the procedure described above for the preparation of 3,3:17,17-bis(ethylendioxy)-6α-hydroxymethyl-androstane (Prepn. 14). The residue was purified by flash chromatography (SiO$_2$, n-hexane/EtOAc 60/40). 3,3:17,17-bis(ethylendioxy)-7α-hydroxymethylandrostane $^1$H-NMR (300 MHz, acetone-d$_6$, ppm from TMS): δ 3.85-3.75 (8H, m), 3.67 (2H, m), 3.34 (1H, t), 2.00-0.90 (21H, m), 0.87 (3H, s), 0.81 (3H, s) 3,3:17,17-bis(ethylendioxy)-7β-hydroxymethylandrostane $^1$H-NMR (300 MHz, acetone-d$_6$, ppm from TMS): δ 3.90-3.75 (8H, m), 3.58 (2H, m), 3.31 (1H, t), 2.00-1.10 (21H, m), 0.84 (3H, s), 0.81 (3H, s).

7α-Hydroxymethylandrostane-3,17-dione II-av was prepared in 85% yield from 3,3:17,17-bis(ethylendioxy)-7α-hydroxymethyl-androstane by the procedure described above for the preparation of 6-methyleneandrostane-3,17-dione (I-ac, Prepn. 13). The combined organic extracts were washed with H$_2$O, dried over Na$_2$SO$_4$ and evaporated to dryness. $^1$H-NMR (300 MHz, acetone-d$_6$, ppm from TMS): δ 3.71 (2H, m), 3.30 (1H, t), 2.50-1.25 (21H, m), 1.12 (3H, s), 0.85 (3H, s).

7β-Hydroxymethylandrostane-3,17-dione II-aw was prepared in 85% yield from 3,3:17,17-bis(ethylendioxy)-7β-hydroxymethylandrostane by the procedure described above for the preparation of 6-methyleneandrostane-3,17-dione (II-ac, Prepn. 13). The combined organic extracts were washed with H$_2$O, dried over Na$_2$SO$_4$ and evaporated to dryness. $^1$H-NMR (300 MHz, acetone-d$_6$, ppm from TMS): δ 3.70-3.60 (2H, m), 3.54 (1H, t), 2.50-0.90 (21H, m), 1.06 (3H, s), 0.86 (3H, s).

PREPARATION 35

7α-Hydroxyandrostane-3,17-dione (II-ax)

To a stirred solution of 3,3:17,17-bis(ethylendioxy)androstane-7-one (Prepn. 30, 762 mg) in dry THF (21 mL) at −78° C. under N$_2$, 1M lithium selectride in THF (2.34 mL) was added. After completing the addition, the mixture was stirred at −70° C. for 0.5 h. H$_2$O (7.8 mL) was cautiously added dropwise followed by 6N NaOH (18.7 mL) and 9.8 M H$_2$O$_2$ (3.0 mL). After stirring at room temperature for 1 h, brine (20 mL) was added. The mixture was extracted with CH$_2$Cl$_2$ (2×20 mL). The combined organic extracts were washed with brine, dried over Na$_2$SO$_4$, filtered and evaporated to dryness. The residue was purified by flash chromatography (SiO$_2$, n-hexane/EtOAc 60/40) to give 3,3:17,17-bis(ethylendioxy)-7α-hydroxyandrostane (578.6 mg, 75%). $^1$H-NMR (300 MHz, DMSO-d$_6$, ppm from TMS): δ 4.16 (1H, d), 3.85-3.65 (8H, m), 3.59 (1H, m), 2.00-1.00 (20H, m), 0.72 (6H, s).

The title compound II-ax was prepared in 89% yield from 3,3:17,17-bis(ethylendioxy)-7α-hydroxyandrostane by the procedure described above for the preparation of 6-methyleneandrostane-3,17-dione (II-ac, Prepn. 13). The combined organic extracts were washed with H$_2$O, dried over Na$_2$SO$_4$ and evaporated to dryness. $^1$H-NMR (300 MHz, dmso-d$_6$, ppm from TMS): δ 4.32 (1H, bb), 3.75 (1H, m), 2.40-1.00 (20H, m), 0.96 (3H, s), 0.78 (3H, s).

PREPARATION 36

7α-Methylandrostane-3,17-dione (II-ay)

To a solution of DABCO (70 mg) in dry CH$_2$Cl$_2$ (3 mL) at 0° C. 3,3:17,17-bis(ethylendioxy)-7α-hydroxymethylandrostane (Prepn. 34, 90 mg) was added, followed by the addition of 4-toluenesulfonyl chloride (90 mg). After stirring overnight at room temperature, the precipitate was filtered, washed with CH$_2$Cl$_2$. The filtrate was evaporated to dryness and the residue purified by flash chromatography (SiO$_2$, cyclohexane/AcOEt 80/20) to give 3,3:17,17-bis(ethylendioxy)-7α-[4-methyl(benzenesulfonyloxy)methyl]androstane (86 mg, 70%). $^1$H-NMR (300 MHz, DMSO-d$_6$, ppm from TMS): δ 7.78 (2H, m), 7.49 (2H, m), 4.12 (1H, dd), 3.99 (1H, dd), 3.87-3.67 (8H, m), 2.42 (3H, s), 1.90-1.00 (21H, m), 0.73 (3H, s), 0.69 (3H, s).

To a solution of NaBH$_4$ (30 mg) in DMSO (6 mL) 3,3:17,17-bis(ethylendioxy)-7α-[4-methyl(benzenesulfonyloxy)methyl]androstane (70 mg) was added and the mixture was stirred at room temperature for 6 hrs. H$_2$O was added and the mixture extracted with Et$_2$O (2×). The combined organic extracts were washed with H$_2$O, brine, dried over Na$_2$SO$_4$, filtered and evaporated to dryness. The residue was purified by flash chromatography (SiO$_2$, cyclohexane/Et$_2$O 75/25) to give 3,3:17,17-bis(ethylendioxy)-7α-methylandrostane (34 mg, 70%). $^1$H-NMR (300 MHz, acetone-d$_6$, ppm from TMS): δ 3.85-3.75 (8H, m), 2.00-1.00 (21H, m), 0.92 (3H, d), 0.83 (3H, s), 0.80 (3H, s).

7α-Methylandrostane-3,17-dione II-ay was prepared in 90% yield from 3,3:17,17-bis(ethylendioxy)-7α-methylandrostane by the procedure described above for the preparation of 6-methyleneandrostane-3,17-dione (II-ac, Prepn. 13). The combined organic extracts were washed with H$_2$O, dried over Na$_2$SO$_4$ and evaporated to dryness. $^1$H-NMR (300 MHz, acetone-d$_6$, ppm from TMS): δ 2.50-1.17 (21H, m), 1.10 (3H, s), 0.97 (3H, d), 0.87 (3H, s).

PREPARATION 37

7β-Methylandrostane-3,17-dione (II-az)

A mixture of 3,3:17,17-bis(ethylendioxy)-7-methyleneandrostane (Prepn. 33, 520 mg) and (1,5-cyclooctadiene)(pyridine)(tricyclo hexylphosphine)iridium(1)hexafluoro-phosphate (crabtree catalyst) (75 mg) in CH$_2$Cl$_2$ (52 mL) was stirred under H$_2$ at atm pressure for 4 h. The mixture was evaporated to dryness and purified by flash chromatography (SiO$_2$, n-hexane/EtOAc 85/15) to give 3,3:17,17-bis(ethylendioxy)-7β-methylandrostane (287.5 mg, 55%). $^1$H-NMR (300 MHz, acetone-d$_6$, ppm from TMS): δ 3.80-3.60 (8H, m), 2.00-1.00 (20H, m), 0.97 (3H, d), 0.89 (3H, s), 0.80 (3H, s), 0.73 (1H, m).

The title compound II-az was prepared in 90% yield from 3,3:17,17-bis(ethylendioxy)-7β-methylandrostane by the procedure described above for the preparation of 6-methyleneandrostane-3,17-dione (II-ac, Prepn. 13). The combined organic extracts were washed with H$_2$O, dried over Na$_2$SO$_4$ and evaporated to dryness. $^1$H-NMR (300 MHz, DMSO-d$_6$, ppm from TMS): δ 2.50-1.10 (20H, m), 1.07 (3H, d), 1.06 (3H, s), 0.89 (1H, m), 0.88 (3H, s).

PREPARATION 38

7-(Spirocyclopropane)androstane-3,17-dione (II-ba)

The title compound II-ba was prepared in 45% yield from 3,3:17,17-bis(ethylendioxy)-7-methyleneandrostane (Prepn. 35) by the procedure described above for the preparation of 6-(spirocyclopropane)androstane-3,17-dione (II-al, Prepn. 22). The residue was purified by flash chromatography (SiO$_2$, n-hexane/EtOAc/acetone 10/1/1). $^1$H-NMR (300 MHz, acetone-d$_6$, ppm from TMS): δ 2.52-0.84 (20H, m), 1.16 (3H, s), 0.87 (3H, s), 0.60 (1H, m), 0.42 (1H, m), 0.35 (1H, m), −0.09 (1H, m).

PREPARATION 39

7α-Formamidomethylandrostane-6,17-dione (II-bb)

3,3:17,17-Bis(ethylendioxy)-7α-aminoandrostane was prepared from 3,3:17,17-bis(ethylendioxy)-7-(E)-hydroxy-iminoandrostane (Prepn. 30, 1.61 g) by the procedure described above for the preparation of 3,3:17,17-bis(ethylendioxy)-6α-aminoandrostane (Prepn. 20). The combined organic extracts were washed with H$_2$O, dried over Na$_2$SO$_4$ and evaporated to dryness. The crude product was purified by flash chromatography (SiO$_2$, CH$_2$Cl$_2$/MeOH/NH$_4$OH 90/10/1) to give a mixture of 3,3:17,17-bis(ethylendioxy)-7α-aminoandrostane and 3,3:17,17-bis(ethylendioxy)-7β-aminoandrostane (1.19 g, 35/65 mixture).

To a stirred solution of a 35/65 mixture of 3,3:17,17-bis(ethylendioxy)-7α-aminoandrostane and 3,3:17,17-bis(ethylendioxy)-7β-aminoandrostane (1.17 g) under N$_2$ in CH$_2$Cl$_2$ (35 mL) at 0° C. Et$_3$N (1.67 mL) and 9-fluorenylmethoxycarbonyl chloride (1.39 g) were added. After stirring overnight at room temperature, water was added and the mixture extracted with CH$_2$Cl$_2$. The organic phase was washed with 5% NaHCO$_3$ dried over Na$_2$SO$_4$ and evaporated to dryness. The residue was purified by flash chromatography (SiO$_2$; n-hexane/EtOAc 70/30) to give [3,3:17,17-bis(ethylendioxy)-androstane-7α-yl]carbamic acid 9H-fluoren-9-ylmethyl ester (505 mg, 28%) $^1$H-NMR (300 MHz, DMSO-d$_6$, ppm from TMS): δ 7.90 (2H, m), 7.71 (2H, m), 7.54 (1H, m), 7.43-7.22 (4H, m), 4.50-4.10 (3H, m), 3.90-3.80 (8H, m), 3.66 (1H, m), 1.90-0.80 (19H, m), 0.77 (6H, s), 0.70-0.65 (1H, m).

To a stirred solution of [3,3:17,17-bis(ethylendioxy)androstane-7α-yl]carbamic acid 9H-fluoren-9-ylmethyl ester (464 mg) in dry THF (29 mL) at 0° C., 1M tetrabutylammonium fluoride in THF (1.13 mL) was added. After completing the addition, the mixture was stirred at room temperature for 4 h. The solution was concentrated to small volume and purified by flash chromatography (SiO$_2$, CH$_2$Cl$_2$/MeOH/26% NH$_4$OH 92/8/0.8) to give 3,3:17,17-bis(ethylendioxy)-7α-aminomethylandrostane (247 mg, 84%). $^1$H-NMR (300 MHz, DMSO-d$_6$, ppm from TMS): δ 3.82-3.65 (8H, m), 2.81 (1H, m), 1.90-1.00 (22H, m), 0.77 (3H, s), 0.75 (3H, s).

3,3:17,17-Bis(ethylendioxy)-7α-formamidoandrostane was prepared in 92% yield from 3,3:17,17-bis(ethylendioxy)-7α-aminomethylandrostane by the procedure described above for the preparation of 3,3:17,17-bis(ethylendioxy)-6α-formamidoandrostane (Prepn. 20). $^1$H-NMR (300 MHz, DMSO-d$_6$, ppm from TMS): δ 8.10 (1H, m), 7.98 (1H, m), 4.05 (1H, m), 3.89-3.20 (8H, m), 1.93-0.50 (20H, m), 0.80 (3H, s), 0.78 (3H, s)

The title compound II-bb was prepared in 97% yield from 3,3:17,17-bis(ethylendioxy)-7α-formamido androstane by the procedure described above for the preparation of 6-methyleneandrostane-3,17-dione (II-ac, Prepn. 13). The crude product was purified by flash chromatography (SiO$_2$, n-hexane/Acetone 70/30). $^1$H-NMR (300 MHz, DMSO-d$_6$, ppm from TMS): δ 8.10 (1H, m), 7.98 (1H, m), 4.05 (1H, m), 2.50-0.70 (20H, m), 1.02 (3H, s), 0.80 (3H, s).

PREPARATION 40

7α-Methoxycarbonylandrostane-3,17-dione (II-bc)

3,3:17,17-bis(ethylendioxy)-7α-hydroxymethylandrostane was obtained (2.86 g, 95%) by the procedure described above for the preparation of 3,3:17,17-bis(ethylendioxy)-6-hydroxymethylandrostane (Prepn. 14) starting from 3,3:17, 17-bis(ethylendioxy)-7-methylene-androstane (Prepn. 33, 2.89 g). The combined organic extracts were washed with brine, dried over Na$_2$SO$_4$, filtered and evaporated to dryness. The residue was purified by flash chromatography (SiO$_2$, n-hexane/EtOAc 45/55). $^1$H-NMR (300 MHz, acetone-d$_6$, ppm from TMS): δ 3.90-3.70 (8H, m), 3.50 (2H, m), 3.35 (1H, t), 2.05-0.66 (21H, m), 0.83 (3H, s), 0.80 (3H, s).

To a solution of 3,3:17,17-bis(ethylendioxy)-7α-hydroxymethyl-androstane (2.86 g) in DMSO (30 mL), IBX (3.95 g) was added and stirred at room temperature for 1 h. The mixture was quenched by addition of H$_2$O (150 mL) and Et$_2$O (150 mL). After stirring for 15 min, the mixture was filtered and the cake was washed with Et$_2$O. The layers were separated and the aqueous phase was extracted with Et$_2$O (3×). The combined organic extracts were washed with brine, dried over Na$_2$SO$_4$ and evaporated to dryness. The residue was purified by flash chromatography (SiO$_2$, n-hexane/EtOAc 75/35) to give 3,3:17,17-bis(ethylendioxy)-7α-formylandrostane (2.36 g, 83%). $^1$H-NMR (300 MHz, acetone-d$_6$, ppm from TMS): δ 9.96 (1H, d), 3.95-3.75 (8H, m), 2.50 (1H, m), 2.30-0.69 (20H, m), 0.89 (3H, s), 0.84 (3H, s).

7α-Formylandrostane-3,17-dione was prepared in 85% yield from 3,3:17,17-bis(ethylendioxy)-7α-formylandrostane (2.36 g) by the procedure described above for the preparation of 6-methyleneandrostane-3,17-dione (II-ac, Prepn. 13). $^1$H-NMR (300 MHz, acetone-d$_6$, ppm from TMS): δ 9.95 (1H, d), 2.57-0.80 (21H, m), 0.95 (3H, s), 0.80 (3H, s).

To a stirred suspension of 7α-formylandrostane-3,17-dione (1.77 g) in t-ButOH (35 mL) and 5% aqueous Na$_2$HPO$_4$ solution (21.5 mL), 1N aqueous KMnO$_4$ (35 mL) was added. After 5 minutes at room temperature, the mixture was quenched by addition of 40% aqueous NaHSO$_3$ solution. The suspension was filtered, washed with H$_2$O and the filtrate was freeze-dried. The residue was taken up with H$_2$O (50 mL) and extracted with EtOAc (4×70 mL). The combined organic extracts were dried over Na$_2$SO$_4$ and evaporated to dryness to give 7α-carboxyandrostane-3,17-dione (1.80 g, 96%). $^1$H-NMR (300 MHz, acetone-d$_6$, ppm from TMS): δ 12.00 (1H, bb), 2.65 (1H, m), 2.45-0.70 (20H, m), 1.00 (3H, s), 0.79 (3H, s).

To a stirred solution of 7α-carboxyandrostane-3,17-dione (680 mg) in CH$_2$Cl$_2$ (30 mL) at 0° C., MeOH (160 μL), DMAP (20 mg) and EDAC (800 mg) were added. After stirring overnight at room temperature, H$_2$O was added and the mixture was extracted with CH$_2$Cl$_2$ (2×). The combined organic extracts were washed with H$_2$O, brine, dried over Na$_2$SO$_4$, filtered and evaporated to dryness. The residue was purified by flash chromatography (SiO$_2$, n-hexane/EtOAc 60/40) to give the title compound II-bc (500 mg, 70%).

$^1$H-NMR (300 MHz, DMSO-d$_6$, ppm from TMS): δ 3.63 (3H, s), 2.85 (1H, m), 2.50-0.75 (20H, m), 1.12 (3H, s), 0.86 (3H, s).

PREPARATION 41

6-(E)-Hydroxyimino-7α-hydroxyandrostane-3,17-dione (II-bd)

A solution of chlorotrimethylsilane (3.7 mL) and LDA (15.6 mL, 1.5M in THF) in dry THF (15 mL) at −78° C. under nitrogen was added dropwise, in 30 minutes, to a solution of 3,3:17,17-bis(ethylendioxy) androstane-6-one (1.43 g) in THF (15 mL) at −78° C. After 2 h TEA (7.3 mL) was added at −20° C. followed, after 30', by the addition of solid NaHCO$_3$. After extraction with EtOAc (3×), the combined organic extracts were washed with brine (3×), dried over Na$_2$SO$_4$ and evaporated to dryness. The residue was purified by flash chromatography (SiO$_2$, cyclohexane/EtOAc 90/10) to give 3,3:17,17-bis(ethylendioxy)-6-trimethylsililoxyandrost-6-ene (1.35 g, 80%). $^1$H-NMR (300 MHz, acetone-d$_6$, ppm from TMS): δ 4.67 (1H, m), 3.94-3.76 (8H, m), 2.31 (1H, m), 2.00-0.90 (17H, m), 0.86 (3H, s), 0.83 (3H, s), 0.17 (9H, s).

To a stirred solution of 3,3:17,17-bis(ethylendioxy)-6-trimethylsililoxyandrost-6-ene (940 mg) in CH$_2$Cl$_2$ (50 mL), at −15° C. solid NaHCO$_3$ (683 mg) was added followed by the addition of mCPBA (550 mg, 70%). After 1 h TBAF (2.56 g) was added and then warmed to room temperature. After 1 h the mixture was quenched by addition of brine then extracted with CH$_2$Cl$_2$. The combined organic extracts were washed with H$_2$O, dried over Na$_2$SO$_4$ and evaporated to dryness. The residue was purified by flash chromatography (SiO$_2$, n-hexane/EtOAc 60/40) to give 3,3:17,17-bis(ethylendioxy)-7α-hydroxyandrostane-6-one (660 mg, 80%). $^1$H-NMR (300 MHz, DMSO-d$_6$, ppm from TMS): δ 5.63 (1H, d), 3.90-3.70 (8H, m), 3.53 (1H, m), 3.13 (1H, m), 2.00-1.00 (17H, m), 0.74 (3H, s), 0.62 (3H, s).

3,3:17,17-bis(ethylendioxy)-6-(E)-hydroxyimino-7α-hydroxyandrostane was obtained (628 mg, 92%) from 3,3:17,17-bis(ethylendioxy)-7α-hydroxyandrostane-6-one (660 mg) by the procedure described for the preparation of 6-(E)-hydroxyiminoandrostane-3,17-dione (II-ah, Prepn. 18). The crude product was used without purification in the next step. $^1$H-NMR (300 MHz, DMSO-d$_6$, ppm from TMS): δ 10.42 (1H, s), 4.90 (1H, d), 4.80 (1H, m), 3.90-3.75 (8H, m), 2.75 (1H, m), 1.90-1.00 (17H, m), 0.73 (3H, s), 0.61 (3H, s).

The title compound II-bd was prepared (500 mg, 60%) from 3,3:17,17-bis(ethylendioxy)-6-(E)-hydroxyimino-7α-hydroxyandrostane-6-one (628 mg) by the procedure described above for the preparation of 6-methyleneandrostane-3,17-dione (II-ac, Prepn. 13). The combined organic extracts were washed with brine, dried over Na$_2$SO$_4$ and evaporated to dryness. The residue was purified by flash chromatography (SiO$_2$, n-hexane/acetone/CH$_2$Cl$_2$ 40/30/30). $^1$H-NMR (300 MHz, DMSO-d$_6$, ppm from TMS): δ 10.76 (1H, s), 5.14 (1H, d), 5.02 (1H, m), 2.84 (1H, m), 2.70-1.10 (17H, m), 0.85 (3H, s), 0.78 (3H, s).

PREPARATION 42

6α-hydroxymethylandrostane-3,7,17-trione (II-be)

3,3:17,17-Bis(ethylendioxy)-7-trimethylsililoxyandrost-6-ene was prepared (1.82 g, 84%) from 3,3:17,17-bis(ethylendioxy)androstane-7-one (1.86 g) by the procedure described for the preparation of 3,3:17,17-bis(ethylendioxy)-6-trimethylsililoxyandrost-6-ene (Prepn. 41). The combined organic extracts were washed with H$_2$O, dried over Na$_2$SO$_4$ and evaporated to dryness. The residue was purified by flash chromatography (SiO$_2$, n-hexane/EtOAc 92/8). $^1$H-NMR (300 MHz, DMSO-d$_6$, ppm from TMS): δ 4.35 (1H, m), 3.90-3.70 (8H, m), 2.20-2.05 (1H, m), 1.90-0.90 (17H, m), 0.79 (3H, s), 0.69 (3H, s), 0.15 (9H, s).

To a solution of 2,6-diphenylphenol (3.80 g) in DCM (50 mL), trimethylaluminium (4 mL, 2 M in hexanes) was added. After 1 h the mixture was warmed to 0° C., and a solution of trioxane (231 mg) in DCM (1 mL) added. After 1 h the mixture was cooled to −78° C. and a solution of 3,3:17,17-bis(ethylendioxy)-7-trimethylsililoxyandrost-6-ene (1.21 g) in DCM (15 mL) was added, then stirred overnight at −20° C. The reaction was quenched by addition of NaHCO$_3$ saturated solution. The mixture was filtered on a celite pad and washed with DCM. The filtrate was washed with water, dried over Na$_2$SO$_4$ and evaporated to small volume. TBAF (2.8 mL, 1M in THF) was added and the mixture stirred at room temperature for 1.5 h. The olive-green solution was washed with water, dried over Na$_2$SO$_4$ and evaporated to dryness. The residue was purified by flash chromatography (SiO$_2$, n-hexane/EtOAc 30/70) to give 3,3:17,17-bis(ethylendioxy)-6α-hydroxymethylandrostane-7-one (783 mg, 72%). $^1$H-NMR (300 MHz, DMSO-d$_6$, ppm from TMS): δ 4.05 (1H, t), 3.90-3.70 (8H, m), 3.50 (2H, m), 2.45-2.28 (2H, m), 2.10-1.95 (1H, m), 1.90-1.10 (16H, m), 1.05 (3H, s), 0.75 (3H, s).

The title compound II-be was prepared (570 mg, 92%) from 3,3:17,17-bis(ethylendioxy)-6α-hydroxymethylandrostane-7-one (780 mg) by the procedure described above for the 6-methyleneandrostane-3,17-dione (II-ac, Prepn. 13). The combined organic extracts were washed with brine, dried over Na$_2$SO$_4$ and preparation of evaporated to dryness. The residue was used without purification in the next step. $^1$H-NMR (300 MHz, DMSO-d$_6$, ppm from TMS): δ 4.25 (1H, t), 3.55 (2H, m), 2.51 (2H, m), 2.10 (1H, m), 1.90-1.10 (16H, m), 0.95 (3H, s), 0.80 (3H, s).

PREPARATION 43

3β-[(R,S)-(1-tert-Butoxycarbonylpiperidin-3-yl)carbonyloxy]androstane-6,17-dione (II-bf)

To a stirred suspension of 3β-tert-butyldimethylsilyloxyandrostane-6α,17β-diol (EP 0825197 A2, 6.21 g) in DMSO (160 mL), IBX (16.45 g) was added at room temperature. After 1.5 h the mixture was quenched at room temperature by addition of H$_2$O (300 mL). After 15 min the mixture was filtered and the cake was washed with H$_2$O. The cake was extracted with Et$_2$O (4×). The combined organic extracts were dried over Na$_2$SO$_4$ and evaporated to dryness to give 3β-tert-butyldimethylsilyloxyandrostane-6,17-dione (0.36 g, 75%). $^1$H-NMR (300 MHz, DMSO-d$_6$, ppm from TMS: δ 3.54 (1H, m), 2.47-1.08 (20H, m), 0.84 (9H, s), 0.77 (3H, s), 0.66 (1H, s), 0.01 (6H, s).

To a stirred suspension of 3β-tert-butyldimethylsilyloxyandrostane-6,17-dione (2.00 g) in EtOH (20 mL), 37% HCl (40 μL) was added. After 3 h the solution was quenched with 5% aqueous NaHCO$_3$ to pH 7. The organic solvent was evaporated and the aqueous phase was extracted with CH$_2$Cl$_2$ (4×350 mL). The combined organic extracts were washed with saturated aqueous NH$_4$Cl, brine, H$_2$O, dried over Na$_2$SO$_4$ and evaporated to dryness. The residue was purified by flash chromatography (SiO$_2$, cyclohexane/EtOAc 90/10) to give 3β-hydroxyandrostane-6,17-dione (1.25 g, 86%). $^1$H-NMR (300 MHz, DMSO-d$_6$, ppm from TMS): δ 4.56 (1H, d), 3.31 (1H, m), 2.45-1.15 (20H, m), 0.77 (3H, s), 0.65 (3H, s).

A solution of 3β-hydroxyandrostane-6,17-dione (60.15 mg), EDAC (75.7 mg), 1-(tert-butoxycarbonyl)-3-piperidinecarboxylic acid (50.7 mg), DMAP (1.2 mg) in THF (1.9 mL) and H$_2$O (100 µL) was stirred overnight at room temperature. The mixture was diluted with THF, dried over Na$_2$SO$_4$ and evaporated to dryness. The residue was purified by flash chromatography (SiO$_2$, cyclohexane/EtOAc 10/90) to give the title compound II-bf (49 mg, 50%). $^1$H-NMR (300 MHz, DMSO-d$_6$, ppm from TMS): δ 4.62 (1H, m), 3.50-1.20 (29H, m), 1.35 (9H, s), 0.78 (3H, s), 0.69 (3H, s).

PREPARATION 44

3β-(N-(tert-Butoxycarbonyl)piperidin-4-ylcarbonyloxy)androstane-6,17-dione (II-bg)

Prepared in 62% yield from 3β-hydroxyandrostane-6,17-dione and 1-(tert-butoxycarbonyl)-4-piperidinecarboxylic acid by the procedure described in Prepn. 43. $^1$H-NMR (300 MHz, DMSO-d$_6$, ppm from TMS): δ 4.65 (1H, m), 3.60-1.20 (29H, m), 1.35 (9H, s), 0.78 (3H, s), 0.69 (3H, s).

PREPARATION 45

3β-(N-(tert-Butoxycarbonyl)azetidin-3-ylcarbonyloxy)androstane-6,17-dione (II-bh)

Prepared in 65% yield from 3β-hydroxyandrostane-6,17-dione and 1-(tert-butoxycarbonyl)-3-azetidinecarboxylic acid by the procedure described in Prepn. 43. $^1$H-NMR (300 MHz, DMSO-d$_6$, ppm from TMS): δ 4.66 (1H, m), 4.50-1.00 (29H, m), 1.35 (9H, s), 0.78 (3H, s), 0.69 (3H, s).

PREPARATION 46

3β-(N-(tert-Butoxycarbonyl)-pirrolidin-3R,S-ylcarbonyloxy)androstane-6,17-dione (II-bi)

Prepared in 75% yield from 3β-hydroxyandrostane-6,17-dione and 3R,S-[1-(tert-butoxycarbonyl)]pirrolidinecarboxylic acid by the procedure described in Prepn. 43. $^1$H-NMR (300 MHz, DMSO-d$_6$, ppm from TMS): δ 4.59 (1H, m), 3.45-2.85 (5H, m), 2.40-1.10 (22H, m), 0.78 (3H, s), 0.69 (3H, s).

PREPARATION 47

3β-(N-(tert-Butoxycarbonyl)morpholin-2(R,S)-lcarbonyloxy)androstane-6,17-dione (II-bj)

Prepared in 77% yield from 3β-hydroxyandrostane-6,17-dione and R,S N-(tert-butoxycarbonyl)morpholin-2-yl carboxylic acid by the procedure described in Prepn. 43. $^1$H-NMR (300 MHz, DMSO-d$_6$, ppm from TMS): δ 4.66 (1H, m), 4.15-2.50 (7H, m), 2.50-1.10 (20H, m), 1.35 (9H, s), 0.78 (3H, s), 0.69 (3H, s).

PREPARATION 48

3β-(N,N'-Bis(tert-butoxycarbonyl)piperazin-2(R,S)-ylcarbonyloxy)androstane-6,17-dione (II-bk)

Prepared in 85% yield from 3β-hydroxyandrostane-6,17-dione and R,S N,N'-bis(tert-butoxycarbonyl)piperazin-2-ylcarboxylic acid by the procedure described in Prepn. 43. $^1$H-NMR (300 MHz, DMSO-d$_6$, ppm from TMS): δ 4.72 (1H, m), 4.40-3.20 (7H, m), 2.60-1.15 (20H, m), 1.35 (18H, s), 0.78 (3H, s), 0.69 (3H, s).

PREPARATION 49

3α-Mercapto-6-methyleneandrostane-17-one (II-bl)

To a solution of triphenylphosphine (2.38 g) in THF (140 mL) cooled at 0° C., diisopropyl azodicarboxylate (1.79 mL) was added dropwise. After stirring for 30 minutes, thioacetic acid (0.65 mL) and androstane-3β,6α,17β-triol (2.00 g) were added. After 2 hrs at 0° C. and overnight at room temperature EtOAc was added. The mixture was washed with water and the organic layer evaporated to dryness. The crude product was purified by flash chromatography (SiO$_2$, cyclohexane: EtOAc 55:45) to give 3α-acetylthioandrostane-6α,17β-diol (1.60 g, 66%). $^1$H-NMR (300 MHz, DMSO-d$_6$, ppm from TMS): δ 4.42 (1H, bb), 4.28 (1H, bb), 3.91 (1H, bb), 3.42 (1H, m), 3.11 (1H, m), 2.28 (3H, s), 2.00-0.80 (20H, m), 0.74 (3H, s), 0.60 (3H, s).

To a stirred suspension of 3α-acetylthioandrostane-6α,17β-diol (1.40 g) in CH$_2$Cl$_2$ (50 mL), NMNO (1.37 g), TPAP (68 mg) and powdered molecular sieves 4 Å (2.1 g) were added at room temperature. After 2 hrs NMNO (0.7 g), TPAP (34 mg) and molecular sieves 4 Å (1 g) were added again and the reaction was stirred for further 1.5 hrs. The crude product was purified by flash chromatography (SiO$_2$, cyclohexane: EtOAc 7:3) to give 3α-acetylthioandrostane-6,17-dione (1.07 g, 76%). $^1$H-NMR (300 MHz, acetone-d$_6$, ppm from TMS): δ 3.99 (1H, bb), 2.55-1.20 (23H, m), 0.86 (3H, s), 0.79 (3H, s).

To a stirred solution of 3α-acetylthioandrostane-6,17-dione (600 mg) in THF (8 mL) cooled at −50° C., a solution of ylide prepared from methyltriphenylphosphonium bromide (1.47 g) in THF dry (8 mL) at −50° C. and potassium tert-butoxide (484 mg), was added. After 2 h the temperature was raised to room temperature. The mixture was quenched by addition of 5% NaH$_2$PO$_4$ aqueous solution and extracted with EtOAc (2×60 mL). The combined organic extracts were washed with 5% NaH$_2$PO$_4$ aqueous solution, brine, dried over Na$_2$SO$_4$, and evaporated to dryness. The residue was purified by flash chromatography (n-hexane/EtOAc 9/1) to give 3α-acetylthio-6-methyleneandrostan-17-one (210 mg, 35% yield) and 3α-mercapto-6-methyleneandrostane-17-one (208 mg, 35% yield). $^1$H-NMR (300 MHz, DMSO-d$_6$, ppm from TMS): 3α-acetylthio-6-methyleneandrostane-17-one: δ 4.73 (1H, m), 4.39 (1H, m), 3.96 (1H, m), 2.44-0.84 (20H, m), 2.29 (3H, s), 0.75 (3H, s), 0.66 (3H, s); 3α-mercapto-6-methyleneandrostane-17-one: δ 4.73 (1H, m), 4.38 (1H, m), 3.57 (1H, m), 2.52 (1H, d), 2.45-0.95 (20H, m), 0.76 (3H, s), 0.63 (3H, s).

To a solution of 3α-acetylthio-6-methyleneandrostan-17-one (210 mg) in MeOH (3 mL), 1N NaOH (0.6 mL) was added. After 1 h at room temperature 5% NaH$_2$PO$_4$ aqueous solution was added and the mixture extracted with Et$_2$O (2×20 mL). The combined organic extracts were washed with brine, dried over Na$_2$SO$_4$ and evaporated to dryness to give the title compound (185 mg, 100%).

PREPARATION 50

3α-Mercaptoandrostane-6,17-dione (II-bm)

To a suspension of 3α-acetylthioandrostane-6,17-dione (1.07 g) in MeOH (30 mL), sodium propanethiolate (0.28 g) was added and the reaction stirred for 20 minutes at room temperature. The mixture was neutralized with 1N HCl. Water was added and the mixture extracted with EtOAc. The organic layer was separated, washed with brine, and dried over $Na_2SO_4$ and evaporated to dryness to give 3α-mercaptoandrostane-6,17-dione (943 mg, 100%), used without further purification. $^1$H-NMR (300 MHz, DMSO-$d_6$, ppm from TMS): δ 3.54 (1H, m), 2.77 (1H, m), 2.54 (1H, d), 2.45-1.10 (19H, m), 0.78 (3H, s), 0.66 (3H, s).

PREPARATION 51

3α-[1-(tert-Butoxycarbonyl)pyrrolidin-3-(S)-yl]-(Z)-vinyl]androstane-6,17-dione (II-bn)

Following the procedure described in EP 0825197 A2 and starting from androstane-3,6,17-trione (3.90 g), 3β-formylandrostane-6,17-dione (2.40 g, 62%) and of 3α-formylandrostane-6,17-dione (0.78 g, 20%) were obtained after separation by flash chromatography ($SiO_2$; $CH_2Cl_2$:EtOAc 9:1). $^1$H-NMR (300 MHz, DMSO-$d_6$, ppm from TMS): β-isomer: δ 9.57 (1H, d), 2.45-1.10 (21H, m), 0.78 (3H, s), 0.63 (3H, s); α-isomer: δ 9.56 (1H, bs), 2.60-0.95 (21H, m), 0.76 (3H, s), 0.60 (3H, s).

Following the procedure described in US 006100279A and starting from 3α-formylandrostane-6,17-dione (117 mg) and [3-(S)-1-(tert-butoxycarbonyl)-3-pyrrolidinylmethyl]triphenylphosphonium iodide (Prepn. 52, 318 mg), the title compound II-bn was obtained after flash chromatography ($SiO_2$, EtOAc/n-hexane 1/1) in 73% yield. $^1$H-NMR (300 MHz, acetone-$d_6$, ppm from TMS): δ 5.82 (1H, t), 5.25 (1H, t), 3.55-3.05 (4H, m), 3.00-2.05 (7H, m), 2.00-1.10 (26H, m), 0.86 (3H, s), 0.78 (3H, s).

PREPARATION 52

[3-(S)-1-(tert-Butoxycarbonyl)-3-pyrrolidinylmethyl]triphenylphosphonium iodide

Following the procedure described in US 006100279A and starting from (S)-1-(tert-butoxycarbonyl)-2-pyrrolidinemethanol (1.1 g), the title compound was obtained (1.50 g) as a white powder. $^1$H-NMR (300 MHz, DMSO-$d_6$, ppm from TMS): δ 7.95-7.60 (15H, m), 3.95-3.65 (2H, m), 3.10-2.60 (3H, m), 1.90-1.70 (1H, m), 1.60-1.40 (1H, m), 1.30 (11H, m).

PREPARATION 53

3α-[1-(tert-Butoxycarbonyl)pyrrolidin-3-(R)-yl]-(Z)-vinyl]androstane-6,17-dione (II-bo)

Following the procedure described in US 006100279A and starting from 3α-formylandrostane-6,17-dione (II-bp, Prepn. 51, 50 mg) and [3-(R)-1-(tert-butoxycarbonyl)-3-pyrrolidinylmethyl]triphenylphosphonium iodide (II-br, Prepn. 56, 136 mg), the title compound II-bo was obtained after flash chromatography ($SiO_2$, EtOAc/n-hexane 1/1), in 62% yield. $^1$H-NMR (300 MHz, acetone-$d_6$, ppm from TMS): δ 5.80 (1H, t), 5.20 (1H, t), 3.55-3.05 (4H, m), 3.00-2.05 (7H, m), 2.00-1.10 (26H, m), 0.85 (3H, s), 0.77 (3H, s).

PREPARATION 54

[3-(R)-1-(tert-Butoxycarbonyl)-3-pyrrolidinylmethyl]triphenylphosphonium iodide

Following the procedure described in US 006100279A and starting from (R)-1-(tert-butoxycarbonyl)-2-pyrrolidinemethanol (1.10 g), the title compound was obtained (1.00 g) as a viscous oil. $^1$H-NMR (300 MHz, DMSO-$d_6$, ppm from TMS): δ 7.95-7.60 (15H, m), 3.95-3.65 (2H, m), 3.10-2.60 (3H, m), 1.90-1.70 (1H, m), 1.60-1.40 (1H, m), 1.30 (11H, m).

PREPARATION 55

3α-[1-(tert-Butoxycarbonyl)pyperidin-4-yl]-(Z)-vinyl]androstane-6,17-dione (II-bp)

Following the procedure described in US 006100279A and starting from 3α-formylandrostane-6,17-dione (Prepn. 51, 66 mg) and [1-(tert-butoxycarbonyl)-4-pyperidinylmethyl]triphenylphosphonium iodide (Prepn. 56, 189 mg), the title compound was obtained after flash chromatography ($SiO_2$, EtOAc/n-hexane 1/1), in 50% yield. $^1$H-NMR (300 MHz, acetone-$d_6$, ppm from TMS): δ 5.74 (1H, t), 5.19 (1H, t), 4.20-3.95 (2H, m), 3.00-1.05 (37H, m), 0.85 (3H, s), 0.77 (3H, s).

PREPARATION 56

[1-(tert-Butoxycarbonyl)-4-piperidinylmethyl]triphenylphosphonium iodide

Following the procedure described in US 006100279A and starting from 1-(tert-butoxy carbonyl)-4-piperidinemethanol (2.00 g), the title compound was obtained (3.00 g) as a white powder. $^1$H-NMR (300 MHz, DMSO-$d_6$, ppm from TMS): δ 7.95-7.60 (15H, m), 3.80-3.50 (4H, m), 2.70-2.50 (2H, m), 2.00-1.80 (1H, m), 1.50-1.30 (11H, m), 1.30-1.10 (2H, m).

PREPARATION 57

3α-[1-(tert-Butoxycarbonyl)azetidin-3-yl)-(Z)-vinyl]androstane-6,17-dione (II-bq)

Following the procedure described in US 006100279A and starting from 3α-formylandrostane-6,17-dione (Prepn. 51, 100 mg) and [1-(tert-butoxycarbonyl)-3-azetidinylmethyl]triphenylphosphonium iodide (Prepn. 58, 265 mg), the title compound was obtained after flash chromatography ($SiO_2$, EtOAc/n-hexane 1/1) in 70% yield. $^1$H-NMR (300 MHz, acetone-$d_6$, ppm from TMS): δ 5.82 (1H, t), 5.65 (1H, t), 4.15-3.95 (2H, m), 3.65-3.45 (3H, m), 2.60-1.10 (30H, m), 0.86 (3H, s), 0.77 (3H, s).

PREPARATION 58

[1-(tert-Butoxycarbonyl)-3-azetidinylmethyl]triphenylphosphonium iodide

Following the procedure described in US 006100279A and starting from 1-(tert-butoxycarbonyl)-3-azetidinemethanol (600 mg), the title compound was obtained (1.10 g) as a white powder. $^1$H-NMR (300 MHz, DMSO-$d_6$, ppm from TMS): δ 7.95-7.60 (15H, m), 4.10-3.90 (2H, m), 3.75-3.60 (2H, m), 3.50-3.30 (2H, m), 3.10-2.90 (1H, m), 1.35 (9H, s).

PREPARATION 59

6α-Hydroxymethyl-7α-hydroxyandrostane-3,17-dione (II-br)

To a stirred solution of 3,3:17,17-bis(ethylendioxy)-6α-hydroxymethylandrostane-7-one (Prepn. 42) (2.00 g) in MeOH (100 mL) NaBH$_4$ (270 mg) was added at 0° C. and the temperature was raised to rt. After 1 h the mixture was quenched by addition of 5% NaH$_2$PO$_4$ and extracted with CH$_2$Cl$_2$. The combined organic extracts were washed with brine, dried over Na$_2$SO$_4$ and evaporated to dryness. The residue was dissolved in dioxane (25 mL) and 1N HCl (8 mL) was added. The resulting mixture was stirred at room temperature for 1 h and evaporated to dryness. The residue was purified by flash chromatography (SiO$_2$, n-hexane/CH$_2$Cl$_2$/acetone 50/25/25) to give the title compound II-br in 73% yield. $^1$H-NMR (300 MHz, DMSO-d$_6$, ppm from TMS): δ 4.36 (1H, t), 4.26 (1H, d), 3.86 (1H, m), 3.43 (2H, m), 2.40-1.10 (19H, m), 0.99 (3H, s), 0.79 (3H, s).

PREPARATION 60

7α-Methoxymethylandrostane-3,17-dione (II-bs)

Following the procedure described in Prepn. 15 and starting from 3,3:17,17-bis(ethylendioxy)-7α-hydroxymethylandrostane (Prepn. 34, (2.00 g), the title compound II-bs was obtained in 70% yield. $^1$H-NMR (300 MHz, acetone-d$_6$, ppm from TMS): δ 3.30 (3H, s), 3.28 (2H, m), 2.53-0.75 (21H, m), 1.13 (3H, s), 0.90 (3H, s).

PREPARATION 61

7α-Methoxyandrostane-3,17-dione (II-bt)

Following the procedure described in Prepn. 15 and starting from 3,3:17,17-bis(ethylendioxy)-7α-hydroxyandrostane (Prepn. 35, 1.50 g), the title compound II-bt was obtained in 68% yield. $^1$H-NMR (300 MHz, acetone-d$_6$, ppm from TMS): δ 3.35 (3H, s), 2.58-1.00 (21H, m), 0.96 (3H, s), 0.78 (3H, s).

PREPARATION 62

(Z) 3-[(S)-3-N-(9H-Fluoren-9-ylmethyl)pyrrolidinyl]oxyimino-5α-hydroxy-6-(E)-hydroxyiminoandrostane-3,17-dione (II-bu) and (E) 3-[(S)-3-N-(9H-Fluoren-9-ylmethyl)pyrrolidinyl]oxyimino-5α-hydroxy-6-(E)-hydroxyiminoandrostane-3,17-dione (II-bv)

The title compounds were obtained following the procedure described in Example 1 and starting from 5α-hydroxy-6-(E)-hydroxyiminoandrostane-3,17-dione (II-aq, Prepn. 27, 1.6 g) and 3-(S)-pyrrolidinyloxyamine dihydrochloride (III-d, Prepn. 4, 840 mg). To the crude product (1.8 g, ratio 55/45 of the E/Z isomers) and Et$_3$N (1.4 mL) in CH$_2$Cl$_2$ (18 mL) was added, under N$_2$, at 0° C., 9-fluorenylmethoxycarbonyl chloride (1.2 g). After stirring overnight at room temperature, water was added and the mixture extracted with CH$_2$Cl$_2$. The organic phase was washed with 5% NaHCO$_3$ dried over Na$_2$SO$_4$ and evaporated to dryness. The residue was purified by flash chromatography (SiO$_2$; CH$_2$Cl$_2$/acetone 85/15) to give (Z) 3-[(S)-3-N-(9H-fluoren-9-ylmethyl)pyrrolidinyl]oxyimino-5α-hydroxy-6-(E)-hydroxyiminoandrostane-3,17-dione (II-bu, 920 mg) and (E) 3-[(S)-3-N-(9H-fluoren-9-ylmethyl)pyrrolidinyl]oxyimino-5α-hydroxy-6-(E)-hydroxyiminoandrostane-3,17-dione (II-by, 930 mg). II-bu: $^1$H-NMR (300 MHz, DMSO-d$_6$, ppm from TMS): δ 10.70 (1H, bs), 7.90-6.90 (9H, m), 4.87 (1H, bs), 4.73 (1H, bs), 4.46-4.10 (2H, m), 3.35-3.10 (6H, m), 3.15 (1H, m), 3.00 (1H, m), 2.70-1.00 (17H, m), 0.84 (3H, s), 0.78 (3H, s). II-bv: $^1$H-NMR (300 MHz, DMSO-d$_6$, ppm from TMS): δ 10.60 (1H, bs), 7.90-6.90 (9H, m), 4.86 (1H, bs), 4.73 (1H, bs), 4.46-4.10 (2H, m), 3.35-3.10 (6H, m), 3.15 (1H, m), 3.00 (1H, m), 2.70-1.00 (17H, m), 0.84 (3H, s), 0.78 (3H, s).

PREPARATION 63

6-(E)-Hydroxyiminoandrost-4-ene-3,17-dione (II-bw)

A solution of 3,3:17,17-bis(ethylendioxy)-5α-hydroxy-6-(E)-hydroxyimino-androstane (Prepn. 27) (1.05 g) and pTSA H$_2$O (4.00 g) in acetone (100 mL) was stirred at room temperature for 5 h. The solution was neutralized by addition of 5% aqueous NaHCO$_3$ and acetone was evaporated. The aqueous suspension was extracted with CH$_2$Cl$_2$ (3×). The combined organic extracts were washed with H$_2$O, dried over Na$_2$SO$_4$ and evaporated to dryness. The residue was purified by flash chromatography (SiO$_2$, n-hexane/CH$_2$Cl$_2$/acetone 80/10/10) to give the title compound II-bw in 67% yield. $^1$H-NMR (300 MHz, DMSO-d$_6$, ppm from TMS): δ 11.60 (1H, s), 5.90 (1H, s), 3.36 (1H, d), 2.60-1.15 (16H, m), 1.08 (3H, s), 0.82 (3H, s)

PREPARATION 64

(RS) 3-Bromopyrrolidine hydrochloride

To a solution of (RS) 1-tert-butoxycarbonyl-3-pyrrolidinol (Prepn. 3) (3.00 g) in THF (90 mL), triphenylphosphine (12.4 g) was added, then a solution of CBr$_4$ (15.7 g) in THF (90 mL) was dropped and the mixture stirred overnight at room temperature. The organic solvent was evaporated and the residue was extracted with EtOAc (4×50 mL). The combined organic extracts were washed with H$_2$O, dried over Na$_2$SO$_4$ and evaporated to dryness. The residue was purified by flash chromatography (SiO$_2$, cyclohexane/EtOAc 80/20) to give (RS) 1-tert-butoxycarbonyl-3-bromopyrrolidine in 80% yield as yellow oil. $^1$H-NMR (300 MHz, DMSO-d$_6$, ppm from TMS): δ 4.85 (1H, m), 3.70-3.59 (1H, m), 3.55-2.10 (5H, m), 1.35 (9H, s).

The title compound was obtained in 75% yield following the procedure described in Prepn. 1. $^1$H-NMR (300 MHz, DMSO-d$_6$, ppm from TMS): δ 9.50 (2H, bb), 4.85 (1H, m), 3.70-3.59 (1H, m), 3.55-2.10 (5H, m).

BIOLOGICAL RESULTS

To test the inhibition of the enzymatic activity of the Na$^+$, K$^+$-ATPase, the Na$^+$, K$^+$-ATPase was purified according to Jorghensen (Jorghensen P., BBA, 1974, 356, 36) and Erdmann (Erdmann E. et al., Arzneim. Forsh., 1984, 34, 1314) and the inhibition was measured as % of hydrolysis of $^{32}$P-ATP in presence and in absence of the tested compound (Mall F. et al., Biochem. Pharmacol., 1984, 33, 47; see Table 1).

TABLE 1

Dog Kidney Na$^+$, K$^+$-ATPase Inhibition

| Example n° | Na$^+$, K$^+$-ATPase Inhibition IC$_{50}$, µM | Example n° | Na$^+$, K$^+$-ATPase Inhibition IC$_{50}$, µM |
|---|---|---|---|
| I-aa | 4.1 | I-ab | 0.26 |
| I-ac | 0.11 | I-ad | 0.83 |
| I-ae | 0.026 | I-af | 0.016 |
| I-ag | 0.11 | I-ah | 23 |
| I-ai | 11 | I-aj | 33 |
| I-ak | 41 | I-al | 1.3 |
| I-am | 0.21 | I-an | 0.58 |

TABLE 1-continued

Dog Kidney Na+, K+-ATPase Inhibition

| Example n° | Na+, K+-ATPase Inhibition IC$_{50}$, μM | Example n° | Na+, K+-ATPase Inhibition IC$_{50}$, μM |
|---|---|---|---|
| I-ao | 2.3 | I-ap | 0.38 |
| I-aq | 0.046 | I-ar | 0.026 |
| I-as | 0.32 | I-at | 0.14 |
| I-au | 0.16 | I-av | 0.016 |
| I-aw | 0.34 | I-ax | 0.26 |
| I-ay | 0.041 | I-az | 0.021 |
| I-ba | 0.22 | I-bb | 0.11 |
| I-bc | 0.058 | I-bd | 0.018 |
| I-be | 0.26 | I-bf | 7.6 |
| I-bg | 5.7 | I-bh | 0.012 |
| I-bi | 6.0 | I-bj | 0.48 |
| I-bk | 0.48 | I-bl | 92 |
| I-bm | 1.4 | I-bn | 95 |
| I-bo | 21 | I-bp | 0.041 |
| I-bq | 0.081 | I-br | 86 |
| I-bs | 1.9 | I-bt | 13 |
| I-bu | 0.11 | I-bv | 0.15 |
| I-bw | 0.039 | I-bx | 96 |
| I-by | 12 | I-bz | 94 |
| I-ca | 6.0 | I-cb | 0.089 |
| I-cc | 0.57 | I-cd | 0.038 |
| I-ce | 3.0 | I-cf | 4.0 |
| I-cg | 0.24 | I-ch | 0.16 |
| I-ci | 0.33 | I-cj | 0.22 |
| I-ck | 0.21 | I-cl | 0.15 |
| I-cm | 0.14 | I-cn | 0.34 |
| I-co | 0.024 | I-cp | 4.6 |
| I-cq | 0.96 | I-cr | 1.0 |
| I-cs | 0.013 | I-ct | 0.27 |
| I-cu | 2.6 | I-cv | 92 |
| I-cw | 11 | I-cx | 4.2 |
| I-cy | 4.2 | I-cz | 12 |
| I-da | 68 | I-db | 20 |
| I-dc | 95 | I-dd | 24 |
| I-de | 0.39 | I-df | 0.36 |
| I-dg | 0.89 | I-dh | 0.83 |
| I-di | 0.21 | I-dj | 0.036 |
| I-dk | 0.0058 | I-dl | 0.17 |
| I-dm | 8.1 | I-dn | 5.9 |
| I-do | 0.49 | I-dp | 1.2 |
| I-dq | 1.1 | I-dr | 0.87 |
| I-ds | 0.0067 | I-dt | 3.8 |
| I-du | 0.030 | I-dv | 0.22 |
| I-dw | 1.1 | I-dx | 0.050 |
| digoxin | 0.40 | compd 22b | 0.33 |

Moreover the compounds of the invention possess positive inotropic features, as shown by slow intravenous infusion in anesthetized guinea pig according to Cerri (Cerri A. et al., J. Med. Chem. 2000, 43, 2332) and have a low toxicity, i.e. a better therapeutic ratio, when compared with standard cardiotonic steroids, e.g. digoxin.

The compounds of the present invention show a higher efficacy and/or a better therapeutic ratio and/or a longer duration of action compared to compound 22b ((EZ) 3-(2-aminoethoxyimino)androstane-6,17-dione hydrochloride) reported by S. De Munari et al. in J. Med. Chem. 2003, 64, 3644-3654.

The activity of some compounds of general formula (I) on the above mentioned tests was determined and the results are shown in the following Table 2. The inotropic activity is shown as maximum increase in contractile force ($E_{max}$ measured as +dP/dT$_{max}$), dose inducing maximum positive inotropic effect (ED$_{max}$), inotropic potency (ED$_{80}$, dose increasing +dP/dT$_{max}$ by 80%); the toxicity, as the ratio between lethal dose and inotropic potency, or safety ratio, (calculated for the died animals); the maximum dose infused in the survived animals; the duration of the inotropic effect as the decrease of the effect from the ED$_{max}$ measured 20 minutes after the end of the infusion.

TABLE 2

Inotropic Effect and Lethal Dose in Anesthetized Guinea-pig.

Slow intravenous infusion (over 90 minutes) in anesthetized guinea-pig

| Example N° | $E_{max}$ % increase in +dP/dT$_{max}$ | ED$_{max}$ μmol/kg | ED$_{80}$ μmol/kg | Dead/ treated | Lethal dose/ ED$_{80}$ (safety ratio) | Maximum dose infused | % decrease from $E_{max}$ after 20 min from the end of the infusion |
|---|---|---|---|---|---|---|---|
| I-ae | 147 | 4.26 | 2.28 | 0/3 | nd | 6.4 | 74 |
| I-am | 221 | 15.3 | 3.87 | 0/3 | nd | 25.2 | 100 |
| I-at | 109 | 8.82 | 2.21 | 0/4 | nd | 25.0 | 16 |
| I-au | 164 | 23.3 | 11.0 | 0/4 | nd | 50.3 | 58 |
| I-av | 144 | 4.30 | 1.49 | 0/3 | nd | 6.3 | 100 |
| I-az | 244 | 18.4 | 6.69 | 0/3 | nd | 25.2 | 20 |
| I-bb | 147 | 6.39 | 3.70 | 0/3 | nd | 6.5 | 29 |
| I-bc | 183 | 5.08 | 1.89 | 0/3 | nd | 6.3 | 28 |
| I-bh | 173 | 3.80 | 1.91 | 0/3 | nd | 6.4 | 63 |
| I-bp | 226 | 1.80 | 0.37 | 4/4 | 36 | 4.3 | 100 |
| I-bq | 380 | 3.72 | 0.59 | 3/3 | 32 | 18.7 | — |
| I-cl | 187 | 6.34 | 3.34 | 0/3 | nd | 6.4 | 7 |
| I-dp | 358 | 43.6 | 3.92 | 2/2 | 49 | 148 | — |
| digoxin | 158 | 0.65 | 0.29 | 10/10 | 4.0 | 1.16 | 100 |
| compd 22b | 182 | 5.74 | 1.82 | 7/8 | 22.6 | 32.1 | 100 |

As reported in Table 2, the compounds showed positive inotropic effects with higher safety ratios than those displayed by digoxin and compd 22b. In fact the safety ratios (lethal dose/$ED_{80}$ ratios) were either higher or even not determinable, when no animals died; noteworthy, for some compounds a lower percentage of animals died in comparison to digoxin and compd 22b. Further, some compounds showed prolonged action as shown by the persistence of the inotropic effect after stopping the infusion (% decrease from $E_{max}$ after 20 min from the end of the infusion). When no animal died, higher doses were not tested since the maximum increases in contractile force were comparable or higher to those displayed by digoxin and compd 22b.

Further data on longer duration of action of the compounds of the present invention were generated and these are shown in Table 3, where the results of the metabolism of the compounds in fresh rat hepatocytes (from Sprague Dawley, males, weights in the range 285-295 grams; viability 80-90%; concentration: 2590000-3084000 hepatocytes/ml; test item nominal concentration: 45 µM) are reported in comparison with compd 22b which is almost completely metabolized within 60 minutes.

TABLE 3

Metabolism in rat hepatocytes

| Example N° | % of compound metabolized after 60 minutes |
|---|---|
| I-am | 12 |
| I-an | 21 |
| I-be | 42 |
| I-bp | 8 |
| I-bw | 24 |
| I-cg | 28 |
| I-cj | 20 |
| I-cs | 5 |
| I-db | 25 |
| I-dk | 5 |
| compound 22b | 95 |

The compounds of the present invention possess also antihypertensive activity, as taught by P. Ferrari et al., in *Cardiovascular Drug Reviews*, 1999, 17, 39-57, who demonstrated that compounds affecting $Na^+$, $K^+$-ATPase can lower blood pressure in models of hypertension.

The ability of these compounds to lower blood pressure was tested by using an animal model with induced hypertension, in particular, rats made hypertensive by chronic infusion of ouabain, according to Ferrari P., et al. J. Pharm. Exp. Ther. 1998, 285, 83-94.

The procedure adopted to test the antihypertensive activity of the compounds on the above mentioned model was the following: systolic blood pressure (SBP) and heart rate (HR) were measured by an indirect tailcuff method. The blood pressure lowering effect was measured in hypertensive ouabain-sensitive rats. The compound, suspended in Methocel 0.5% (w/v), was administered daily at the dose of 10 µg/kg/day by mouth for four weeks. SBP and HR were measured weekly 6 hours after the treatment. The comparison are ouabain sensitive rats (OS rats) and non hypertensive rats (control), both treated only with Methocel 0.5% (w/v). As shown in the following Table 4, treatment with a compound of the present invention lowers the blood pressure of OS rats (170 mm Hg) to almost the level of control rats (150 mm Hg).

TABLE 4

Systolic blood pressure fall in hypertensive ouabain-sensitive rats (os rats)

| EXAMPLE n° | RATS | SBP mmHg | SBP - mmHg | SBP - % | HR beats/min. | HR % beats/min |
|---|---|---|---|---|---|---|
| Comp. I-db | 8 | 153.0 | 17.0 | 10.3 | 387 | +6.6 |
| OS rats | 8 | 170.0 | — | — | 368 | — |
| Control | 8 | 150.0 | — | — | 376 | — |

The invention claimed is:
1. Compounds of formula (I)

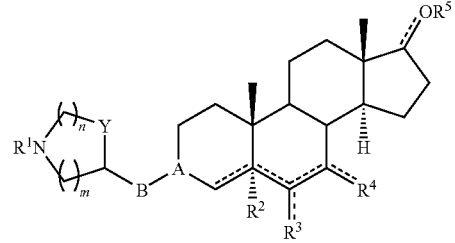

wherein:
A is C=N~O, $CR^6$~CH=CH~ ~and $CR^6$~$CH_2$, wherein the left end carbon atom in any of these groups is at position 3 of the androstane ring;
where:
$R^6$ is hydrogen or hydroxy;
B is a single bond so that the A is directly linked to the nitrogen-containing heterocycle;
Y is $CH_2$ or oxygen;
$R^1$ is H, $C_1$-$C_6$ straight or branched alkyl;
$R^2$ is H, $C_1$-$C_6$ straight or branched alkyl, $ONO_2$, $OR^{11}$;
$R^{11}$ is H, $C_1$-$C_6$ straight or branched alkyl, optionally substituted by one hydroxy, methoxy, ethoxy or $R^{11}$ is allyl or propargyl;
when the bonds === linking the carbon atom in position 6 of the androstane skeleton with $R^3$ and/or the carbon atom in position 7 with $R^4$ are a double bond, $R^3$ and $R^4$, being $R^3$ and $R^4$ the same or different, are, O, with the meaning of a keto group, N~$OR^{12}$ or $CR^{13}R^{14}$;
$R^{12}$ is H, $C_1$-$C_6$ straight or branched alkyl group, optionally substituted by one or more hydroxy, methoxy, ethoxy groups, or $R^{12}$ is allyl or propargyl;
$R^{13}$ and $R^{14}$, which can be the same or different, are H, $C_1$-$C_6$ straight or branched alkyl group, optionally substituted by one hydroxy, methoxy, ethoxy, or $R^{13}$ and $R^{14}$, which can be the same or different, are allyl, propargyl, F, $COOR^{15}$, CN, $CONR^{16}R^{17}$, or $R^{13}$ and $R^{14}$ taken together form a cycloalkylene substituent;
$R^{15}$ is H, $C_1$-$C_6$ straight or branched alkyl, optionally substituted by one hydroxy, methoxy or ethoxy;
$R^{16}$ and $R^{17}$, which can be the same or different, are H, $C_1$-$C_6$ straight or branched alkyl group, or $R^{16}$ and $R^{17}$ can optionally be taken together with the nitrogen atom to form a heterocyclic group;
when the bonds === linking the carbon atom in position 6 of the androstane skeleton with $R^3$ and/or the carbon atom in position 7 with $R^4$ are single bonds, $R^3$ and/or $R^4$, which can be the same or different, are H, $C_1$-$C_6$ straight or branched alkyl group, vinyl, ethynyl, COOR$^{15}$, CN, CONR$^{16}$R$^{17}$, OR$^{18}$, ONO$_2$, NHCHO, NHCOCH$_3$, CH=N—OH, spirocyclopropane, spirooxirane, where the alkyl group can be optionally substituted by one hydroxy, methoxy or ethoxy;

R$^{15}$, R$^{16}$, and R$^{17}$ are as above defined,

R$^{18}$ is H, C$_1$-C$_6$ straight or branched alkyl optionally substituted by one or more hydroxy, methoxy, ethoxy;

R$^5$ is H, C$_1$-C$_6$ straight or branched alkyl group or C$_2$-C$_6$ acyl group when the bond === in position 17 of the androstane skeleton is a single bond and, as a consequence, the remaining substituent in position 17 is H, and R$^5$ is not present when the bond === in position 17 is a double bond with the meaning of a keto group;

n is the number 0 or 1 or 2 or 3;

m is the number 0 or 1 or 2 or 3;

R$^{15}$, R$^{16}$, and R$^{17}$, when present in the same compound in different positions, can be the same or different, the symbol ⋯ is an α or β single bond or an E or Z diastereoisomer when it is linked to a double bond, the symbol === in positions 4, 5, 6, 7, and 17 is, independently, a single or double bond, and when it is a single exocyclic bond in positions 6, 7, or 17, it can be an α or β single bond;

with the following provisos:

that at least one of R$^2$, R$^3$ and R$^4$ in the same structure is not hydrogen;

their tautomers, all the possible stereoisomers, Z and E isomers, optical isomers and their mixtures, their metabolites and the metabolic precursors, the pharmaceutically acceptable salts.

2. Compounds according to claim 1, wherein R$^2$ and R$^4$ represent H, the symbol R$^3$ represents oxygen, with the meaning of keto; methylene, difluoromethylene, hydroxyimino, methoxyimino, and the symbol

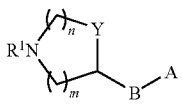

represents (R-3-pyrrolidinyloxy)imino, (S-3-pyrrolidinyloxy)imino, (RS-3-pyrrolidinyloxy)imino, 3-azetidinyloxyimino, [3-(R)-(1-methyl)pyrrolidinyl]-oxyimino, [3-(S)-(1-methyl)pyrrolidinyl]oxyimino, 3α-[2-(pyrrolidin-3-(R)-yl)(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl], their tautomers, all the possible stereoisomers, Z and E isomers, optical isomers and their mixtures, their metabolites and the metabolic precursors, the pharmaceutically acceptable salts.

3. Compounds according to claim 1, wherein R$^2$ and R$^4$ represent H, the symbol R$^3$ represents α-hydroxy, α-methyl, α-carbamoyl, α-methoxycarbonyl, α-hydroxymethyl, α-(2-hydroxyethyl), α-methoxy-methyl, α-nitroxy, α-formylamino, α-ethynyl, β-hydroxy, spirocyclopropyl, the symbol === in position 17 represents a double bond or a β-single bond while the other symbols === represent single bonds, and the symbol

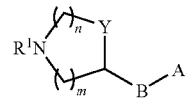

represents (R-3-pyrrolidinyloxy)imino, (S-3-pyrrolidinyloxy)imino, (RS-3-pyrrolidinyloxy)imino, 3-azetidinyloxyimino, [3-(R)-(1-methyl)pyrrolidinyl]-oxyimino, [3-(S)-(1-methyl)pyrrolidinyl]oxyimino, 3α-[2-(pyrrolidin-3-(R)-yl)(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl], their tautomers, all the possible stereoisomers, Z and E isomers, optical isomers and their mixtures, their metabolites and the metabolic precursors, the pharmaceutically acceptable salts.

4. Compounds according to claim 1, wherein R$^2$ represents hydroxy, the symbol R$^4$ represents H, the symbol R$^3$ represents oxygen with the meaning of keto; methylene, difluoromethylene, hydroxyimino, methoxyimino, when the symbols === in position 6 linking R$^3$ and in position 17 represent double bonds, while the other symbols === represent single bonds, and the symbol

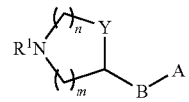

represents (R-3-pyrrolidinyl-oxy)imino, (S-3-pyrrolidinyloxy)imino, (RS-3-pyrrolidinyloxy)imino, 3-azetidinyloxyimino, [3-(R)-(1-methyl)pyrrolidinyl]-oxyimino, [3-(S)-(1-methyl)pyrrolidinyl]oxyimino, 3α-[2-(pyrrolidin-3-(R)-yl)(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl], their tautomers, all the possible stereoisomers, Z and E isomers, optical isomers and their mixtures, their metabolites and the metabolic precursors, the pharmaceutically acceptable salts.

5. Compounds according to claim 1, wherein R$^2$ and R$^3$ represent H, the symbol R$^4$ represents oxygen, with the meaning of keto; methylene, difluoromethylene, hydroxyimino, methoxyimino, when the symbols === in position 7 linking R$^4$ and in position 17 represent a double bond, while the other symbols === represent single bonds, and the symbol

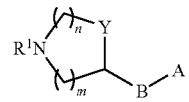

represents (R-3-pyrrolidinyloxy)imino, (S-3-pyrrolidinyloxy)imino, (RS-3-pyrrolidinyloxy)imino, 3-azetidinyloxyimino, 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)vinyl], their tautomers, all the possible stereoisomers, Z and E isomers, optical isomers and their mixtures, their metabolites and the metabolic precursors, the pharmaceutically acceptable salts.

6. Compounds according to claim 1, wherein R$^2$ and R$^3$ represent H, the symbol R$^4$ represents α-hydroxy, α-methyl, α-carbamoyl, α-methoxycarbonyl, α-hydroxymethyl, α-methoxymethyl, α-nitroxy, α-formylamino, α-ethynyl,
β-hydroxy, β-methyl, β-carbamoyl, β-methoxycarbonyl, β-hydroxymethyl,
β-methoxymethyl, β-nitroxy, β-formylamino, β-ethynyl, spirocyclopropyl, the symbol === in position 17 represents a double bond while the other symbols === represent single bonds, and the symbol

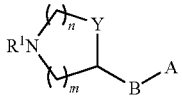

represents (R-3-pyrrolidinyloxy)imino, (S-3-pyrrolidinyloxy)imino, (RS-3-pyrrolidinyloxy)imino, 3-azetidinyloxyimino, 3α-[2-(pyrrolidin-3-(R)-yl)-(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)vinyl], their tautomers, all the possible stereoisomers, Z and E isomers, optical isomers and their mixtures, their metabolites and the metabolic precursors, the pharmaceutically acceptable salts.

7. Compounds according to claim 1, wherein $R^2$ represents hydroxy, the symbols $R^3$ and $R^4$ represent H, the symbol === in position 17 represents a double bond while the other symbols === represent single bonds, and the symbol

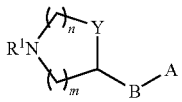

represents (R-3-pyrrolidinyloxy)imino, (S-3-pyrrolidinyloxy)imino, (RS-3-pyrrolidinyloxy)imino, 3-azetidinyloxyimino 3α-[2-(pyrrolidin-3-(R)-yl)-(Z)-vinyl], 3α-[2-(pyrrolidin-3-(S)-yl)-(Z)vinyl], 3α-[2-(azetidin-3-yl)-(Z)-vinyl], 3α-[2-(piperidin-4-yl)-(Z)-vinyl], their tautomers, all the possible stereoisomers, Z and E isomers, optical isomers and their mixtures, their metabolites and the metabolic precursors, the pharmaceutically acceptable salts.

8. Compounds according to claim 1, wherein $R^2$ represents H, the symbols $R^3$ represents α-hydroxymethyl, and $R^4$ represents α-hydroxy or keto, when the symbol === in position 17 represents a double bond while the other symbols === represent single bonds, and the symbol

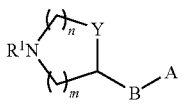

represents (R-3-pyrrolidinyloxy)imino, (S-3-pyrrolidinyloxy)imino, (RS-3-pyrrolidinyloxy)imino, 3-azetidinyloxyimino, [3-(R)-(1-methyl)pyrrolidinyl]-oxyimino, [3-(S)-(1-methyl)pyrrolidinyl]oxyimino 3α-[2-(pyrrolidin-3-(R)-yl)(Z)-vinyl], 3α-[2-(pyrrolidin-3-(S)-yl)-(Z)-vinyl], 3α-[2-(azetidin-3-yl)-(Z)-vinyl], 3α-[2-(piperidin-4-yl)-(Z)-vinyl], their tautomers, all the possible stereoisomers, Z and E isomers, optical isomers and their mixtures, their metabolites and the metabolic precursors, the pharmaceutically acceptable salts.

9. Compounds according to claim 1, selected from the group consisting of:
(E) 3-[3'-(R)-(1-methyl)pyrrolidinyl]oxyiminoandrostane-6,17-dione;
(E) 3-(4-piperidyl)oxyiminoandrostane-6,17-dione hydrochloride;
(E,Z) 3-(3-azetidinyl)oxyiminoandrostane-6,17-dione fumarate;
(E) 3-[3-(RS)-pyrrolidinyl]oxyiminoandrostane-6,17-dione hydrochloride;
(E,Z) 3-[3-(S)-pyrrolidinyl]oxyiminoandrostane-6,17-dione hydrochloride;
(E,Z) 3-[3-(R)-pyrrolidinyl]oxyiminoandrostane-6,17-dione hydrochloride;
(E) 3-[3-(R)-pyrrolidinyl]oxyiminoandrostane-6,17-dione hydrochloride;
(Z)-3-[3'-(R)-pyrrolidinyl]oxyiminoandrostane-6,17-dione hydrochloride;
(E) 3-[3'-(R,S)-Piperidinyl]oxyiminoandrostane-6,17-dione hydrochloride;
(E,Z) 3-[3'-(S)-(1-methyl)pyrrolidinyl]oxyiminoandrostane-6,17-dione hydrochloride;
(E,Z) 3-(3-(R)-pyrrolidinyl)oxyimino-5α-hydroxyandrostane-17-one hemifumarate;
(E,Z) 3-[3-(R)-pyrrolidinyl]oxyimino-6α-hydroxyandrostan-17-one hydrochloride;
(E,Z) 3-[3-(S)-pyrrolidinyl]oxyimino-6α-hydroxyandrostan-17-one hydrochloride;
(E,Z) 3-[3-(R)-pyrrolidinyl]oxyimino-17-oxoandrostane-6α-yl nitrate hydrochloride;
(E,Z) 3-[3-(R)-pyrrolidinyl]oxyimino-6-methyleneandrostane-17-one hydrochloride;
(E,Z) 3-[3-(R)-pyrrolidinyl]oxyimino-6α-hydroxymethylandrostan-17-one hydrochloride;
(E,Z) 3-[3-(R)-pyrrolidinyl]oxyimino-6α-methoxymethylandrostane-17-one hydrochloride;
(Z,E) 3-(3-(R)-pyrrolidinyloxyimino)-6α-carbamoylandrostane-17-one hydrochloride;
(Z,E) 3-(3-(R)-pyrrolidinyloxyimino)-6α-methoxycarbonylandrostane-17-one hydrochloride;
(E,Z) 3-[3-(R)-pyrrolidinyl]oxyimino-6(E)-hydroxyiminoandrostan-17-one hydrochloride;
(E) 3-[3-(R)-pyrrolidinyl]oxyimino-6α-methylandrostane-17-one fumarate;
(Z) 3-[3-(R)-pyrrolidinyl]oxyimino-6α-methylandrostane-17-one hydrochloride;
(E,Z) 3-[3-(R)-pyrrolidinyl]oxyimino-6α-formamidoandrostane-17-one hydrochloride;
(E,Z) 3-[3-(R)-pyrrolidinyl]oxyimino-6-difluoromethyleneandrostan-17-one hydrochloride;
(Z,E) 3-(3-(R)-pyrrolidinyloxyimino)-6-(spirocyclopropane)androstane-17-one hydrochloride;
(E,Z) 3-[3'-(R)-pyrrolidinyl]oxyimino-6α-ethynylandrostane-17-one hydrochloride;
(E,Z) 3-[3'-(R)-pyrrolidinyl]oxyimino-6α-(2-hydroxyethyl)androstane-17-one hydrochloride;
(E,Z) 3-(3'-(R)-pyrrolidinyloxyimino)-6-(E)-methoxyiminoandrostan-17-one hydrochloride;
(E,Z) 3-[3'-(S)-pyrrolidinyl]oxyimino-6-(E)-methoxyiminoandrostane-17-one fumarate;
(E,Z) 3-[3'-(S)-(1-methyl)pyrrolidinyl]oxyimino-6-(E)-methoxyimino-androstane-17-one hydrochloride;
(E,Z) 3-[3'-(R)-(1-methyl)pyrrolidinyl]oxyimino-(E)-6-methoxyimino-androstane-17-one hydrochloride;
(E,Z) 3-[3'-(R)-pyrrolidinyl]oxyimino-5α-hydroxy-6-methyleneandrostane-17-one hydrochloride;

(Z) 3-[3'-(S)-pyrrolidinyl]oxyimino-5α-hydroxy-6-methyleneandrostane-17-one fumarate;
(E) 3-[3'-(S)-pyrrolidinyl]oxyimino-5α-hydroxy-6-methyleneandrostane-17-one fumarate;
(E,Z) 3-[3'-(S)-pyrrolidinyl]oxyimino-5α-hydroxy-6-methyleneandrostane-17-one fumarate;
(Z) 3-[3'-(R)-(1-methyl)pyrrolidinyl]oxyimino-5α-hydroxy-6-methylene-androstane-17-one fumarate;
(E) 3-[3'-(R)-(1-methyl)pyrrolidinyl]oxyimino-5α-hydroxy-6-methylene-androstane-17-one fumarate;
(Z) 3-[3'-(S)-(1-methyl)pyrrolidinyl]oxyimino)-5α-hydroxy-6-methylene-androstane-17-one fumarate;
(E) 3-[3'-(S)-(1-methyl)pyrrolidinyl]oxyimino)-5α-hydroxy-6-methylene-androstane-17-one fumarate;
(E,Z) 3-[3-(R)-pyrrolidinyl]oxyimino-5α-hydroxy-6-(E)-hydroxyimino-androstane-17-one hydrochloride;
(E,Z) 3-[3-(S)-pyrrolidinyl]oxyimino-5α-hydroxy-6-(E)-hydroxyimino-androstane-17-one hydrochloride;
(Z) 3-[3'-(S)-(1-methyl)pyrrolidinyl]oxyimino-5α-hydroxy-6-(E)-hydroxyiminoandrostane-17-one hemifumarate;
(E) 3-[3'-(S)-(1-methyl)pyrrolidinyl]oxyimino-5α-hydroxy-6-(E)-hydroxyiminoandrostane-17-one fumarate;
(Z) 3-[3'-(R)-(1-methyl)pyrrolidinyl]oxyimino-5α-hydroxy-6-(E)-hydroxyiminoandrostane-17-one fumarate;
(E) 3-[3'-(R)-(1-methyl)pyrrolidinyl]oxyimino-5α-hydroxy-6-(E)-hydroxyiminoandrostane-17-one fumarate;
(E,Z)-3-(3'-(S)-pyrrolidinyloxyimino)-5α-hydroxy-6-(E)-methoxyimino-androstane-17-one fumarate;
(E,Z) 3-[3'-(R)-pyrrolidinyl]oxyimino-5α-hydroxy-6-(E)-methoxyimino-androstane-17-one fumarate;
(Z) 3-[3'-(S)-(1-methyl)pyrrolidinyl]oxyimino)-5α-hydroxy-6-(E)-methoxyiminoandrostane-17-one fumarate;
(E) 3-[3'-(S)-(1-methyl)pyrrolidinyl]oxyimino)-5α-hydroxy-6-(E)-methoxyiminoandrostane-17-one fumarate;
(Z) 3-[3'-(R)-(1-methyl)pyrrolidinyl]oxyimino)-5α-hydroxy-6-(E)-methoxyiminoandrostane-17-one fumarate;
(E) 3-[3'-(R)-(1-methyl)pyrrolidinyl]oxyimino)-5α-hydroxy-6-(E)-methoxyiminoandrostane-17-one fumarate;
(E,Z) 3-[3-(R)-pyrrolidinyl]oxyiminoandrostane-7,17-dione fumarate;
(E,Z) 3-[3'-(S)-pyrrolidinyl]oxyiminoandrostane-7,17-dione fumarate;
(E,Z) 3-[3-(R)-pyrrolidinyl]oxyimino-7(E)-hydroxyiminoandrostan-17-one fumarate;
(E,Z) 3-[3-(R)-pyrrolidinyl]oxyimino-7(E)-methoxyiminoandrostan-17-one fumarate;
(E,Z) 3-[3'-(R)-pyrrolidinyl]oxyimino-7-(E)-allyloxyiminoandrostane-17-one fumarate;
(E,Z) 3-[3'-(R)-pyrrolidinyl]oxyimino-7-methyleneandrostane-17-one hydrochloride;
(E,Z) 3-[3'-(R)-pyrrolidinyl]oxyimino-7α-hydroxymethylandrostane-17-one hydrochloride;
(E,Z) 3-[3'-(R)-pyrrolidinyl]oxyimino-7β-hydroxymethylandrostane-17-one hydrochloride;
(E,Z) 3-[3'-(R)-pyrrolidinyl]oxyimino-7α-hydroxyandrostane-17-one fumarate;
(E,Z) 3-[3'-(R)-pyrrolidinyl]oxyimino-7α-methylandrostane-17-one hydrochloride;
(E,Z) 3-[3'-(R)-pyrrolidinyl]oxyimino-7β-methylandrostane-17-one hydrochloride;
(E) 3-[3'-(R)-pyrrolidinyl]oxyimino-7β-methylandrostane-17-one hydrochloride;
(Z) 3-[3'-(R)-pyrrolidinyl]oxyimino-7β-methylandrostane-17-one hydrochloride;
(Z,E) 3-(3'-(R)-pyrrolidinyloxyimino)-7-(spirocyclopropane)androstane-17-one hydrochloride;
(E,Z) 3-[3'-(R)-pyrrolidinyl]oxyimino-7α-formamidoandrostane-17-one hydrochloride;
(E) 3-[3'-(R)-pyrrolidinyl]oxyimino-7α-methoxycarbonylandrostane-17-one hydrochloride;
(E,Z) 3-(3'-(R)-pyrrolidinyloxyimino)-6-(E)-hydroxyimino-7α-hydroxyandrostane-17-one hydrochloride;
(E,Z) 3-[3'-(R)-pyrrolidinyl]oxyimino-6α-hydroxymethylandrostane-7,17-dione fumarate;
(E,Z) 3-[3'-(R)-(1-methyl)pyrrolidinyl]oxyimino-6α-hydroxymethyl-androstane-7,17-dione fumarate;
(E,Z) 3-[3'-(S)-(1-methyl)pyrrolidinyl]oxyimino-6α-hydroxymethyl-androstane-7,17-dione fumarate;
3α-[2-(Pyrrolidin-3-(S)-yl)-(Z)-vinyl]androstane-6,17-dione formate;
3α-[2-(Pyrrolidin-3-(R)-yl)-(Z)-vinyl]androstane-6,17-dione formate;
3α-[2-(Pyperidin-4-yl)-(Z)-vinyl]androstane-6,17-dione formate;
3α-[2-(Azetidin-3-yl)-(Z)-vinyl]androstane-6,17-dione formate;
(Z)-3-[3-(S)-pyrrolidinyl)oxyimino]-6α-hydroxymethylandrostane-7,17-dione fumarate;
(E)-3-[3-(S)-pyrrolidinyl)oxyimino]-6α-hydroxymethylandrostane-7,17-dione fumarate;
(E,Z) 3-[3-(R)-pyrrolidinyl]oxyimino-6α-hydroxymethyl-7α-hydroxy-androstane-17-one hydrochloride;
(E,Z) 3-[3-(S)-pyrrolidinyl]oxyimino-6α-hydroxymethyl-7α-hydroxy-androstane-17-one hydrochloride;
(E,Z) 3-[3-(R)-pyrrolidinyl]oxyimino-7α-methoxymethylandrostane-17-one hydrochloride;
(E,Z) 3-[3-(R)-pyrrolidinyl]oxyimino-7α-methoxyandrostane-17-one fumarate;
(E,Z) 3-[3-(R)-pyrrolidinyl]oxyiminoandrostane-6α,17β-diol hydrochloride;
(E,Z) 3-[3'-(R)-pyrrolidinyl]oxyimino-6β-hydroxyandrostane-17-one hydrochloride;
(E,Z) 3-[3'-(R)-(1-methyl)pyrrolidinyl]oxyimino-5α-hydroxy-6-(E)hydroxyiminoandrostane-17-one fumarate;
(Z) 3-[3-(R)-pyrrolidinyl]oxyimino-5α-hydroxy-6-(E)-hydroxyimino-androstane-17-one fumarate;
(E) 3-[3-(R)-pyrrolidinyl]oxyimino-5α-hydroxy-6-(E)-hydroxyimino-androstane-17-one fumarate;
(Z) 3-[3-(S)-pyrrolidinyl]oxyimino-5α-hydroxy-6-(E)-hydroxyimino-androstane-17-one fumarate;
(E) 3-[3-(S)-pyrrolidinyl]oxyimino-5α-hydroxy-6-(E)-hydroxyimino-androstane-17-one fumarate;
(E,Z) 3-[3-(S)-pyrrolidinyl]oxyimino-6-(E)-hydroxyiminoandrost-4-ene-17-one fumarate;
(Z) 3-[3-(S)-pyrrolidinyl]oxyimino-6-(E)-hydroxyiminoandrost-4-ene-17-one and
(E) 3-[3-(S)-pyrrolidinyl]oxyimino-6-(E)-hydroxyiminoandrostane-4-ene-17-one;
and the corresponding pure E and Z isomers of the EZ mixtures reported above.

10. A process for the preparation of compounds of claim 1, wherein A is C=N∼O comprising reacting a compound of formula (II)

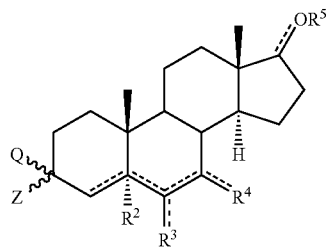

where Q and Z represent together a keto group (=O), $R^2$, $R^3$, $R^4$, $R^5$ are as defined in claim 1, with a compound of general formula (III),

where $R^1$, B, Y, m and n have the meanings defined as defined in claim 1.

11. Pharmaceutical composition comprising a compound of claim 1 in admixture with at least one pharmaceutically acceptable vehicle and/or excipient.

12. A method of treating cardiovascular disorders in mammals comprising administering an effective amount of a compound of claim 1 to a mammal in need thereof, wherein the cardiovascular disorder is hypertension.

13. A method of treating inhibiting of the enzymatic activity of the $Na^+$, $K^+$-ATPase in mammals, comprising administering an effective amount of a compound of claim 1 to a mammal in need thereof.

* * * * *

UNITED STATES PATENT AND TRADEMARK OFFICE
CERTIFICATE OF CORRECTION

PATENT NO. : 8,536,160 B2
APPLICATION NO. : 12/296532
DATED : September 17, 2013
INVENTOR(S) : Cerri et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1109 days.

Signed and Sealed this
Fifteenth Day of September, 2015

Michelle K. Lee
*Director of the United States Patent and Trademark Office*